US011230578B2

(12) United States Patent
Rotter et al.

(10) Patent No.: US 11,230,578 B2
(45) Date of Patent: Jan. 25, 2022

(54) PEPTIDES AND USE OF SAME IN THE TREATMENT OF DISEASES, DISORDERS OR CONDITIONS ASSOCIATED WITH A MUTANT P53

(71) Applicant: Yeda Research and Development Co. Ltd., Rehovot (IL)

(72) Inventors: Varda Rotter, Rehovot (IL); Moshe Oren, Rehovot (IL); Perry Tal, Rehovot (IL); Shay Eizenberger, Rehovot (IL); Avi Ben-Shimon, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 16/074,086

(22) PCT Filed: Feb. 3, 2017

(86) PCT No.: PCT/IL2017/050132
§ 371 (c)(1),
(2) Date: Jul. 31, 2018

(87) PCT Pub. No.: WO2017/134671
PCT Pub. Date: Aug. 10, 2017

(65) Prior Publication Data
US 2019/0048053 A1   Feb. 14, 2019

Related U.S. Application Data

(60) Provisional application No. 62/291,003, filed on Feb. 4, 2016.

(51) Int. Cl.
| C07K 14/47 | (2006.01) |
| C07K 7/06 | (2006.01) |
| C07K 7/08 | (2006.01) |
| A61P 35/00 | (2006.01) |
| A61K 9/00 | (2006.01) |
| A61K 38/00 | (2006.01) |

(52) U.S. Cl.
CPC ........ *C07K 14/4746* (2013.01); *A61K 9/0019* (2013.01); *A61P 35/00* (2018.01); *C07K 7/06* (2013.01); *C07K 7/08* (2013.01); *A61K 38/00* (2013.01)

(58) Field of Classification Search
CPC .......... A61P 35/00; A61P 37/00; A61P 37/02; A61P 31/12; A61P 31/04; A61K 51/08; C07K 7/06; C07K 14/001
See application file for complete search history.

(56) References Cited

U.S. PATENT DOCUMENTS

| 3,791,932 | A |  | 2/1974 | Schuurs |
| 3,839,153 | A |  | 10/1974 | Schuurs |
| 3,850,578 | A |  | 11/1974 | McConnell |
| 3,850,752 | A |  | 11/1974 | Schuurs |
| 3,853,987 | A |  | 12/1974 | Dreyer |
| 3,867,517 | A |  | 2/1975 | Chung-Mei |
| 3,879,262 | A |  | 4/1975 | Schuurs et al. |
| 3,901,654 | A |  | 8/1975 | Gross |
| 3,935,074 | A |  | 1/1976 | Rubenstein |
| 3,984,533 | A |  | 10/1976 | Uzgiris |
| 3,996,345 | A |  | 12/1976 | Ullman |
| 4,034,074 | A |  | 7/1977 | Laughton |
| 4,098,876 | A |  | 7/1978 | Piasio |
| 4,666,828 | A |  | 5/1987 | Gusella |
| 4,683,202 | A |  | 7/1987 | Mullis |
| 4,801,531 | A |  | 1/1989 | Frossard |
| 4,879,219 | A |  | 11/1989 | Wands |
| 5,011,771 | A |  | 4/1991 | Dominique |
| 5,192,659 | A |  | 3/1993 | Simons |
| 5,272,057 | A |  | 12/1993 | Smulson |
| 5,281,521 | A |  | 1/1994 | Trojanowski |
| 5,294,605 | A | * | 3/1994 | Houghten ............... C07K 14/46 514/19.3 |
| 5,614,393 | A |  | 3/1997 | Thomas et al. |
| 9,856,289 | B2 | * | 1/2018 | Oren ...................... A61K 38/16 |
| 2003/0224379 | A1 |  | 12/2003 | Tang et al. |
| 2004/0214184 | A1 |  | 10/2004 | Skubitz et al. |

(Continued)

FOREIGN PATENT DOCUMENTS

| CN | 1329493 A | 1/2002 |
| EP | 0989136 | 3/2000 |

(Continued)

OTHER PUBLICATIONS

Colloc'h et al. P-Breakers: An Aperiodic Secondary Structure. J. Mol. Biol. (1991) 221,603-613. (Year: 1991).*
Kim et al. p53 Requires an Intact C-Terminal Domain for DNA Binding and Transactivation. J Mol Biol. Feb. 3, 2012; 415(5): 843-854. (Year: 2012).*
Li et al. An all-D amino acid peptide model of alpha 1(IV)531-543 from type IV collagen binds the alpha3beta1 integrin and mediates tumor cell adhesion, spreading, and motility. Biochemistry 1997, 36, 15404-15410. (Year: 1997).*

(Continued)

*Primary Examiner* — Soren Harward
*Assistant Examiner* — Jia-Hai Lee
(74) *Attorney, Agent, or Firm* — J.A. Lindeman & Co., PLLC; Stephen C. Bellum

(57) ABSTRACT

An isolated peptide is provided. The peptide comprises an amino acid sequence arranged in a space and configuration that allow interaction of the peptide with the DNA Binding Domain (DBD) of p53 through at least one residue of the DBD by which pCAP 250 (SEQ ID NO: 1) binds the DBD, wherein the peptide at least partially reactivates a mutant p53 protein, with the proviso that the peptide is not SEQ ID NO: 59-382.

Figure 1:
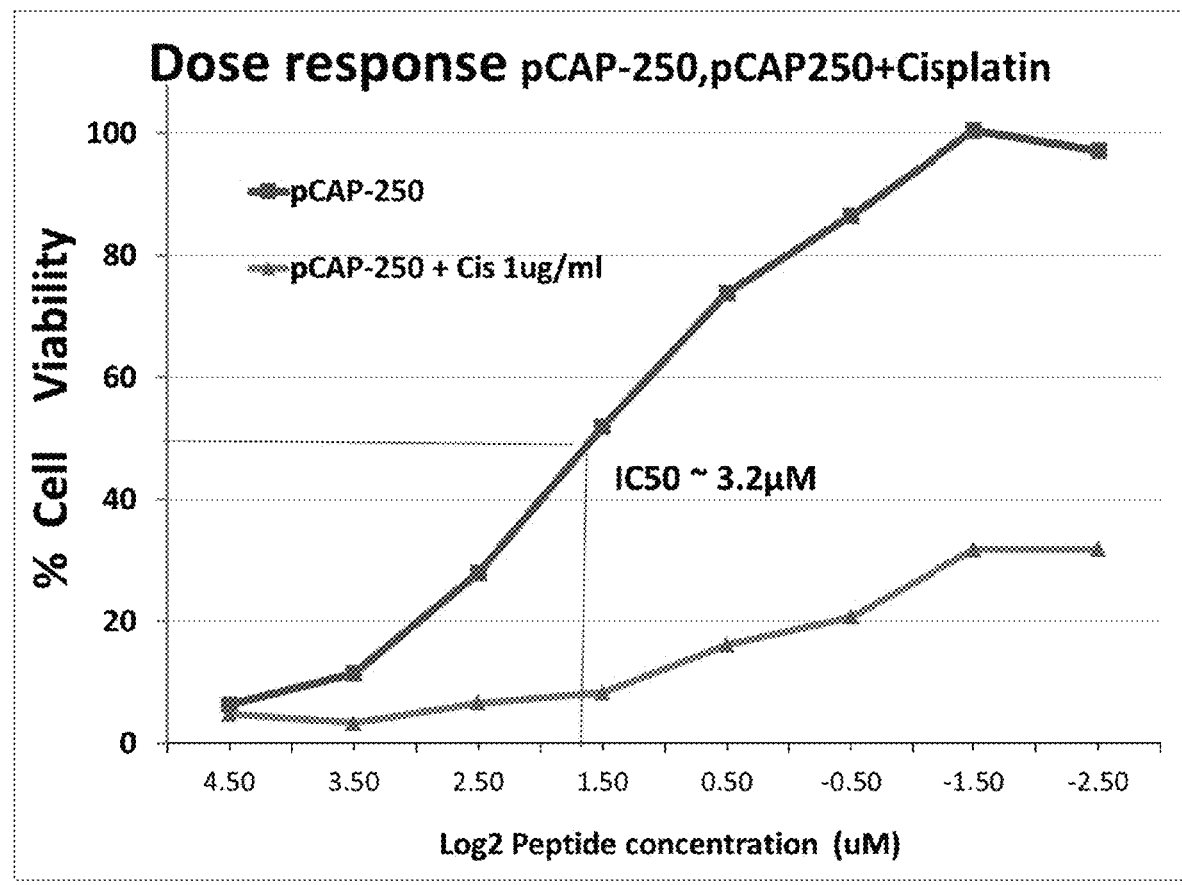

11 Claims, 17 Drawing Sheets
(15 of 17 Drawing Sheet(s) Filed in Color)
Specification includes a Sequence Listing.

(56) References Cited

U.S. PATENT DOCUMENTS

| | | | |
|---|---|---|---|
| 2006/0251726 | A1 | 11/2006 | Lin et al. |
| 2008/0069839 | A1 | 3/2008 | Guan et al. |
| 2013/0011356 | A1 | 1/2013 | Fahnestock et al. |
| 2016/0215019 | A1 | 7/2016 | Oren et al. |
| 2018/0057533 | A1 | 3/2018 | Oren et al. |
| 2019/0315804 | A1 | 10/2019 | Oren et al. |
| 2020/0095282 | A1 | 3/2020 | Oren et al. |

FOREIGN PATENT DOCUMENTS

| | | | | |
|---|---|---|---|---|
| IL | WO2015019318 A1 * | 2/2015 | | A61P 35/00 |
| JP | 11-500311 | 1/1999 | | |
| RU | 2181772 | 4/2002 | | |
| RU | 2192431 | 11/2002 | | |
| WO | 9621022 A2 | 7/1996 | | |
| WO | WO 97/21022 | 7/1996 | | |
| WO | WO 96/25434 | 8/1996 | | |
| WO | WO 97/30074 | 8/1997 | | |
| WO | WO1997030074 * | 8/1997 | | C07K 5/04 |
| WO | WO1998011907 * | 3/1998 | | A61K 38/02 |
| WO | WO 98/51707 | 11/1998 | | |
| WO | WO 02/072600 | 9/2002 | | |
| WO | WO 03/072600 | 9/2003 | | |
| WO | WO 2009/112075 | 9/2009 | | |
| WO | WO 2013/036208 | 3/2013 | | |
| WO | WO 2013/040142 | 3/2013 | | |
| WO | WO 2015/019318 | 2/2015 | | |
| WO | WO 2017/134671 | 8/2017 | | |

OTHER PUBLICATIONS

Hacke et al. Consequences of proline-to-alanine substitutions for the stability and refolding of onconase. FEBS Journal 280 (2013) 4454-4462. (Year: 2013).*
Communication Pursuant to Rule 164(1) EPC [Supplementary Partial European Search Report] dated Feb. 9, 2017 From the European Patent Office Re. Application No. 14834903.8. (9 Pages).
International Preliminary Report on Patentability dated Aug. 16, 2018 From the International Bureau of WIPO Re. Application No. PCT/IL2017/050132. (12 Pages).
International Preliminary Report on Patentability dated Feb. 18, 2016 From the International Bureau of WIPO Re. Application No. PCT/IB2014/063777.
International Search Report and the Written Opinion dated Dec. 1, 2014 From the International Searching Authority Re. Application No. PCT/IB2014/063777.
International Search Report and the Written Opinion dated Apr. 19, 2017 From the International Searching Authority Re. Application No. PCT/IL2017/050132. (20 Pages).
International Search Report and the Written Opinion dated Jun. 19, 2017 From the International Searching Authority Re. Application No. PCT/IL2017/050132. (20 Pages).
Notice Of Allowance dated Sep. 18, 2017 From the US Patent and Trademark Office Re. U.S. Appl. No. 15/015,208. (25 pages).
Notice of Reasons for Refusal dated May 16, 2018 From the Japan Patent Office Re. Application No. 2016-532782 and Its Translation Into English. (10 Pages).
Office Action dated Dec. 27, 2017 From the Israel Patent Office Re. Application No. 243944 and Its Translation Into English. (6 Pages).
Official Action dated May 4, 2017 From the US Patent and Trademark Office Re. U.S. Appl. No. 15/015,208. (26 pages).
Official Action dated Sep. 18, 2018 From the US Patent and Trademark Office Re. U.S. Appl. No. 15/796,811. (19 Pages).
Request for Examination dated Mar. 29, 2018 From the ROSPATENT, Federal Government Institution, Federal Institute of Industrial Property of the Federal Service for Intellectual Property, Patents and Trademarks of the Russian Federation Re. Application No. 2016106583. (4 Pages).
Supplementary European Search Report and the European Search Opinion dated Apr. 11, 2017 From the European Patent Office Re. Application No. 14834903.8. (15 Pages).

Figure 7:
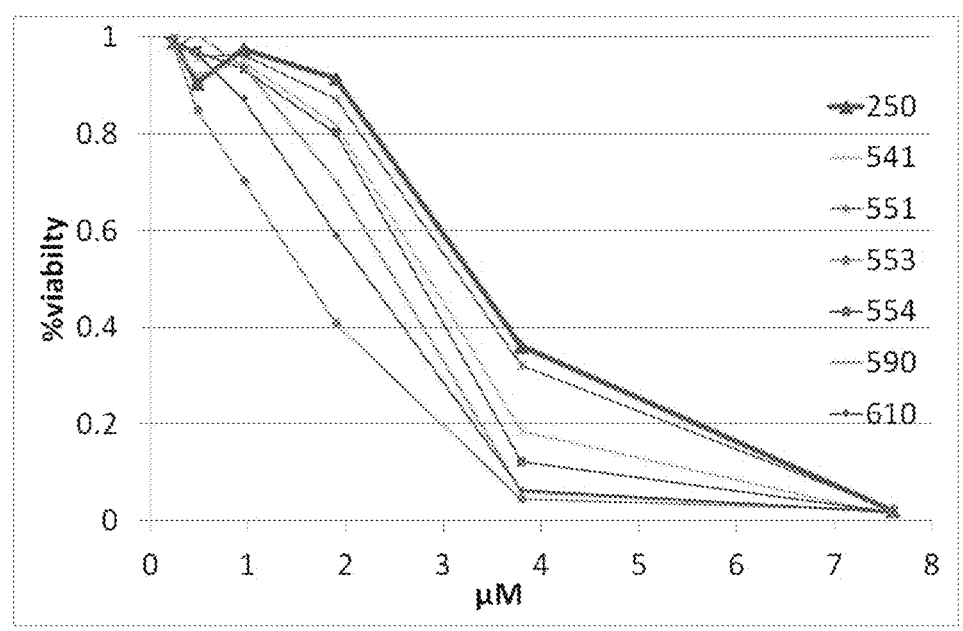

Translation dated Apr. 24, 2018 of Request for Examination dated Mar. 29, 2018 From the ROSPATENT, Federal Government Institution, Federal Institute of Industrial Property of the Federal Service for Intellectual Property, Patents and Trademarks of the Russian Federation Re. Application No. 2016106583. (2 Pages).
Friedler et al. "A Peptide That Binds and Stabilizes P53 Core Domain: Chaperone Strategy for Rescue of Oncogenic Mutants", Proc. Natl. Acad. Sci. USA, PNAS, XP002257716, 99(2): 937-942, Jan. 22, 2002.
Friedler et al. "Binding of Rad51 and Other Peptide Sequences to A Promiscuous, Highly Electrostatic Binding Site in P53", The Journal of Biological Chemistry, XP055339957, 280(9): 8051-8059, Mar. 4, 2005.
Hupp et al. "Small Peptides Activate the Latent Sequence-Specific DNA Binding Function of P53", Cell, XP002003077, 83(2): 237-245, Oct. 20, 1995. Fig.7.
Issaeva et al. "Rescue of Mutants of the Tumor Suppressor P53 in Cancer Cells by A Designed Peptide", Proc. Natl. Acad. Sci. USA, PNAS, 100(23): 13303-13307, Nov. 11, 2003.
Madhumalar et al. "Dimerization of the Core Domain of the P53 Family: A Computational Study", Cell Cycle, XP002768956. 8(1): 137-148, Published Online Jan. 1, 2009. Abstract, Fig.1.
NCBI "Cell Cycle Checkpoint Control Protein RAD9A", UniProtKB/Swiss-Prot: Database [Online], GenBank Accession No. Q99638.1, Database Accession No. Q99638, 12 P., Mar. 7, 2006.
NCBI "Hypothetical Protein MLP_53520 [Microlunatus Phosphovorus NM-1]", UNIPROT Database [Online], GenBank Accession No. BAK38366.1, Database Accession No. BAK38366, 2 P., May 20, 2011.
Petty et al. "An Induced Fit Mechanism Regulates P53 DNA Binding Kinetics to Confer Sequence Specificity", The EMBO Journal, XP055361536, 30(11): 2167-2189, Published Online Apr. 26, 2011. Abstract, Fig.4.
Qiu et al. "A Small Peptide Derived From P53 Linker Region Can Resume the Apoptotic Activity of P53 by Sequestering iASPP With P53", Cancer Letters, XP029105208, 356(2): 910-917, 2014. Abstract, Fig. 1.
Selivanova et al. "Reactivation of Mutant p53 Through Interaction of A C-Terminal Peptide with the Core Domain", Molecular and Cellular Biology,19(5): 3395-3402, May 1, 1999.
Suad et al. "Structural Basis of Restoring Sequence-Specific DNA Binding and Transactivation to Mutant P53 by Suppressor Mutations", Journal of Molecular Biology, XP025846137, 385(1): 249-265, Available Online Oct. 30, 2008. Abstract.
Wright et al. "Factors Governing Loss and Rescue of DNA Binding Upon Single and Double Mutations in the P53 Core Domain", Nucleic Acids Research, XP055361548, 30(7): 1563-1574, Apr. 2002. Abstract, Tables 1-4.
Translation dated Jan. 26, 2020 of Request for Examination and Search Report dated Dec. 30, 2019 From the Federal Service for Intellectual Property, Federal Government Budgetary Institution, Federal Institute of Industrial Property of the Russian Federation Re. Application No. 2019119609. (2 Pages).
Office Action dated Jan. 14, 2020 From the Israel Patent Office Re. Application No. 268355 and Its Translation Into English. (7 Pages).
Request for Examination and Search Report dated Dec. 30, 2019 From the Federal Service for Intellectual Property, Federal Government Budgetary Institution, Federal Institute of Industrial Property of the Russian Federation Re. Application No. 2019119609. (7 Pages).
Notice Of Allowance dated Jan. 31, 2019 From the US Patent and Trademark Office Re. U.S. Appl. No. 15/796,811. (12 pages).
Notification Regarding Patentability dated Nov. 20, 2018 From the ROSPATENT, Federal Government Institution, Federal Institute of Industrial Property of the Federal Service for Intellectual Property, Patents and Trademarks of the Russian Federation Re. Application No. 2016106583. (4 Pages).
Notification of Office Action and Search Report dated May 29, 2019 From the National Intellectual Property Administration of the People's Republic of China Re. Application No. 201480053550.8 and Its Translation Into English. (17 Pages).
Translation dated Jan. 11, 2018 of Notification Regarding Patentability dated Nov. 20, 2018 From the ROSPATENT, Federal Gov-

(56) References Cited

OTHER PUBLICATIONS ernment Institution, Federal Institute of Industrial Property of the Federal Service for Intellectual Property, Patents and Trademarks of the Russian Federation Re. Application No. 2016106583. (2 Pages).
Request for Examination and Search Report dated Jun. 25, 2020 From the Federal Government Institution, Federal Institute of Industrial Property of the Federal Service of Intellectual Property, Patents and Trademarks of the Russian Federation, FIPS Re. Application No. 2018131120 and Its Translation of Request for Examination Into English. (9 Pages).
Chumakov "Protein P53 and Its Universal Functions in A Multicellular Organism", Advances in Biological Chemistry, 47(1): 3-52, 2007. English Abstract.
Vilgelm et al. "The Coordinated Interaction of Multifunctional Members of P53 Family Determines Many Key Processes in Multicellular Organisms", Molecular Biology, 45(1): 180-197, 2011. English Abstract.
Communication Pursuant to Article 94(3) EPC dated May 19, 2020 From the European Patent Office Re. Application No. 17706901.0. (11 Pages).
Official Action dated Apr. 17, 2020 from the US Patent and Trademark Office Re. U.S. Appl. No. 16/340,137. (13 pages).
GenBank "NADH Dehydrogenase Subunit 61 Partial (Mitochondrion) [Capra hircus]", GenBank: AFJ 15095.1, published May 12, 2012, 1 page.
Ben-Shimon and Niv (2015) AnchorDock: Blind and Flexible Anchor-Driven Peptide Docking. Structure 23(5): 929-940.
Bian et al., (2007) Effect of Cell-Based Intercellular Delivery of Transcription Factor GATA4 on Ischemic Cardiomyopathy. Circulation Research 100:1626-1633.
Bykov et al., (2005) Reactivation of mutant p53 and induction of apoptosis in human tumor cells by maleimide analogs J Biol Chem 280(34): 30384-30391 with erratum.
Dimri et al., (1995) A biomarker that identifies senescent human cells in culture and in aging skin in vivo. Proc Natl Acad Sci U S A 92(20): 9363-9367.
Fawell et al., (1994) Tat-mediated delivery of heterologous proteins into cells. Proc Natl Acad Sci U S A 91(2): 664-668.
Foster et al., (1999) Pharmacological rescue of mutant p53 conformation and function. Science 286(5449): 2507-2510.
Grellety et al., (2015) PRIMA-1(MET) induces death in soft-tissue sarcomas cell independent of p53. BMC Cancer 15:684; 8 pages.
Joerger et al., (2004) Crystal structure of a superstable mutant of human p53 core domain. Insights into the mechanism of rescuing oncogenic mutations. J Biol Chem 279(2): 1291-1296.
Mohell et al., (2015) APR-246 overcomes resistance to cisplatin and doxorubicin in ovarian cancer cells. Cell Death Dis 6(6): e1794; 11 pages.
Peng et al., (2003) Rescue of mutant p53 transcription function by ellipticine. Oncogene 22(29): 4478-4487.
Rippin et al., (2002) Characterization of the p53-rescue drug CP-31398 in vitro and in living cells. Oncogene 21(14):2119-2129.
Samuels-Lev et al., (2001) ASPP proteins specifically stimulate the apoptotic function of p53. Mol Cell 8(4): 781-794.
Théodore et al., (1995) Intraneuronal delivery of protein kinase C pseudosubstrate leads to growth cone collapse. J Neurosci 15(11): 7158-7167.
Ventura et al., (2007) Restoration of p53 function leads to tumour regression in vivo. Nature 445(7128): 661-665.
Wong et al., (1999) Hot-spot mutants of p53 core domain evince characteristic local structural changes. Proc Natl Acad Sci U S A 96(15): 8438-8442.
Notice of Reasons for Refusal dated Jun. 23, 2020 From the Japan Patent Office Re. Application No. 2019-125644 and Its Translation Into English. (7 Pages).
Arnau et al., (2006) Current strategies for the use of affinity tags and tag removal for the purification of recombinant proteins. Protein Expr Purif 48(1): 1-13.
Buczek et al., (2005) Post-translational amino acid isomerization: a functionally important D-amino acid in an excitatory peptide. J Biol Chem 280(6): 4247-4253.
Chen et al., (2013) Fusion protein linkers: property, design and functionality. Adv Drug Deliv Rev. Author manuscript available in PMC Oct. 15, 2014. Published in final edited form as: Adv Drug Deliv Rev 65(10): 1357-1369.
Freed-Pastor and Prives (2012) Mutant p53: one name, many proteins. Genes Dev 26(12): 1268-1286.
Heitz et al., (2009) Twenty years of cell-penetrating peptides: from molecular mechanisms to therapeutics. Br J Pharmacol 157(2): 195-206.
Kandoth et al., (2013) Mutational landscape and significance across 12 major cancer types. Nature 502(7471) 333-339.
Liu et al., (2014) Cell-penetrating peptide-mediated delivery of TALEN proteins via bioconjugation for genome engineering. PLoS One 9(1): e85755; 7 pages.
Maeda et al., (1997) Engineering of functional chimeric protein G-Vargula luciferase. Anal Biochem 249(2): 147-152. Abstract.
Pakula and Sauer (1989) Genetic analysis of protein stability and function. Annu Rev Genet 23: 289-310.
Soussi and Wiman (2015) TP53: an oncogene in disguise. Cell Death Differ 22(8): 1239-1249.
Tsao et al., (2007) Prognostic and predictive importance of p53 and RAS for adjuvant chemotherapy in non small-cell lung cancer. J Clin Oncol 25(33): 5240-5247.
Zhao and Weissleder (2004) Intracellular cargo delivery using tat peptide and derivatives. Med Res Rev 24(1): 1-12. Abstract.
Xu et al., (2012) Effects of the residue mutations on the segment of p53-DNA binding region based on molecular dynamics simulation Acta Physico-Chimica Sinica 28(7): 1665-1675. Abstract.

\* cited by examiner

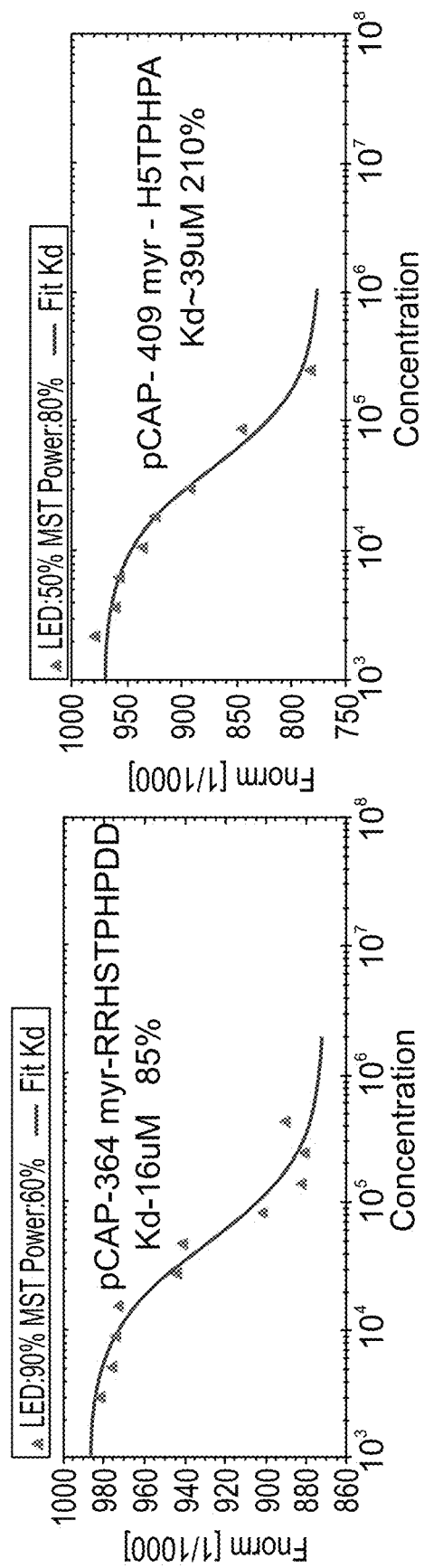

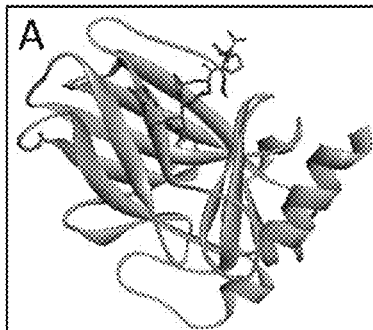
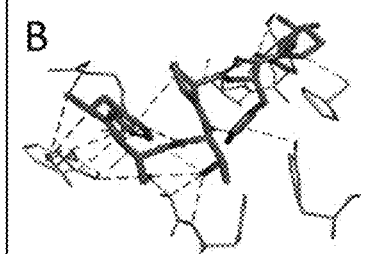
FIG. 6A
FIG. 6B
FIG. 6C
FIG. 6 (Continued 1)

FIG. 6 (Continued 2)

PEPTIDES AND USE OF SAME IN THE TREATMENT OF DISEASES, DISORDERS OR CONDITIONS ASSOCIATED WITH A MUTANT P53

RELATED APPLICATIONS

This application is a National Phase of PCT Patent Application No. PCT/IL2017/050132 having International filing date of Feb. 3, 2017, which claims the benefit of priority under 35 USC § 119(e) of U.S. Provisional Patent Application No. 62/291,003 filed on Feb. 4, 2016. The contents of the above applications are all incorporated by reference as if fully set forth herein in their entirety.

SEQUENCE LISTING STATEMENT

The ASCII file, entitled 74543SequenceListing.txt, created on Jul. 31, 2018, comprising 115,276 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to peptides and use of same in the treatment of diseases, disorders or conditions associated with a mutant p53.

Cancer is a leading cause of death in developed countries, and as the average age of the population continues to rise, so do the numbers of diagnosed cases and economic implications. Cancer is not a single disease, but rather a group of more than 200 diseases characterized by uncontrolled growth and spread of abnormal cells. Cancer is a highly heterogeneous disease with major molecular differences in the expression and distribution of tumor cell surface markers even among patients with the same type and grade of cancer. Moreover, cellular mutations tend to accumulate as cancer progresses, further increasing tumor heterogeneity. Most tumor cells exhibit genomic instability with an increased expression of oncogenes and inactivation of tumor suppressor genes.

The p53 gene is considered to be the most important tumor suppressor gene that acts as a major barrier against cancer progression. The p53 protein responds to various types of cellular stress, and triggers cell cycle arrest, apoptosis, or senescence. This is achieved by transcriptional transactivation of specific target genes carrying p53 DNA binding motifs. It is widely agreed that the p53 pathway is impaired in almost all human cancers. Mutation of p53 is viewed as a critical step in malignant transformation process and over 50% of cancer cases carry mutations in their p53 genes. Most of these mutations are missense point mutations that target the DNA-binding core domain (DBD) of p53, thereby abolishing specific DNA binding of p53 to its target site. These mutations prevent p53-dependent transcription and consequently p53-mediated tumor suppression. The exceptionally high frequency of p53 mutations in human tumors of diverse types makes p53 unique among genes involved in tumor development, rendering mutated p53 (Mut-p53) an attractive target for novel cancer therapies.

Structural studies have revealed that the tumor-derived missense mutations in the DBD of p53 produce a common effect: destabilization of DBD folding at physiological temperature (Joerger, A. C., M. D. Allen, and A. R. Fersht, *Crystal structure of a superstable mutant of human p53 core domain. Insights into the mechanism of rescuing oncogenic mutations*. J Biol Chem, 2004 279(2): p. 1291-6). This destabilization may be reversible, since some mutants can revert to wild-type conformation and bind DNA at reduced temperatures. Thus, most mutations of p53 destabilize p53 protein folding, causing partial denaturation at physiological temperature.

Mutant p53 proteins accumulate at high levels in tumor cells, mainly due to their inability to upregulate the expression of p53's own destructor Mdm2. Moreover, many p53 activating stress signals (like hypoxia, genomic instability and oncogene expression) are constitutively induced in cancer cells. Therefore, reactivation of Mut-p53 is expected to exert major anti-tumor effects. Furthermore, it has been shown in a mouse model that restoration of p53 functions is well tolerated in normal tissues and produces no visible toxic effects (Ventura, A., et al., Restoration of p53 function leads to tumour regression in vivo. Nature, 2007. 445(7128): p. 661-5).

Structural studies show that the extent of misfolding differs among mutants; however, there is no defined alternative fold but rather a partial denaturation. This suggests that a "small molecule' approach to reverse the effect of p53 mutation on folding could be applicable to a wide range of mutant forms. Another important prediction from structural studies is that a ligand that binds to the properly folded fraction of the protein is expected to shift the equilibrium towards the native fold according to the law of mass action.

Several correctional approaches were attempted in the p53 conformation field. Proof of principle for conformation stabilizing peptides was provided by Friedler and colleagues (Friedler, A., et al., *A peptide that binds and stabilizes p53 core domain: chaperone strategy for rescue of oncogenic mutants*. Proc. Natl. Acad. Sci. USA, 2002. 99(2): p. 937-42). A nine-residue peptide, CDB3, was designed based on the crystal structure of the complex between the p53 DBD and ASPP (Samuels-Lev, Y., et al., *ASPP proteins specifically stimulate the apoptotic function of p53*. Mol. Cell, 2001. 8(4): p. 781-94). This peptide was shown to bind Mut-p53 and act as a chaperone, shifting equilibrium towards the WT conformation, as indicated by increased reactivity to PAb1620. However, the biological effects of CDB3 (Issaeva, N., et al., *Rescue of mutants of the tumor suppressor p53 in cancer cells by a designed peptide*. Proc. Natl. Acad. Sci. USA, 2003. 100(23): p. 13303-7) are only partial since the conformation of the Mut-p53/CDB3 complex is in an intermediate state between WT and mutant.

Small molecule compounds targeting Mut-p53 have been identified using either protein-based or cell-based assays (Peng, Y., et al., *Rescue of mutant p53 transcription function by ellipticine*. Oncogene, 2003. 22(29): p. 4478-87). CP-31398 was identified by screening for molecules that protect the isolated p53 DBD from thermal denaturation, as assessed by maintenance of PAb1620 reactivity upon protein heating (Foster, B. A., et al., *Pharmacological rescue of mutant p53 conformation and function*. Science, 1999. 286 (5449): p. 2507-10). The mechanism of action of CP-31398 remains unclear. NMR studies failed to detect any binding of CP-31398 to the p53 DBD (Rippin, T. M., et al., *Characterization of the p53-rescue drug CP-31398 in vitro and in living cells*. Oncogene, 2002. 21(14): p. 2119-29). CP-31398 affects gene expression and induces cell death both in a p53-dependent and independent manner. Thus, it appears that CP-3138 has other cellular targets than p53 that may account for its cellular toxicity.

Two other small molecules that rescue p53 function in living cancer cells, PRIMA-1 and MIRA-1, were discovered by using cell-based screening assays. PRIMA-1 and MIRA-1 have similar activity profiles (Bykov, V. J., et al., *Reactivation of mutant p53 and induction of apoptosis in human tumor cells by maleimide analogs.* J Biol Chem, 2005. 280(34): p. 30384-91), but are structurally unrelated. PRIMA-1 is a pro-drug, which is converted into an active compound that binds to mutant p53 but also to other molecules (Cell Death Dis. 2015 Jun. 18; 6:e1794. doi: 10.1038/cddis.2015.143), and some of its effects appear to be independent of mutant p53 status (BMC Cancer. 2015 Oct. 13; 15:684. doi: 10.1186/s12885-015-1667-1).

Inventors of some embodiments of the invention have previously described the use of phage display to select mutp53-reactivating peptides (WO2015/019318). Phage peptide display libraries have a much higher complexity than chemical libraries. The selection process was based on binding of peptides to an immobilized target, elution and amplification and finally identification by sequencing, enabling screening of high numbers of molecules in a short time. Different selection strategies were combined to select leads from different peptide libraries and deep sequencing of selected pools. Lead peptides were shown to endow mutp53 with WTp53-like activities in vitro and in live cells, and cause regression of mutp53-bearing tumors in several xenograft models.

SUMMARY OF THE INVENTION

According to an aspect of some embodiments of the present invention there is provided an isolated peptide comprising an amino acid sequence arranged in a space and configuration that allow interaction of the peptide with the DNA Binding Domain (DBD) of p53 through at least one residue of the DBD by which pCAP 250 (SEQ ID NO: 1) binds the DBD, wherein the peptide at least partially reactivates a mutant p53 protein, with the proviso that the peptide is not SEQ ID NO: 59-382.

According to some embodiments of the invention, the interaction is via Helix-2 and L1 of the DBD.

According to some embodiments of the invention, the interaction affects the structural stability of Helix-2 and/or L1 of the DBD, as assayed by NMR.

According to some embodiments of the invention, the at least one residue is selected from the group consisting of H115, G117 of L1 and Y126 and V274 and G279 and R280 of the p53.

According to some embodiments of the invention, the interaction is by at least one amino acid of the amino acid sequence.

According to some embodiments of the invention, the interaction is by at least two amino acids of the amino acid sequence.

According to some embodiments of the invention, the interaction is by at least three amino acids of the amino acid sequence.

According to some embodiments of the invention, the interaction is by at least four amino acids of the amino acid sequence.

According to some embodiments of the invention, the peptide comprises an amino acid sequence of:

$$X_1-X_2-X_3-X_4-X_5-X_6 \quad \text{(SEQ ID NO: 53)}$$

wherein, $X_1$ and $X_5$ are a positively charged amino acid;

$X_2$ is selected from the group consisting of Ser, Thr, Asn, Gln, Pro, Ala and Gly;

$X_3$ is any amino acid;

$X_4$ and $X_6$ are selected from the group consisting of an alpha methyl amino acid and a beta breaker amino acid.

According to some embodiments of the invention, the peptide comprises an amino acid sequence of:

$$X_1-X_2-X_3-X_4-X_5-X_6 \quad \text{(SEQ ID NO: 54)}$$

wherein, $X_1$ and $X_5$ are selected from the group consisting of His, Arg and Lys;

$X_2$ is selected from the group consisting of Ser, Thr, Asn, Gln, Pro, Ala and Gly;

$X_3$, $X_4$, $X_6$ is any amino acid.

According to some embodiments of the invention, the positively charged amino acid is selected from the group consisting of His, Diaminobutyric acid (Dab), Arg and Lys.

According to some embodiments of the invention, the $X_3$ is a D-amino acid.

According to some embodiments of the invention, the $X_3$ is a phosphorylated amino acid.

According to some embodiments of the invention, $X_3$ is a non-phosphorylatable amino acid.

According to some embodiments of the invention, the $X_3$ is a non-hydrogen bonding amino acid.

According to some embodiments of the invention, the $X_3$ is selected from the group consisting of polar uncharged amino acid and a hydrophobic amino acid.

According to some embodiments of the invention, the $X_2$ is Ser.

According to some embodiments of the invention, the $X_4$ is alpha methyl amino acid and $X_6$ is alanine.

According to some embodiments of the invention, the isolated peptide has the amino acid sequence HSAPHP (SEQ ID NO: 49) or HSEPHP (SEQ ID NO: 50).

According to some embodiments of the invention, the isolated peptide comprises at least one additional amino acid ($X_7$) attached to the C-terminus of the amino acid sequence.

According to some embodiments of the invention, the at least one additional amino acid is a negatively charged amino acid.

According to some embodiments of the invention, the at least one additional amino acid is selected from the group consisting of Asp, Glu, Gly, Ala and Ser.

According to some embodiments of the invention, the at least one additional amino acid comprises two additional amino acids ($X_7$-$X_8$) and wherein the $X_8$ is selected from the group consisting of His, Dab, Asp and Glu.

According to some embodiments of the invention, the isolated peptide comprises at least one additional amino acid attached to the N-terminus of the amino acid sequence.

According to some embodiments of the invention, the isolated peptide comprises at least two additional amino acids attached to the N-terminus of the amino acid sequence.

According to some embodiments of the invention, the at least one additional amino acid attached to the N-terminus of the amino acid sequence is Arg.

According to some embodiments of the invention, the isolated peptide further comprises a cell penetrating moiety.

According to some embodiments of the invention, the cell penetrating moiety is attached to an N-terminus of the peptide.

According to some embodiments of the invention, the cell penetrating moiety is selected from the group consisting of a fatty acid moiety, a proteinaceous moiety and a combination of same.

According to some embodiments of the invention, the fatty acid moiety comprises a myristoyl fatty acid and the proteinaceous moiety comprises at least one positively charged amino acid.

According to some embodiments of the invention, the isolated peptide is no longer than 20 amino acids in length.

According to some embodiments of the invention, the peptide at least partially changes the conformation of the mutant p53 protein to a conformation of a wild-type (WT) p53 protein.

According to some embodiments of the invention, the peptide at least partially changes the conformation of the mutant p53 protein such that the mutant p53 protein is recognized by a monoclonal antibody directed against a WT p53 protein.

According to some embodiments of the invention, the mutant p53 protein is not recognized by a monoclonal antibody directed against a WT p53 protein.

According to some embodiments of the invention, the mutant p53 protein, upon binding to the peptide, is recognized by a monoclonal antibody directed against a WT p53 protein.

According to some embodiments of the invention, the monoclonal antibody is Ab1620.

According to some embodiments of the invention, the peptide at least partially restores the activity of the mutant p53 protein to the activity of a WT p53 protein.

According to some embodiments of the invention, the activity is reducing viability of cells expressing the mutant p53 protein.

According to some embodiments of the invention, the activity is promoting apoptosis of cells expressing the mutant p53 protein.

According to some embodiments of the invention, the activity is binding to a p53 consensus DNA binding element in cells expressing the mutant p53 protein.

According to some embodiments of the invention, the consensus DNA binding element comprises the nucleic acid sequences set forth in SEQ ID NO: 55 and 56).

According to some embodiments of the invention, the binding results in at least partial activation of an endogenous p53 target gene.

According to some embodiments of the invention, the endogenous target gene is selected from the group consisting of p21, MDM2 and PUMA.

According to some embodiments of the invention, the mutant p53 protein is of a different conformation than a WT p53 protein.

According to some embodiments of the invention, the isolated peptide is as set forth in SEQ ID NO: 429 or 448.

According to some embodiments of the invention, the isolated peptide is as set forth in SEQ ID NO: 429, 448, 446, 449 or 462.

According to some embodiments of the invention, the isolated peptide is selected from the group consisting of SEQ ID NO: 8 and 412-464.

According to some embodiments of the invention, the isolated peptide is not any of the peptides set forth in SEQ ID NOs: 59-382.

According to an aspect of some embodiments of the present invention there is provided a method of treating a disease, disorder or condition associated with a mutant p53 protein, comprising administering to a subject in need thereof a therapeutically effective amount of the isolated peptide of as described herein, thereby treating the disease, disorder or condition.

According to some embodiments of the invention, the method further comprises administering to the subject a therapeutically effective amount of a platinum-based chemotherapy.

According to an aspect of some embodiments of the present invention there is provided a method of treating a disease, disorder or condition associated with a mutant p53 protein, comprising administering to a subject in need thereof a therapeutically effective amount of a platin-based chemotherapy and an isolated peptide comprising an amino acid sequence having a space and configuration that allow binding of the peptide to the DNA Binding Domain (DBD) of p53 in the same mode as pCAP 250 (SEQ ID NO: 1) binds the DBD, wherein the peptide at least partially reactivates a mutant p53 protein, thereby treating the disease, disorder or condition.

According to an aspect of some embodiments of the present invention there is provided a method of treating a disease, disorder or condition associated with a mutant p53 protein, comprising administering to a subject in need thereof a therapeutically effective amount of an isolated peptide comprising an amino acid sequence having a space and configuration that allow binding of the peptide to the DNA Binding Domain (DBD) of p53 in the same mode as pCAP 250 (SEQ ID NO: 1) binds the DBD, wherein the peptide at least partially reactivates a mutant p53 protein and wherein the therapeutically effective amount is 0.01-0.3 mg/kg per day, thereby treating the disease, disorder or condition.

According to some embodiments of the invention, the peptide is the peptide as described herein.

According to some embodiments of the invention, the peptide is pCAP 250 (SEQ ID NO: 1).

According to some embodiments of the invention, the administering comprises subcutaneous administering.

According to some embodiments of the invention, the administering comprises continuous infusion.

According to some embodiments of the invention, the disease is cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a dose response of pCAP-250 (SEQ ID NO: 1) alone or in combination with Cisplatin in viability assay of ES2 ovarian cancer cells. Cells were cultured in 96 wells plates with 3000 cells/well. Serial dilutions of pCAP-250 were added either alone or together with 1 μg/ml of cisplatin and the plates incubated for additional 48 h at 37° C. Then medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm. The viability of ES2 cells treated with 1 μg/ml was 39%. The IC50 for pCAP-250 was estimated at 3.2 μM and in combination with cisplatin the IC50 for pCAP-250 was estimated at 1.9 μM indicating a synergistic effect between the two compounds.

Figure 2:
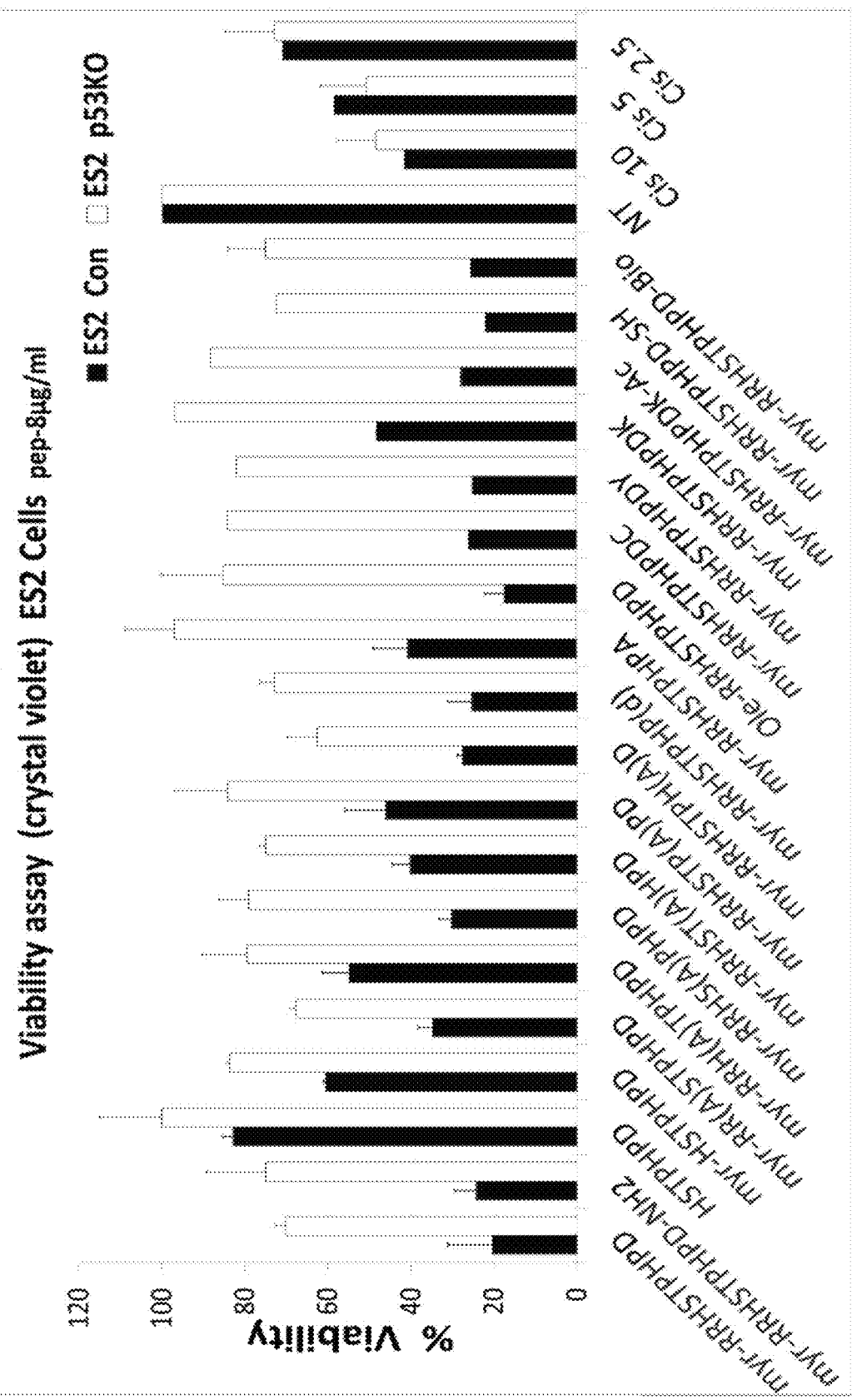
Figure 3A:
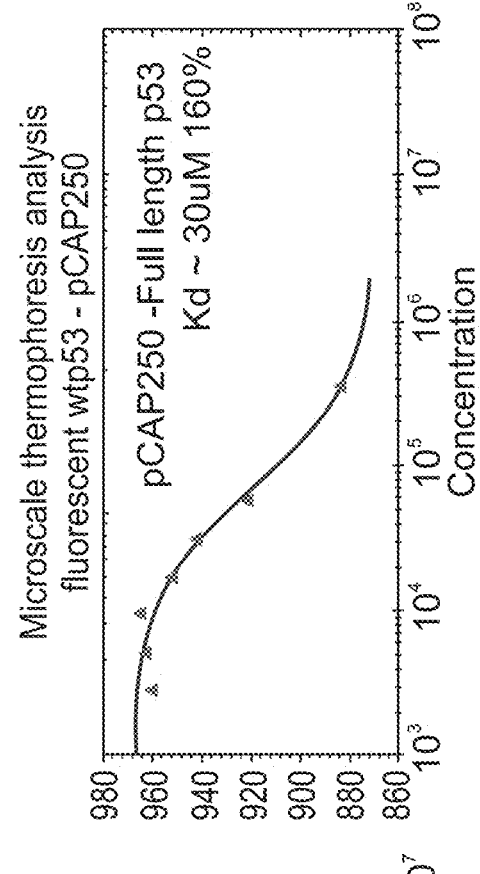
Figure 3B:
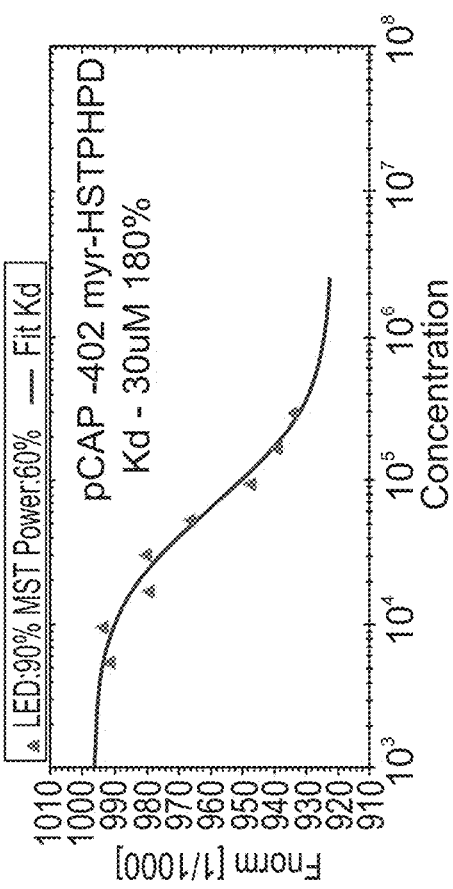
Figure 3C:
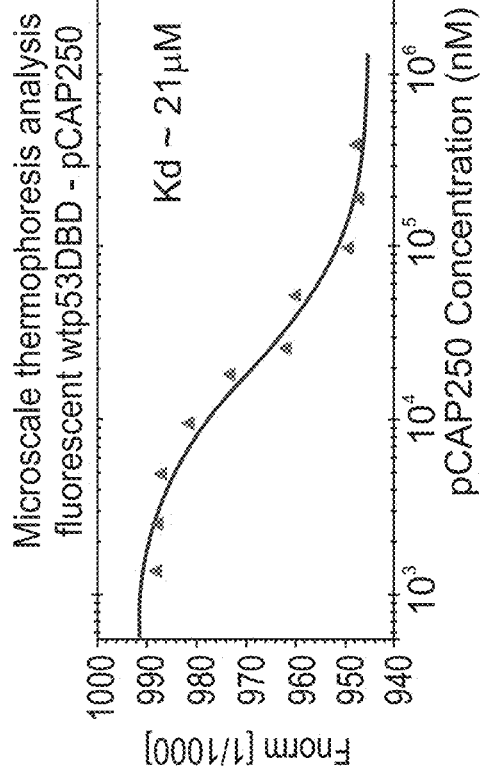
Figure 3D:
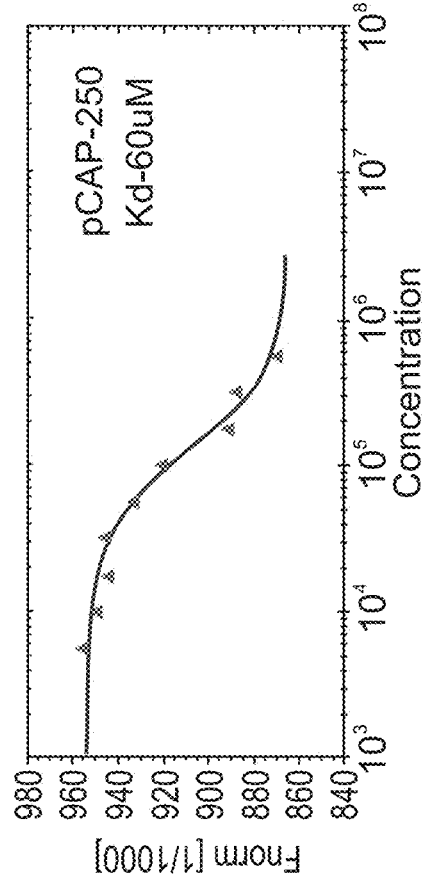
Figure 3E:
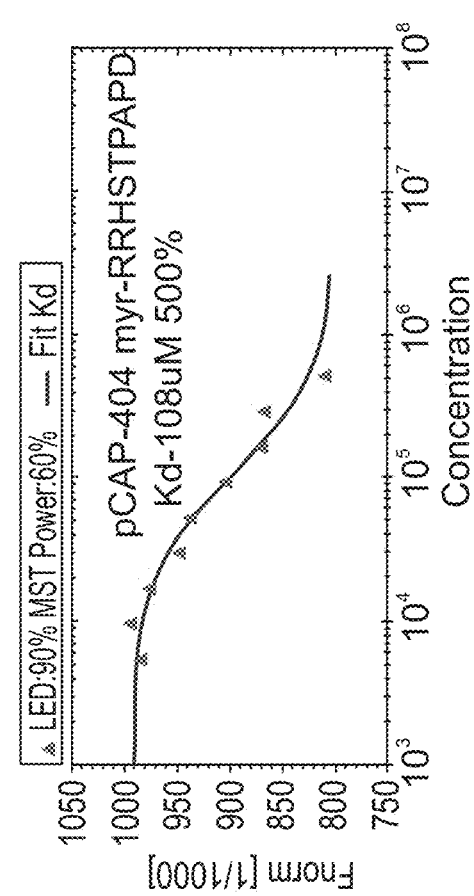
Figure 3F:
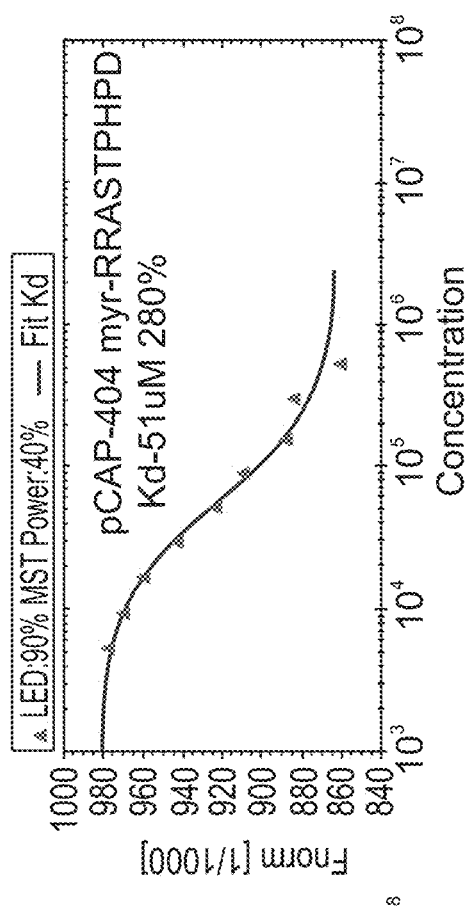
Figure 3G:
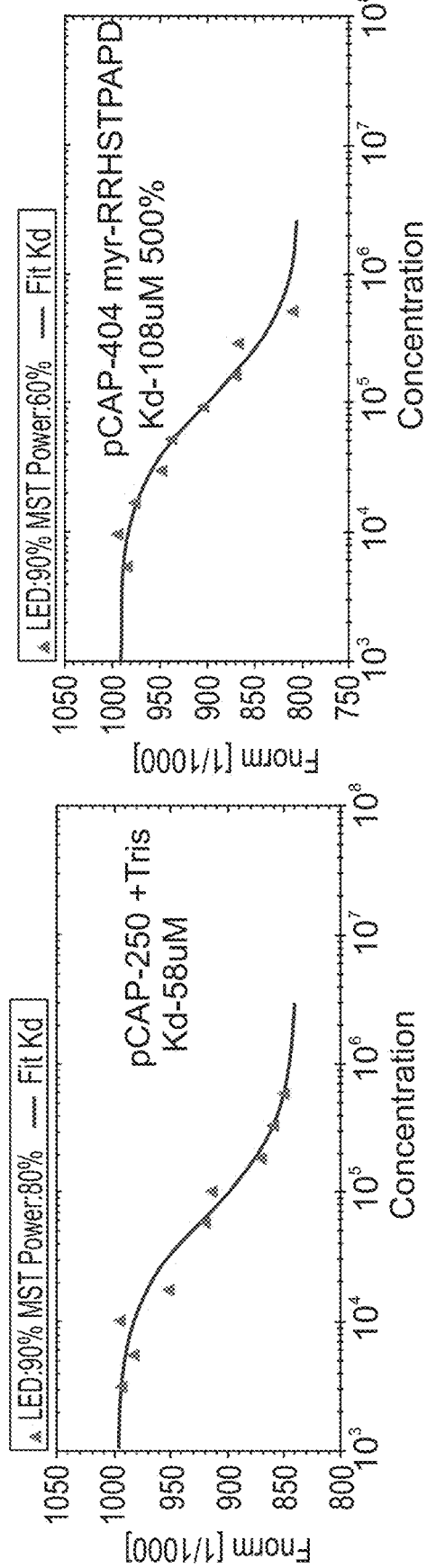
Figure 3H:
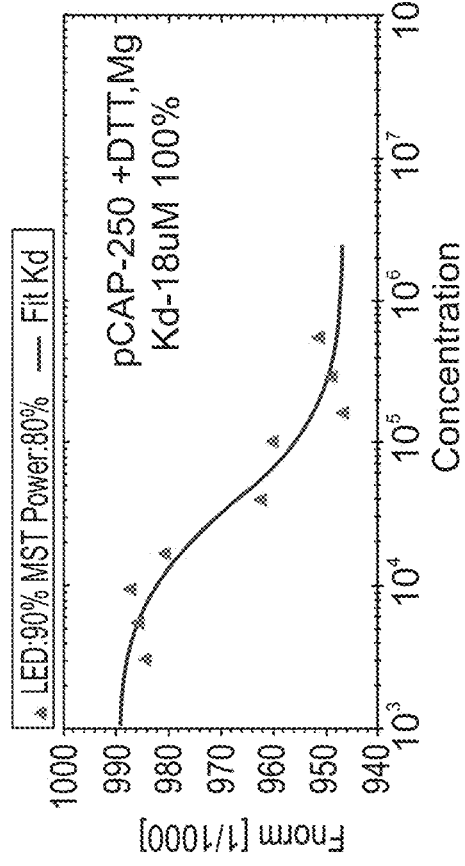

FIG. 2 is a bar graph showing the effect of pCAP-250 (SEQ ID NO: 1) and different derivatives (SEQ ID NOs: 2-19) in viability assay of ES2 ovarian cancer cells and on binding to p53 DBD as determined by MST. Cells, ES2 Con expressing endogenous mp53$^{S241F}$, and ES2 KO cells in which p53 was stably knocked out using CRISPR/Cas9 (ES2 p53KO), to control for specificity for mutp53 were cultured in 96 wells plates with 3000 cells/well. Indicated peptides were added at a concentration of 8 μg/ml and the plates incubated for additional 48 h at 37° C. Then medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm. The difference in the effect of a particular peptide for ES2 Con compared to ES KO indicates specificity of peptide to mutp53 expression. Several peptide derivatives in which amino acids that were substituted to Alanine (Serine and Histidine for example) showed a decreased effect on ES2 Con cells indicating the importance of these amino acids for peptide efficacy.

FIGS. 3A-K are graphs of microscale thermophoresis (MST) analysis for the binding of fluorescently labeled WTp53DBD (FIG. 3A) or full length p53 (FIG. 3B) and the indicated peptides (SEQ ID NOs: 1, 4, 9). The experiment was performed according to the manufacturer's instructions; 10 serial dilutions of each indicated peptide; (FIG. 3A—pCAP-250) (FIGS. 3A, F, H, I, K pCAP402, pCAP 404, pCAP409 and pCAP 364) were prepared, labeled protein was added to each peptide sample and loaded to capillaries. The samples were analyzed for movement of fluorescent wtp53DBD in temperature gradient with different concentrations of peptides. MST analysis results are presented as a curve obtained from manufacturer data analysis software.

Figure 4A:
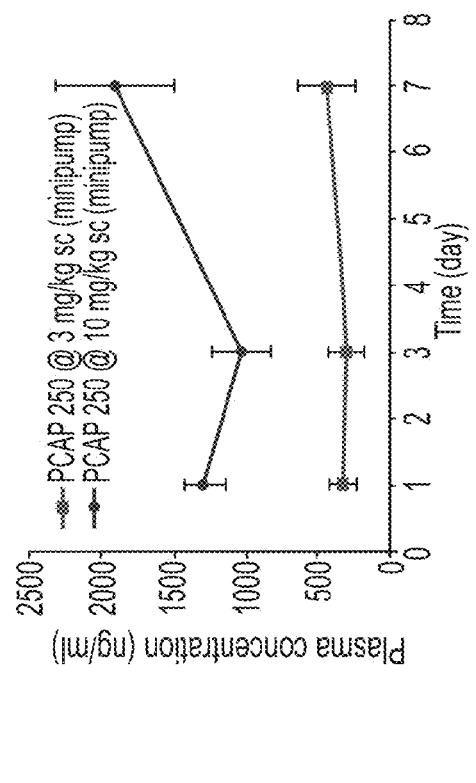
Figure 4C:
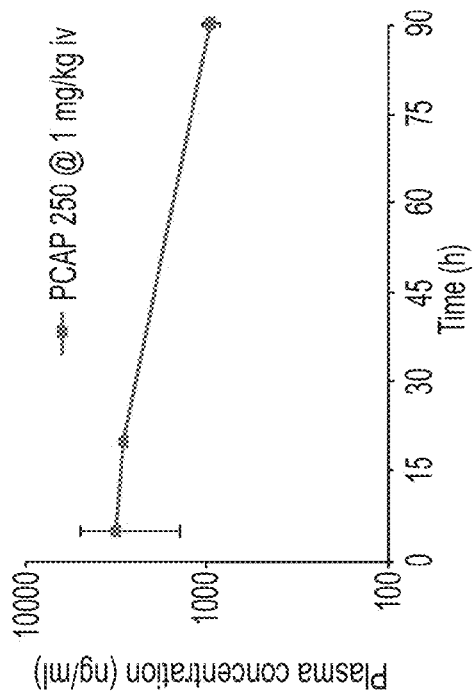
Figure 4B:
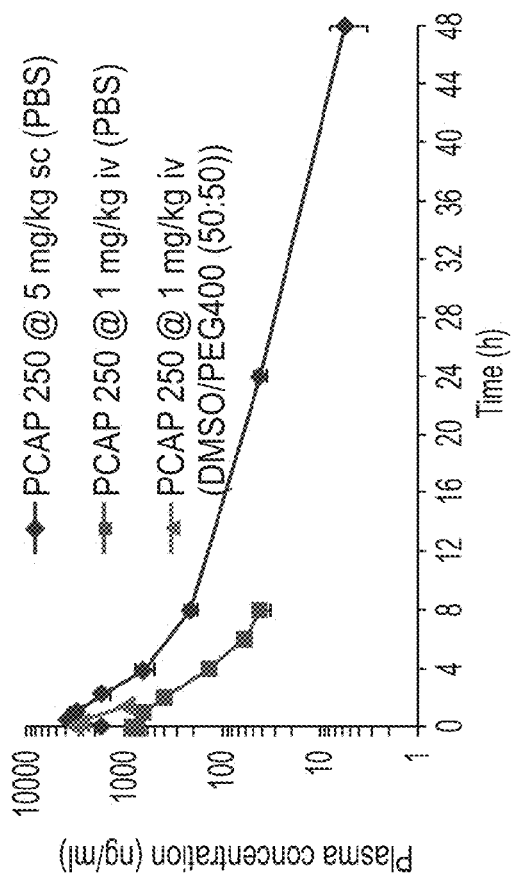
Figure 4D:
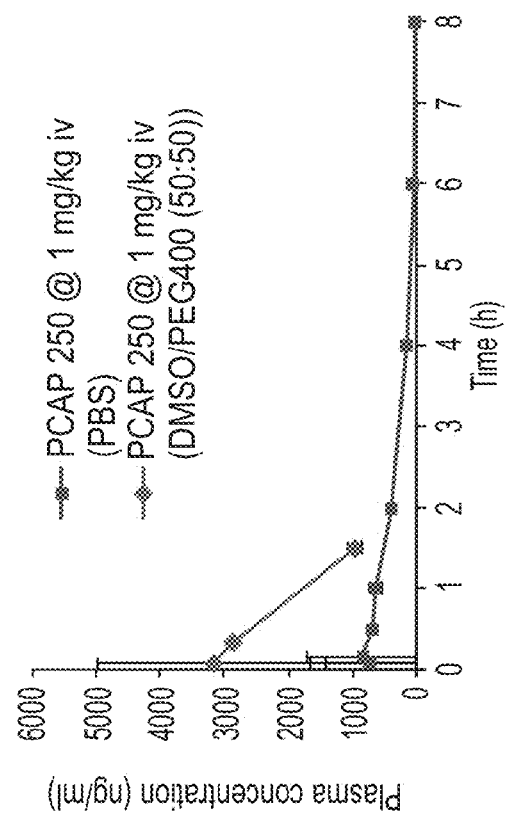

FIGS. 4A-D show the pharmacokinetics of various modes of administration. FIG. 4A—Plasma concentration vs. time profiles of pCAP-250 after administration of 1 mg/kg iv (mean±SD, n=3). FIG. 4B—Plasma concentration vs. time profiles of pCAP-250 after continuous subcutaneous administration for 7 days (mean±SD, n=3). FIG. 4C—Plasma concentration vs. time profiles of pCAP-250 after administration of 1 mg/kg iv (mean±SD, n=3). FIG. 4D—Plasma concentration vs. time profiles of PCAP-250 after subcutaneous administration of 1 mg/kg (mean±SD, n=3).

FIGS. 5A-D In-vivo effect of pCAP-250 peptide in a mouse xenograft model.

Figure 5A:
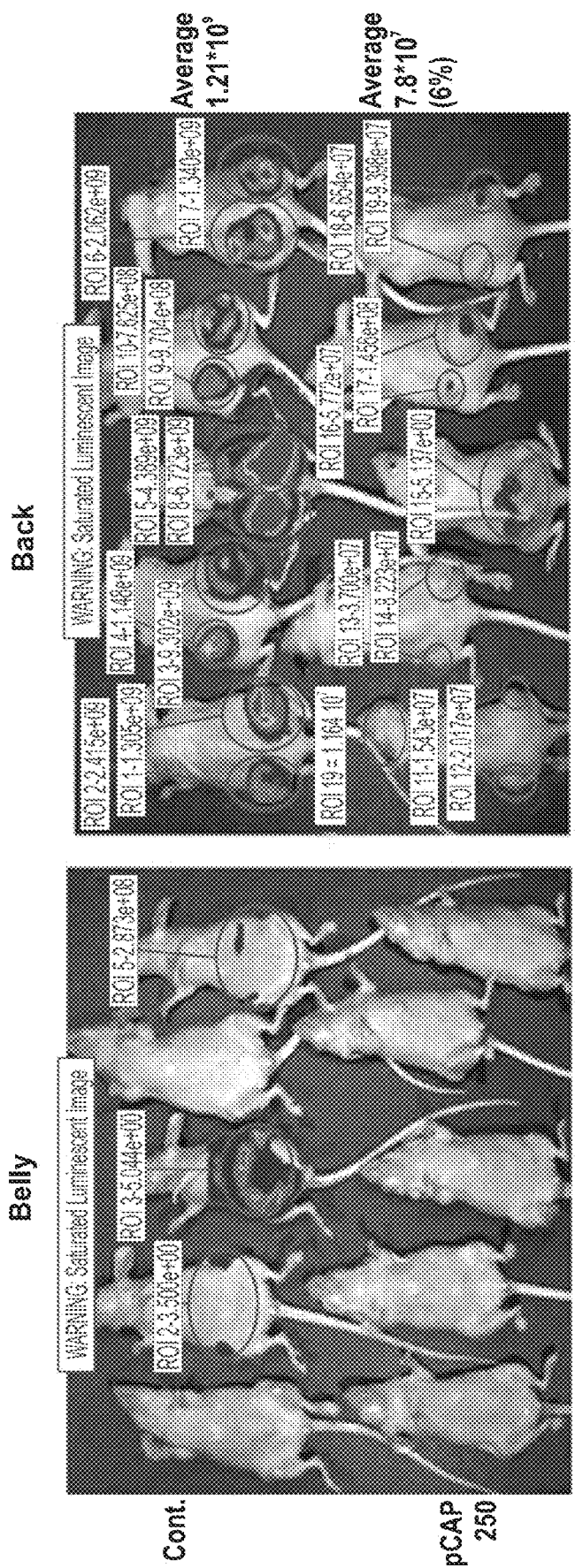
Figure 5B:
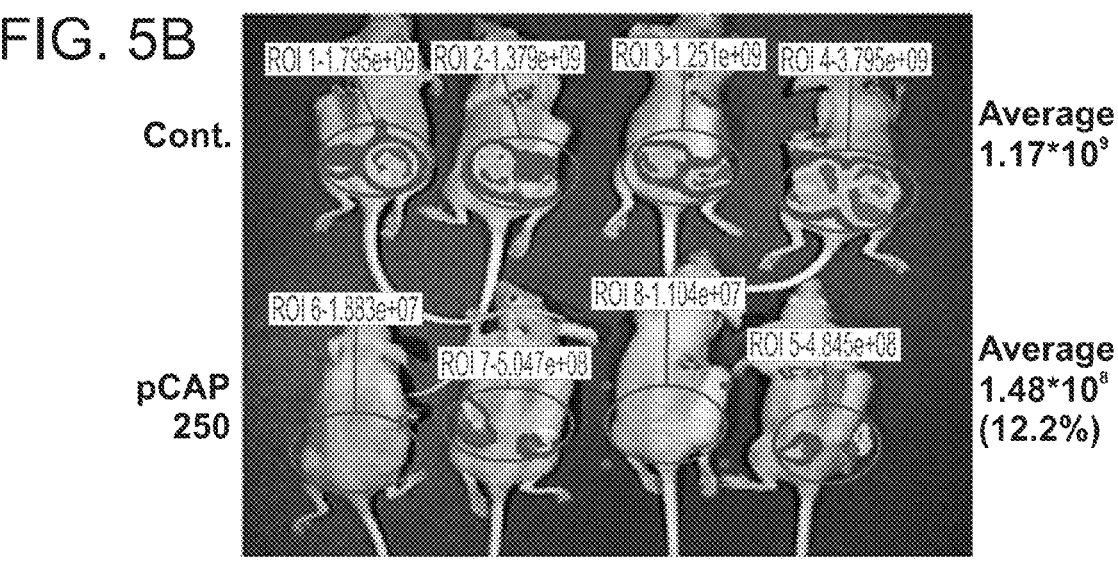
Figure 5C:
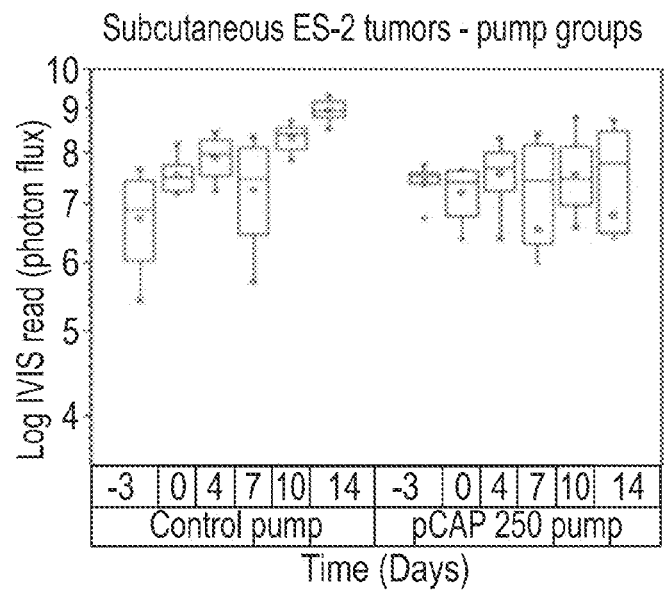
Figure 5D:
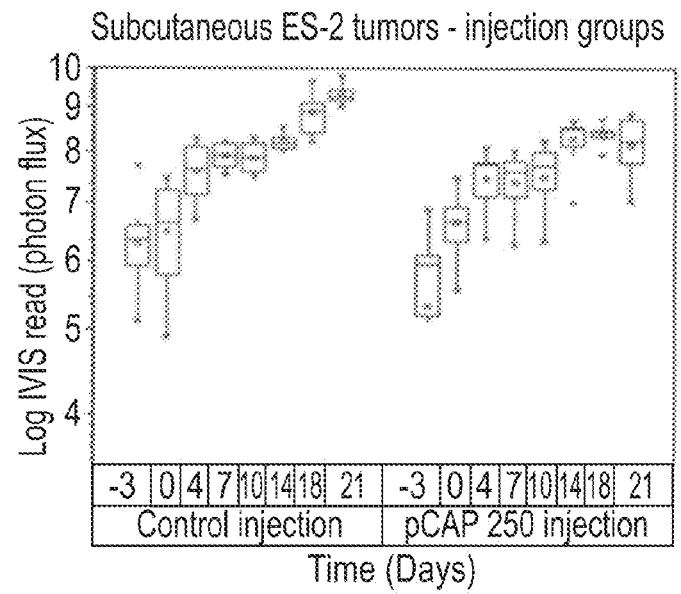

2*10$^5$ ES2 cells expressing luciferase were injected into the hips of nude mice. Bioluminescence was measured. 12 days after injection, mice were randomly divided to 4 groups and either injected intratumorally, three times a week, with a mixture of 2 control peptides (pCAPs 76 and 12; 5 μg of each peptide) or pCAP-250 (10 μg). Alternately, mice were transplanted with Alzet minipumps containing 0.8 mg in PBS control peptides or 0.8 mg in PBS of pCAP-250. FIG. 5A, Live imaging of control group mice and intratumoral pCAP-250 treated mice, at termination of experiment (day 21). FIG. 5B—Live imaging of control group mice and Alzet minipumps pCAP-250 treated mice, at termination of experiment (day 14). FIG. 5C—control mice and effective pCAP-250 group: box-plot showing the luciferase readings in tumors as a function of time; average (horizontal line), standard deviation (box), highest and lowest reads are shown, before (until day 0) and after initiation of treatment. The background threshold detection level of the IVIS system was about 5×10$^6$ photons. FIG. 5D—Control mice and effective pCAP-250 group: box-plot showing the luciferase readings in tumors as a function of time; average (horizontal line), standard deviation (box), highest and lowest reads are shown, before (until day 0) and after initiation of treatment. The background threshold detection level of the IVIS system was about 5×10$^6$ photons.

FIGS. 6A-C show optional predicted peptide binding position for the HSTPHPD peptide sequence on the surface of the P53 DNA binding domain (DBD). The DBD is shown in carton cyan representation and the predicted peptide is shown as magenta sticks. FIG. 6A. An overview of the DBD peptide complex. FIG. 6B. A closer examination of the DBD-peptide binding interface. FIG. 6C. A detailed atomic list of the non-bonded interaction between the DBD (chain B) and the predicted peptide binding position (chain A).

FIG. 7 shows dose response effects of p53-reactivating peptides in triplicates. SW480 cell line comprising p53 mutant p53R273H. Cells were cultured in 96 wells plates with 3000 cells/well. Serial dilutions of different peptides were added and the plates incubated for additional 72 h at 37° C. Then the medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm. Results are normalized to non-treated cells 100% viability.

Figure 8:
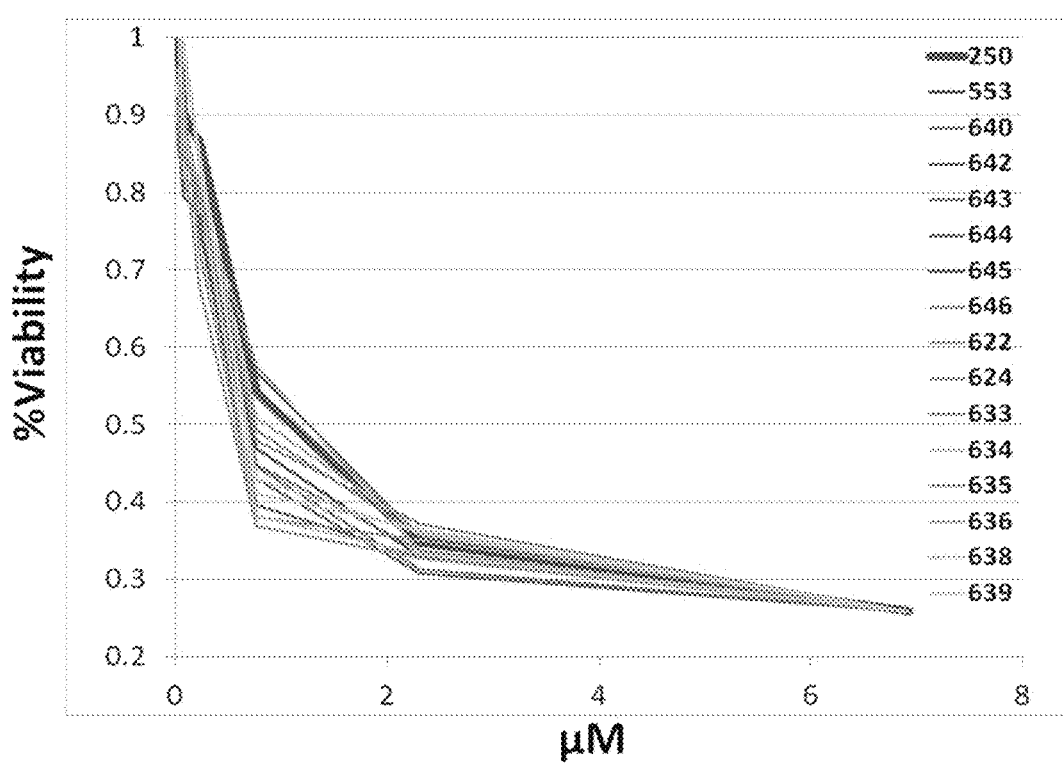

FIG. 8 shows dose response effects of p53-reactivating peptides in triplicates. ES2 cell line comprising p53 mutant S241F. Cells were cultured in 96 wells plates with 3000 cells/well. Serial dilutions of different peptides were added and the plates incubated for additional 48 h at 37° C. Then the medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm. Results are normalized to non-treated cells 100% viability.

Figure 9:
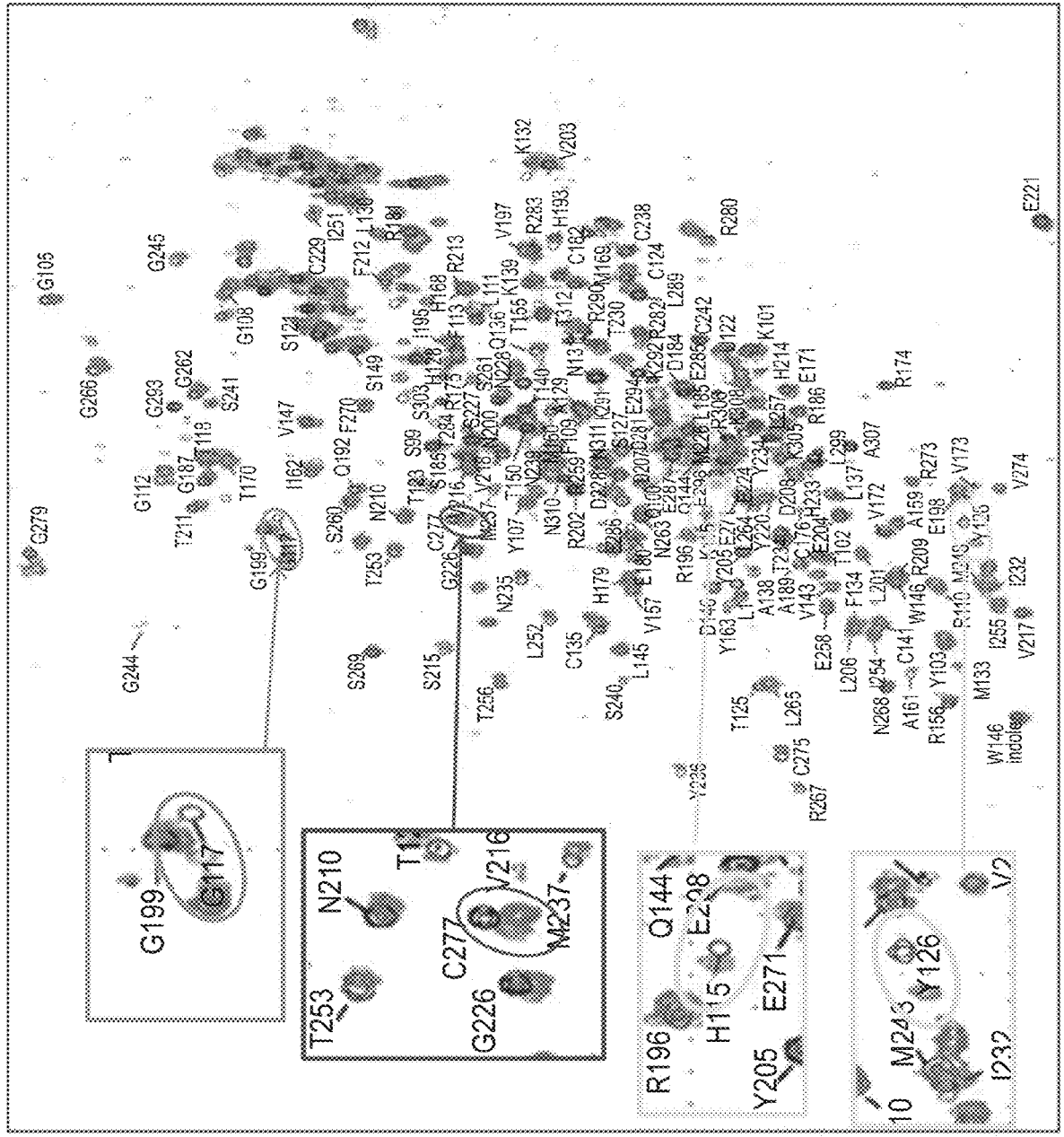

FIG. 9 shows 1H-15N HSQC spectra of wild-type p53 core domain (DBD) acquired at 293 K, DBD (94-312 of SEQ ID NO: 44) spectra and residue assignment as was produced by Wong et al is shown in black [Wong, K. B., et al., *Hot-spot mutants of p53 core domain evince characteristic local structural changes*. Proc Natl Acad Sci USA, 1999. 96(15): p. 8438-42]. NMR spectra produced for the free DBD (94-296) and for the DBD-pCAP 250 complex are shown in blue and red, respectively. Examples of moderate (C277 and R280) and strong peak changes (G117) are emphasized in magenta and brown respectively. The peak region of H115 and Y126 are emphasized in yellow.

Figure 10:
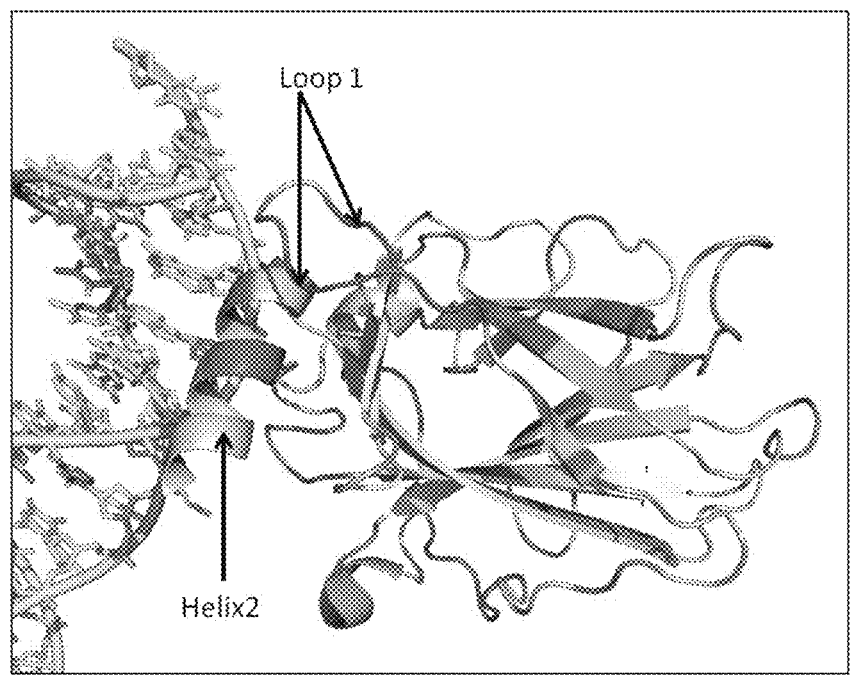

FIG. 10 shows mapping of the DBD structure for 1H-15N HSQC spectra changes as a result of the binding of pCAP 250 (SEQ ID NO: 1) to the DBD. The DBD structure is shown in cartoon representation and the DNA is colored yellow. Unassigned residues from the analysis of Wong et al. (supra) are colored green and residues involving peak changes upon the addition of pCAP 250 are colored magenta.

Figure 11A:
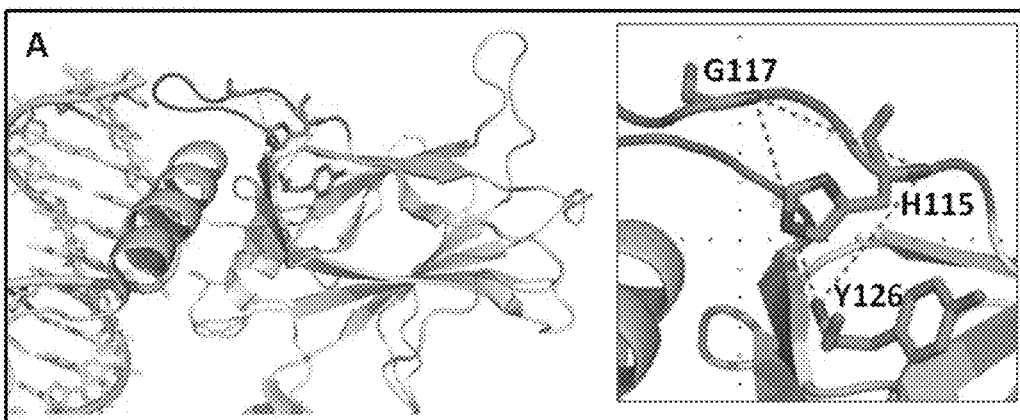
Figure 11B:
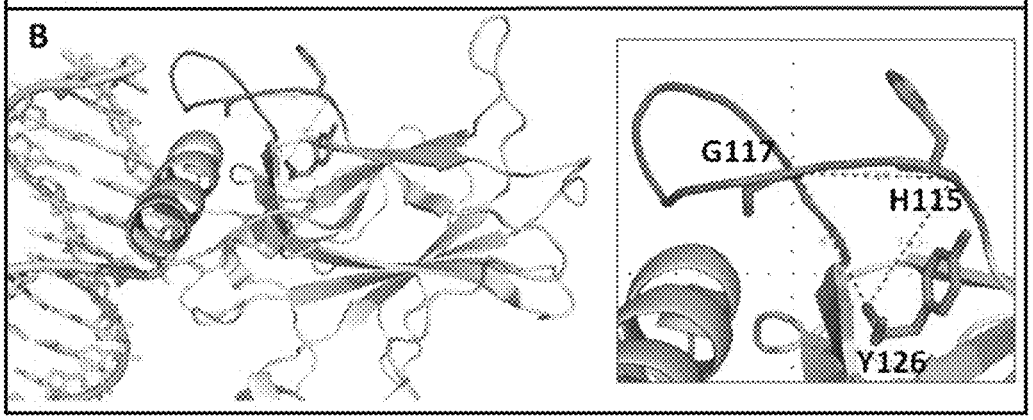

FIGS. 11A-B show the structural reorganization of H115, G117 and Y126. The DBD structure is shown in cartoon representation and the DNA is colored yellow. H115, G117 and Y126 are shown as green sticks and the L1 loop is colored magenta. FIGS. 11A and 11B present the top and the second top best energy DBD conformations solved by NMR (pdb code 2FEJ), respectively.

Figure 12:
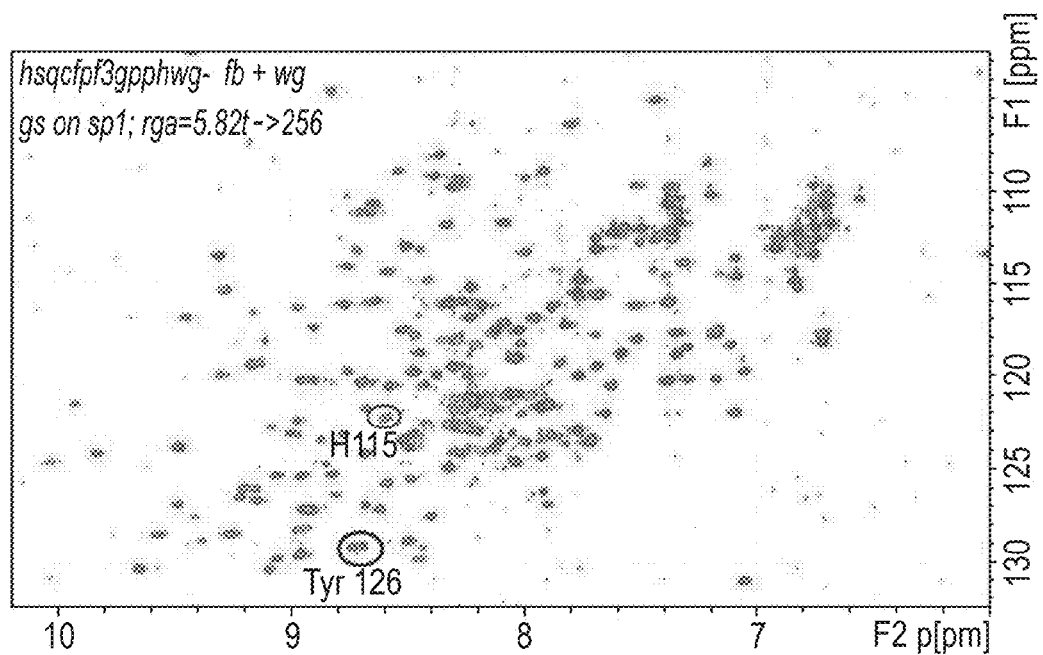

FIG. 12 show 1H-15N HSQC spectra of wild-type p53 DBD-peptide complexes acquired at 293 K. NMR spectra produced for the DBD-pCAP 250 and for the DBD-pCAP 615 (SEQ ID NO: 465) protein peptide complexes are shown in red and green, respectively. The peaks of H115 and Y126 are emphasised as circles.

Figure 13:
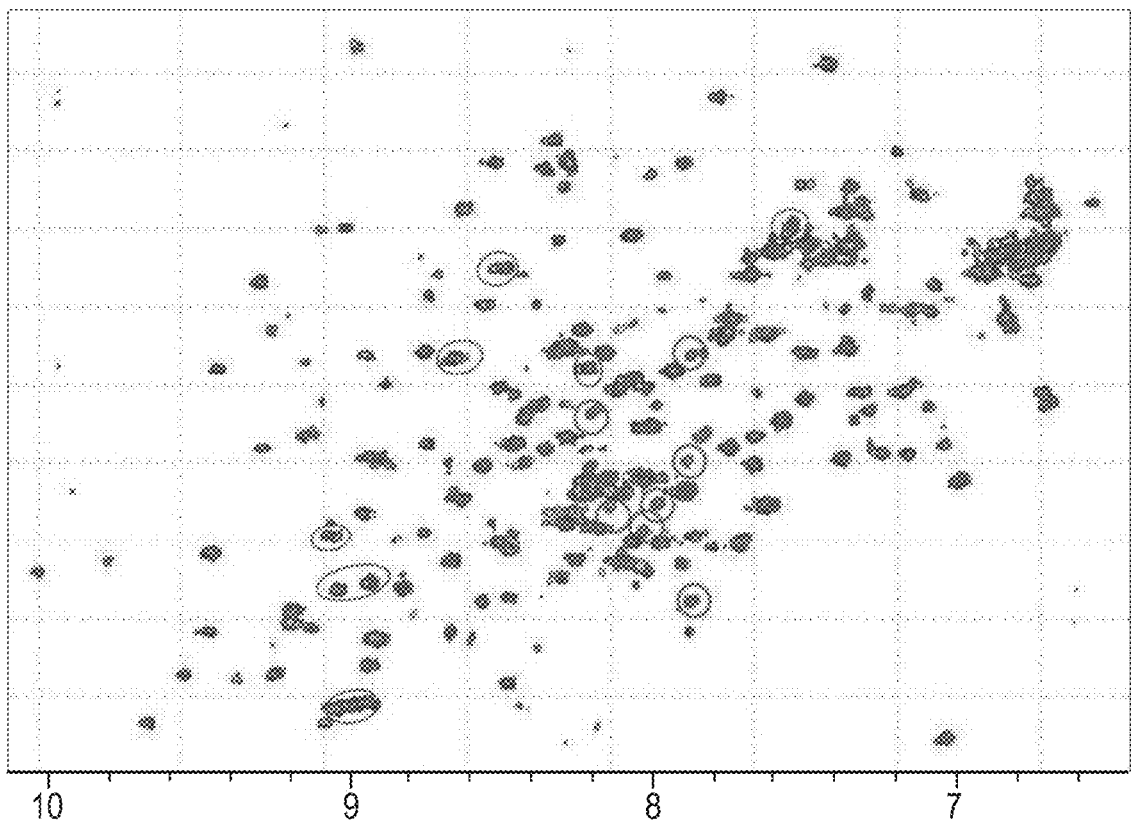

FIG. 13 show 1H-15N HSQC spectra of wild-type p53 DBD and DBD-pCAP 553 (SEQ ID NO: 429)-complex acquired at 293 K. NMR spectra produced for the free DBD and for the DBD-pCAP 553 protein peptide complex are shown in blue and red respectively. Strong unassigned peaks that specifically emerged up on the edition of the pCAP 553 peptide are emphasized as green ellipsoids. Few examples of peaks which become more condensed and circular in the DBD-pCAP 553 complex are emphasized in brown ellipsoids.

Figure 14:
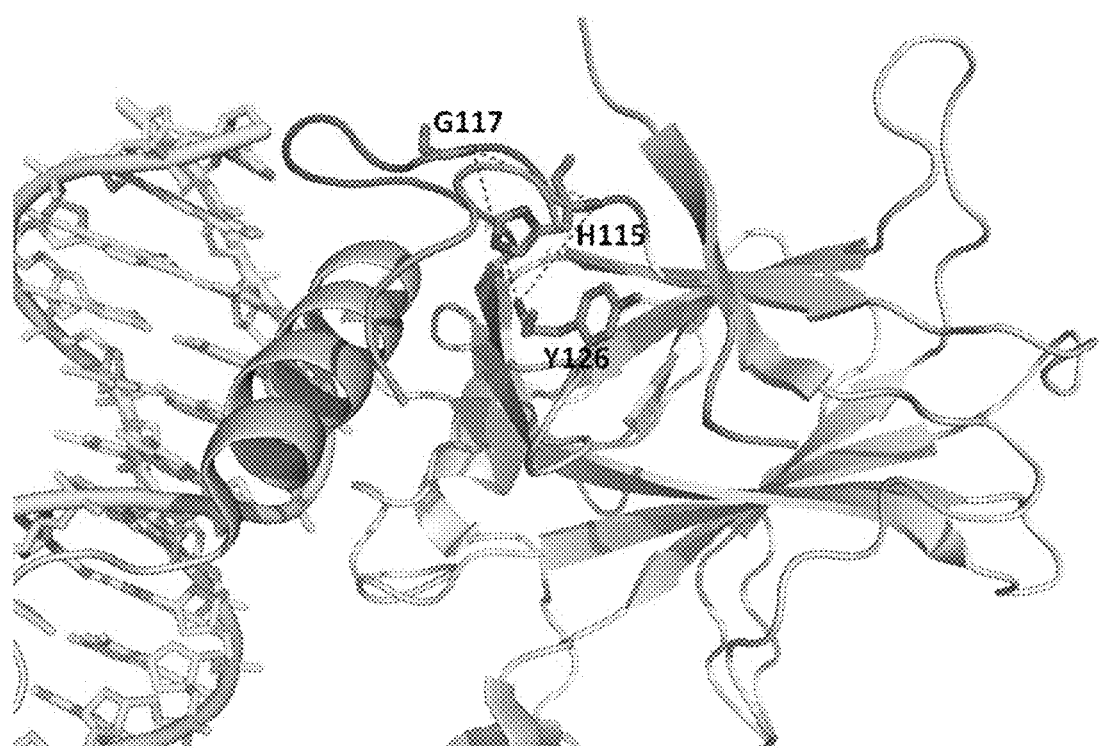

FIG. 14 shows top two predicted peptide binding models for the DBD-pCAP 250 complex. The DBD structure is shown in cartoon representation and the DNA is colored yellow. H115, G117 and Y126 are shown as green sticks and the L1 loop is colored magenta. The top two predicted peptide binding models for the DBD-pCAP 250 complex are colored in cyan.

DESCRIPTION OF SPECIFIC EMBODIMENTS OF THE INVENTION

The present invention, in some embodiments thereof, relates to peptides and use of same in the treatment of diseases, disorders or conditions associated with a mutant p53.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Inventors of some embodiments of the invention have previously described the use of phage display to select mutp53-reactivating peptides (WO2015/019318, which is hereby incorporated by reference in its entirety). Lead peptides including pCAP 250 (SEQ ID NO: 1) were shown to endow mutp53 with WTp53-like activities in vitro and in live cells, and cause regression of mutp53-bearing tumors in several xenograft models.

Whilst reducing the present invention to practice, the present inventors have uncovered that pCAP 250 binds the DNA Binding Domain (DBD) of p53. Structural/functional analysis using alanine scanning revealed a consensus for the binding of pCAP 250 to the DBD.

NMR experimental results provide further evidence for the explicit binding of pCAP 250 and its peptide variants to the WT DBD of the p53 protein. These results support the findings regarding the binding of pCAP 250 to the DBD using the microscale thermophoresis (MST) analysis (FIGS. 3A-K). The NMR results further indicate that the binding of pCAP 250 and its peptide variants induces structural changes in the DBD, which directly influence the integrity and stability of the DBD-DNA binding interface region, namely the Helix-2 and the L1 loop structural motifs, which are essential for the ability of the DBD to bind the DNA. The binding of pCAP 250 and its peptide variants further affects additional residues at the surroundings of the helix 2 and the L1 loop structural motifs, creating a relatively large yet decisive affected patch on the DBD surface.

These findings allow the design of novel peptides that share the same interaction with the DBD of p53 and are able to at least partially reactivate a mutant p53 protein such peptides endowed with anti-cancer activity are shown in Example 5.

Thus, according to an aspect of the present invention there is provided an isolated peptide comprising an amino acid sequence arranged in a space and configuration that allow interaction of the peptide with the DNA Binding Domain (DBD) of p53 through the same at least one residue of the DBD by which pCAP 250 (SEQ ID NO: 1) binds the DBD, wherein said peptide at least partially reactivates a mutant p53 protein.

According to a specific embodiment, the peptide is not SEQ ID NO: 1-338, 368-382 of WO2015/019318 (i.e., SEQ ID NOS: 59-382 herein).

According to a specific embodiment, the peptide is not any of the peptides taught in WO2015/019318 as having the activity of re-activating mutant p53, which is hereby incorporated by reference in its entirety.

As used herein the term "isolated" refers to at least partially separated from the natural environment e.g., from the body or from a peptide library.

As used herein the term "p53" also known as "TP53" refers to the gene sequence encoding the protein product of EC 2.7.1.37, generally functioning as a transcription factor, regulating the cell cycle, hence functioning, in its wild-type form, as a tumor suppressor gene. According to a specific embodiment, the p53 is a human p53.

As used herein, the terms "wild type p53", "wt p53" and "WT p53" may interchangeably be used and are directed to a wild type p53 protein, having the conformation of a wild type p53 protein and hence, activity of a wild type p53 protein. In some embodiments, wild type p53 can be identified by a specific monoclonal antibody. In certain embodiments, the monoclonal antibody is Ab1620.

Structural data for the protein is available from PDBe RCSB.

The term "conformation" with respect to a protein is directed to the structural arrangement (folding) of a protein in space.

As used herein, the terms "mutant p53", "Mut-p53", "mutated p53", and "p53 mutant" may interchangeably be used and are directed to a mutated p53 protein, incapable of efficiently functioning in a target cell. In some embodiments, a Mut-p53 cannot bind its target site. In some embodiments, a Mut-p53 is mutated at the DNA binding domain (DBD) region. In some embodiments, a Mut-p53 is misfolded in an inactive conformation. In some exemplary embodiments, the Mut-p53 is a temperature sensitive (ts) mut p53 R249S (R249S p53), a hot spot full length mutant p53 Mut-p53 R175H (R175H p53), or any other Mut-p53 protein. In some embodiments, a Mut-p53 is identified by a specific monoclonal antibody, capable of recognizing a misfolded conformation of p53 (induced by the mutation of the p53). In some embodiments, a Mut-p53 is identified by a specific monoclonal antibody. In certain embodiments, the monoclonal antibody is Ab420.

In certain embodiments, the mutant p53 protein comprises a mutation selected from the group consisting of R175H, V143A, R249S, R273H, R280K, P309S, P151S, P151H, C176S, C176F, H179L, Q192R, R213Q, Y220C, Y220D, R245S, R282W, D281G, S241F, C242R, R248Q, R248W, D281G, R273C and V274F. Each possibility represents a separate embodiment of the invention.

As referred to herein, the terms "reactivating peptide", "Mut-p53 reactivating peptide" or "the peptide" may interchangeably be used and are directed to a peptide capable of at least partially restoring activity to Mut-p53. The phrase "reactivating mutant p53 protein" as used herein refers to a peptide which upon its interaction with a mutant p53 protein, the mutant p53 protein increases at least one of its activities, wherein the activities are the activities of a wild type p53 protein. For example, upon its interaction with a peptide provided by the present invention, a mutant p53 protein may increase, directly or indirectly, the expression of pro-apoptotic proteins such as caspases in a cancer cell, in a similar way to what would a wild type p53 protein do in a similar situation or suppress tumors in vivo as can be assayed using a xenograft mouse model of the disease.

Without being bound by theory it is suggested that the reactivating peptide binds the mut p53 in the DBD and thermodynamically stabilizes the WTp53 protein folding and hence restore tumor suppression function.

In some embodiments, the reactivating peptide can reactivate a Mut-p53 by affecting the conformation of the Mut-p53, to assume a conformation which is more similar to or identical to a native, WT p53. In some embodiments, the reactivating peptide can reactivate a Mut-p53 to restore binding of the Mut-p53 to a WT p53 binding site in a target DNA. In some embodiments, the reactivating peptide can restore biochemical properties of the Mut-p53. In some embodiments, the reactivating peptide can induce the Mut-p53 protein to exhibit p53-selective inhibition of cancer cells. In some embodiments, the reactivating peptide can reactivate a Mut-p53 to have structural properties, biochemical properties, physiological properties and/or functional properties similar (i.e., ±, 10%, 20%, 30% difference between the Mut-p53 and WT p53) to or identical to a WT p53 protein such as determined in the binding/structural assays as described herein e.g., MST and NMR.

In some embodiments, the reactivating peptide is a peptide having 3-30 amino acids in length. In some embodiments, the reactivating peptide is a peptide having 7-30 amino acids in length. In some embodiments, the reactivating peptide is a peptide having 12-30 amino acids in length. In some embodiments, the reactivating peptide is a peptide having 3-25 amino acids in length. In some embodiments, the reactivating peptide is a peptide having 7-25 amino acids in length. In some embodiments, the reactivating peptide is a peptide having 12-25 amino acids in length. In some embodiments, the reactivating peptide is a peptide having 3-22 amino acids in length. In some embodiments, the reactivating peptide is a peptide having 7-22 amino acids in length. In some embodiments, the reactivating peptide is a peptide having 12-22 amino acids in length. In some embodiments, the reactivating peptide is a peptide having 7-9 amino acids in length. In some embodiments, the reactivating peptide is a peptide having 6-9 amino acids in length. In some embodiments, the reactivating peptide is a peptide having 7-10 amino acids in length. In some embodiments, the reactivating peptide is a peptide having 6-10 amino acids in length. In some embodiments, the reactivating peptide is a peptide being 9-10 amino acids in length. In some embodiments, the reactivating peptide is a peptide being 8-10 amino acids in length. In some embodiments, the reactivating peptide is a peptide being 6-9 amino acids in length. In some embodiments, the reactivating peptide is a peptide being 6-8 amino acids in length. In some embodiments, the reactivating peptide is a peptide being 6-7 amino acids in length. In some embodiments, the reactivating peptide is a peptide being 7-8 amino acids in length. In some embodiments, the reactivating peptide is a peptide being 7-9 amino acids in length. In some embodiments, the reactivating peptide is a peptide being 5-20 amino acids in length. In some embodiments, the reactivating peptide is a peptide being 6-15 amino acids in length. In some embodiments, the reactivating peptide is a peptide being 7 or 12 amino acids in length.

The term "capable of at least partially reactivating a mutant p53 protein" or "at least partially reactivate a mutant p53 protein" as interchangeably used herein refers to a peptide, wherein upon binding of the peptide to a mutant p53 protein, the mutant p53 protein gains or increases an activity similar to a corresponding activity of a wild type p53 protein.

As used herein "the DNA Binding Domain" or "DBD" of p53 refers to the domain of p53 which binds a p53 responsive element in a target protein (e.g., a consensus DNA binding element comprises or consists the amino-acid sequence set forth in SEQ ID NO: 44), typically attributed to residues 94-292, 91-292, 94-293, 94-296, 91-296, 91-293, 94-312 or 92-312 of human p53 (full length p53 GenBank: BAC16799.1, SEQ ID NO: 44). According to a specific embodiment, the DBD is of a mutated p53.

As mentioned, the peptide comprises an amino acid sequence arranged in a space and configuration that allow interaction of the peptide with the DBD of p53 through at least one residue of the DBD by which pCAP 250 (SEQ ID NO: 1) binds the DBD.

Thus, a reactivating peptide according to some embodiments of the invention is typically associated with the DBD domain of p53 such that the reactive group(s) of the peptide are positioned in a sufficient proximity to corresponding reactive group(s) (typically side chains of amino acid residues) in the DBD, so as to allow the presence of an effective concentration of the peptide in the DBD and, in addition, the reactive groups of the peptide are positioned in a proper orientation, to allow overlap and thus a strong chemical interaction and low dissociation. A reactivating peptide, according to some embodiments of the invention therefore typically includes structural elements that are known to be involved in the interactions, and may also have a restriction of its conformational flexibility, so as to avoid conformational changes that would affect or weaken its association with DBD of p53.

According to some embodiments, the interaction is via Helix-2 and L1 of said DBD.

Typically, helix-2 is positioned between amino acids 276-289 and L1 is positioned between amino acids 112-124.

According to some embodiments, the interaction affects the structural stability of Helix-2 and/or L1 of said DBD, as assayed by NMR.

According to some embodiments, the at least one residue in the DBD by which the interaction with the peptide is mediated is selected from the group consisting of H115, G117 of L1 of the p53 and Y126 and V274 and G279 and R280 of the p53 (wt or mutant in which the difference in amino acids is typically of single amino acids that do not significantly affect amino acid numbering. However, the skilled artisan would know how to find the corresponding amino acid (in terms of composition and position in the mutant p53).

According to some embodiments the interaction of the peptide with the DBD is non-covalent, e.g., water-mediated hydrogen bonding interactions.

According to some embodiments the interaction is by at least one amino acid of the amino acid sequence.

According to some embodiments the interaction is by at least two amino acids of the amino acid sequence.

According to some embodiments the interaction is by at least three amino acids of the amino acid sequence.

According to some embodiments the interaction is by at least four amino acids of the amino acid sequence.

According to a specific embodiment, the interaction is to amino acid Trp146 and/or Gln144 of human p53. This interaction is probably via the Ser of the pCAP 250 or its likes in analogous structures as further described hereinbelow.

According to a specific embodiment, the interaction is to amino acid Tyr126, Asn128 and/or Asp268 of human p53.

According to another specific embodiment, the interaction is to amino acid Lys101 of human p53 via Asp10 of the pCAP 250 or its likes in analogous structures as further described hereinbelow.

According to another specific embodiment, the interaction is to amino acid Thr102 of human p53 via Asp10 of the pCAP 250 or its likes in analogous structures as further described hereinbelow.

According to another specific embodiment, the interaction is to amino acid Phe113 of human p53 via Thr6 of the pCAP 250 or its likes in analogous structures as further described hereinbelow.

According to another specific embodiment, the interaction is to amino acid Trp146 of human p53 via Ser5 of the pCAP 250 or its likes in analogous structures as further described hereinbelow.

According to another specific embodiment, the interaction is to amino acid Ser5 of human p53 via Thr6 of the pCAP 250 or its likes in analogous structures as further described hereinbelow.

According to another specific embodiment, the interaction is to amino acid His8 of human p53 via Thr6 of the pCAP 250 or its likes in analogous structures as further described hereinbelow.

According to another specific embodiment, the interaction is to amino acid Gly112 of human p53 via Ser5 of the pCAP 250 or its likes in analogous structures as further described hereinbelow.

According to another specific embodiment, the interaction is to amino acid Gly112 of human p53 via Thr6 of the pCAP 250 or its likes in analogous structures as further described hereinbelow.

Other suggested positions for interactions on the surface of p53 DBD are listed in FIGS. 6A-C which is considered as part of the specification wherein each possibility represents an independent embodiment.

Other suggested positions for interactions on the surface of p53 DBD are listed in FIGS. 9-14 which is considered as part of the specification wherein each possibility represents an independent embodiment.

Methods of elucidating the amino acids either in the peptide or in the DBD which are critical for the interaction are well known in the art and include, but are not limited to crystallography, as well as the use of computer-based algorithms e.g., AnchorDock (Ben Shimon Structure. 2015 May 5; 23(5):929-40), Virtual crystallographic Calculators V.2. and the like.

According to a specific embodiment, the peptide comprises a consensus motif.

The term "consensus motif" as used herein refers to an amino acid sequence of at least 3 amino acids, 4, 5 or 6 amino acids which may be consecutive or non-consecutive. According to a specific embodiment, the consensus motif is 6 consecutive amino acids long.

According to a specific embodiment, the peptide comprises an amino acid sequence of:

$$X_1\text{-}X_2\text{-}X_3\text{-}X_4\text{-}X_5\text{-}X_6 \quad \text{(SEQ ID NO: 53)}$$

wherein, $X_1$ and $X_5$ are a positively charged amino acid;

$X_2$ is selected from the group consisting of Ser, Thr, Asn, Gln, Pro, Ala and Gly;

$X_3$ is any amino acid;

$X_4$ and $X_6$ are selected from the group consisting of an alpha methyl amino and a beta-breaker amino acid.

According to a specific embodiment, the peptide comprises an amino acid sequence of:

$$X_1\text{-}X_2\text{-}X_3\text{-}X_4\text{-}X_5\text{-}X_6 \quad \text{(SEQ ID NO: 54)}$$

wherein, $X_1$ and $X_5$ are selected from the group consisting of His, Arg and Lys;

$X_2$ is selected from the group consisting of Ser, Thr, Asn, Gln, Pro, Ala and Gly;

$X_3$, $X_4$, $X_6$ is any amino acid.

As used herein "positively charged amino acid" is an amino acid that can be positive (i.e. protonated) at physiological pH.

According to an embodiment, the positively charged amino acid is selected from the group consisting of is, Diaminobutyric acid (Dab), Arg and Lys.

According to a specific embodiment, $X_3$ is a D-amino acid.

According to a specific embodiment, $X_3$ is a phosphorylated (e.g phosphoserine) or phosphomimetic thereof (e.g., Glu or Asp).

According to a specific embodiment, $X_3$ is a non-phosphorylatable amino acid (e.g., Val).

According to a specific embodiment, the $X_3$ is a non-hydrogen bonding amino acid (e.g. Ala).

According to a specific embodiment, the $X_3$ is selected from the group consisting of polar uncharged amino acid (e.g., Ser) and a hydrophobic amino acid (e.g. Ile).

According to a specific embodiment, the $X_2$ is Ser.

According to a specific embodiment, the $X_4$ and $X_6$ are selected from the group consisting of Ser, Thr, Pro, Ala and Gly.

According to a specific embodiment, the $X_4$ is an alpha methyl amino acid or a beta breaker, e.g., Pro, Aib or Ala.

According to a specific embodiment, the $X_4$ is an alpha methyl amino acid.

According to a specific embodiment, the $X_6$ is Ala.

According to a specific embodiment, the peptide has the amino acid sequence HSAPHP (SEQ ID NO: 46).

According to a specific embodiment, the peptide comprises at least one additional amino acid ($X_7$) attached to the C-terminus of said amino acid sequence.

According to a specific embodiment, the at least one additional amino acid is a negatively charged amino acid (i.e., amino acid that is typically negative (i.e. de-protonated) at physiological pH) or a small amino acid (e.g., Gly, Ala, Val).

According to a specific embodiment, the at least one additional amino acid is selected from the group consisting of Asp, Glu, Gly, Ala and Ser.

According to a specific embodiment, the at least one negatively charged amino acid is Asp.

According to a specific embodiment, the at least one additional amino acid comprises two additional amino acids ($X_7$-$X_8$) and wherein said X8 is selected from the group consisting of His, Dab, Asp and Glu.

According to a specific embodiment, the at least one negatively charged amino acid is Asp or two consecutive Asp residues.

According to a specific embodiment, the peptide comprises at least one additional amino acid attached to the N-terminus of said amino acid sequence.

According to a specific embodiment, the peptide comprises at least two additional amino acids attached to the N-terminus of said amino acid sequence.

According to a specific embodiment, the at least one additional amino acid attached to the N-terminus of said amino acid sequence is Arg or two consecutive Arg residues.

Binding of the peptide to the DBD can be determined using any method known in the art, such as a competition assay wherein a soluble DBD is used as a competing agent.

The term "recombinant or synthetic peptide" as used herein refers to a peptide produced by standard biotechnological methods known in the art, such as expression in bacteria or Solid-phase peptide synthesis (SPPS).

According to a specific embodiment, the peptide further comprises a cell penetrating moiety, which can be attached to the N-terminus of the peptide, the C-terminus of the peptide or at both ends of the peptide. It will be appreciated that this moiety can also be bound to the peptide body not via its termini, as long as it doesn't interfere with the binding of the peptide to the DBD. It will be appreciated that this moiety is a heterologous moiety that is not bound to the peptide in nature in the same manner (i.e., position or chemistry).

The term "Permeability" as used herein refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes.

As used herein the phrase "permeability-enhancing moiety" refers to an agent which enhances translocation of any of the attached peptide across a cell membrane.

Any moiety known in the art to facilitate actively or passively or enhance permeability of compositions into cells may be used for conjugation with the peptide core according to the present invention. Non-limitative examples include: hydrophobic moieties such as fatty acids, steroids and bulky aromatic or aliphatic compounds; moieties which may have cell-membrane receptors or carriers, such as steroids, vitamins and sugars, natural (e.g., positively charged amino acids e.g., Lys or Arg) and non-natural amino acids and proteinaceous moiety e.g., transporter peptides, also referred to as "cell penetrating peptides" or a CPP, poly-Arginine or poly-Lysine, a combination of same or an antibody. According to some embodiments, the proteinaceous moiety is a CPP. According to some embodiments, the proteinaceous moiety is poly-Arginine. According to some embodiments, the hydrophobic moiety is a lipid moiety or an amino acid moiety. According to some embodiments of the invention, the cell penetrating moiety is a combination of a proteinaceous moiety and a lipid-based moiety (e.g., one from the N terminus and the other from the C-terminus of the peptide).

Cell-Penetrating Peptides (CPPs) are short peptides (≤40 amino acids), with the ability to gain access to the interior of almost any cell. They are highly cationic and usually rich in arginine and lysine amino acids. Indeed the present inventors have used positively charged amino acids (on either peptide termini) or poly-cationic amino acids (at least 2 e.g., 2-12) poly-Arg to impart the peptides with cell permeation. They have the exceptional property of carrying into the cells a wide variety of covalently and noncovalently conjugated cargoes such as proteins, oligonucleotides, and even 200 nm liposomes. Therefore, according to additional exemplary embodiment CPPs can be used to transport the peptides to the interior of cells.

TAT (transcription activator from HIV-1), pAntp (also named penetratin, *Drosophila* antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research (2007) 100: 1626-1633].

However, the disclosure is not so limited, and any suitable penetrating agent may be used, as known by those of skill in the art.

When the peptides of the present invention are attached to cell penetrating peptides, it is contemplated that the full length peptide is no greater than 50 amino acids, no greater than 40 amino acids, no greater than 35 amino acids, no greater than 30 amino acids, no greater than 25 amino acids, no greater than 22 amino acids, no greater than 20 amino acids, no greater than 15 amino acids, no greater than 12 amino acids, no greater than 10 amino acids, no greater than 9 amino acids, no greater than 8 amino acids, or no greater than 7 amino acids.

Non-limitative examples of non-proteinaceous cell penetrating moieties include: hydrophobic moieties such as lipids, fatty acids, steroids and bulky aromatic or aliphatic compounds; moieties which may have cell-membrane receptors or carriers, such as steroids, vitamins and sugars, nanoparticles and liposomes.

The term "fatty acid moiety" as used herein refers to a part of a fatty acid that exhibits a particular set of chemical and pharmacologic characteristics similar to the corresponding complete fatty acid origin molecule. The term further refers to any molecular species and/or molecular fragment comprising the acyl component of a fatty (carboxylic) acid.

A permeability-enhancing moiety according to the present invention is preferably connected covalently to the peptide sequence via a direct bond or via a linker, to form a peptide conjugate. The permeability-enhancing moiety may be connected to any position in the peptide moiety, directly or through a spacer, preferably to the amino terminus of the peptide. According to certain embodiments, the permeability enhancing moiety is a fatty acid.

The hydrophobic moiety according to the invention may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl ($C_{11}$); lauroyl ($C_{12}$); tridecanoyl ($C_{13}$); myristoyl ($C_{14}$); pentadecanoyl ($C_{15}$); palmitoyl ($C_{16}$); phtanoyl (($CH3)_4$); heptadecanoyl ($C_{17}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds.

Other examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N,N''-Bis(hexadecylaminocarbonylmethylene)-N,N',N''-tris((-N,N,N-trimethylammonium-ethylaminocarbonylmethylenediethylenetriamine hexaiodide; N,N'-Bis(dodecylaminocarbonylmethylene)-N,N''-bis((-N,N,N-trimethylammonium ethylaminocarbonylmethylene)cyclohexylene-1,4-diamine tetraiodide; 1,7,7-tetra-((-N,N,N,N-tetramethylammoniumethylaminocarbonylmethylene)-3-hexadecylaminocarbonylmethylene-1,3,7-triaazaheptane heptaiodide; N,N,N',N'-tetra((-N,N,N-trimethylammonium-ethylaminocarbonylmethylene)-N'-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

The terms "polypeptide" and "peptide" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

"Conservative substitution" refers to the substitution of an amino acid in one class by an amino acid of the same class, where a class is defined by common physico-chemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (He, Leu, Val, Met); and Class VI (Phe, Tyr, Trp). For example, substitution of an Asp for another Class III residue such as Asn, Gin, or Glu, is a conservative substitution.

Other classifications include positive amino acids (Arg, His, Lys), negative amino acids (Asp, Glu), polar uncharged (Ser, Thr, Asn, Gln), hydrophobic side chains (Ala, Val, Ile, Leu, Met, Phe, Tyr, Trp).

"Non-conservative substitution" refers to the substitution of an amino acid in one class with an amino acid from another class; for example, substitution of an Ala, a Class II residue, with a Class III residue such as Asp, Asn, Glu, or Gln.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr. Other synthetic options are listed hereinbelow in Table 2.

The peptides of some embodiments of the invention may also include one or more modified amino acids or one or more non-amino acid monomers (e.g. fatty acids, complex carbohydrates etc.).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |

TABLE 2-continued

| Non-conventional amino acid | Code | Non-conventional amino acid | Code |
|---|---|---|---|
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclization does not severely interfere with peptide characteristics, cyclic forms of the peptide can also be utilized.

In order to improve bioavailability, the peptide may comprise at least one D amino acid (e.g., 2-7, 2-6, 2-5, 2-4, 2-3). According to a specific embodiment, all the amino acids in the peptide are D amino acids.

In some embodiments, the peptide is chemically modified.

"Chemically modified" refers to an amino acid that is modified either by natural processes, or by chemical modification techniques which are well known in the art. Among the numerous known modifications, typical, but not exclusive examples include: acetylation, acylation, amidation, ADP-ribosylation, glycosylation, glycosaminoglycanation, GPI anchor formation, covalent attachment of a lipid or lipid derivative, methylation, myristlyation, pegylation, prenylation, phos-phorylation, ubiquitination, or any similar process (see e.g., SEQ ID NOs: 2, 17-19).

According to a specific embodiment, the peptide may comprise C-terminal amidation.

Yet alternatively or additionally the peptide may be conjugated to non-proteinaceous non-toxic moiety such as, but are not limited to, polyethylene glycol (PEG), Polyvinyl pyrrolidone (PVP), poly(styrene comaleic anhydride) (SMA), and divinyl ether and maleic anhydride copolymer (DIVEMA).

It will be appreciated that the peptides of the invention can also utilize peptide homologues which exhibit the desired activity (e.g., reactivation of p53 mutants), also referred to herein as functional equivalents, whereby the activity of the peptide homologue is determined according to methods known in the art such as described herein. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO: 53 or 54 or 1 (provided its not the peptides disclosed in WO2015/019318 (e.g., SEQ ID NOs: 286-321).

According to a specific embodiment, the peptide comprises the amino acid sequence or is set forth in SEQ ID NO: 8, 412-464.

According to a specific embodiment, the peptide is selected from the group of sequences of SEQ ID NO: 429, 448, 449, 446 and 462.

In certain embodiments, the peptide at least partially changes the conformation of the mutant p53 protein to a conformation of a wild-type (WT) p53 protein.

Known in the art are antibodies that specifically recognize only wild type p53 proteins. Such antibodies are highly useful in determining whether a certain p53 protein, either wild type or mutant, holds the conformation of a wild type, functional p53 protein. Thus, in certain embodiments, the peptide at least partially changes the conformation of the mutant p53 protein such that the mutant p53 protein is recognized by a monoclonal antibody exclusively directed against a WT p53 protein or against a p53 protein holding a WT p53 protein conformation. In certain embodiments, the monoclonal antibody is Ab1620.

It should be understood that since p53 is expressed from both alleles, the overall content of intra-cellular p53 can be either wild-type (wt/wt), mixture of wt and mutant p53 (wt/mut) or mutant p53 only (when both alleles are mutated (mut/mut), or one allele is deleted (mut/-)). In cancer, the situation is often wt/mut, mut/mut or mut/-. Since p53 acts as a tetramer, mutant p53 proteins may abrogate the activity of wild type p53 proteins, which may exist in the cancer's cells. Therefore, the peptides provided by the present invention are particularly useful in treating cancers in which increasing the level of wild type p53 proteins is not fruitful.

In certain embodiments, the peptide at least partially restores the activity of the mutant p53 protein to at least one of the activities of a WT p53 protein.

As used herein the term "reducing" refers to statistically significantly decreasing a certain phenotype by at least about 10%, 20%, 30%, 40%, 50%, 60%, 70%75%, 80%, 95% or even 100% as compared to a control (e.g., same cell/animal system treated with a control vehicle or non-treated at all) under the same assay conditions.

As used herein the term "increasing" or "improving" refers to statistically significantly increasing a certain phenotype by at least about 10%, 20%, 30%, 40%, 50%, 60%, 70%, 75%, 80%, 95% or even 100% as compared to a control (e.g., same cell/animal system treated with a control vehicle or non-treated at all) under the same assay conditions.

The term "cells expressing the mutant p53 protein" as used herein refers to cells which express from at least one allele a mutant p53 protein. In certain embodiments, the term "cells expressing the mutant p53 protein" is interchangeable with "cancer cells".

The term "pro-apoptotic genes" refers to a gene, or a multitude of genes, involved in apoptosis, either directly (such as certain caspases) or indirectly (for example, as part of a signal transduction cascade).

In certain embodiments, the activity is reducing viability of cells expressing the mutant p53 protein. In certain embodiments, the activity is promoting apoptosis of cells expressing the mutant p53 protein. In certain embodiments, the activity is activating pro-apoptotic genes of cells expressing said mutant p53 protein. In certain embodiments, the pro-apoptotic genes are selected from the group consisting of CD95, Bax, DR4, DR5, PUMA, NOXA, Bid, 53AIP1 and PERP. Each possibility represents a separate embodiment of the invention.

In certain embodiments, the activity is binding to a p53 consensus DNA binding element in cells expressing the mutant p53 protein. In certain embodiments, the consensus DNA binding element comprises or consists the nucleotides sequence set forth in SEQ ID NOs: 55 and 56.

Methods of monitoring cellular changes induced by the any of the peptides of the present invention are known in the art and include for example, the MTT test which is based on the selective ability of living cells to reduce the yellow salt MTT (3-(4, 5-dimethylthiazolyl-2)-2, 5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); as well as various RNA and protein detection methods (which detect level of expression and/or activity) which are further described herein below.

In certain embodiments, the binding results in at least partial activation of an endogenous p53 target gene. In certain embodiments, the endogenous target gene is selected from the group consisting of p21, MDM2 and PUMA. Each possibility represents a separate embodiment of the invention.

In certain embodiments, the mutant p53 protein is of a different conformation than a WT p53 protein. In certain embodiments, the mutant p53 protein is at least partly inactive compared to a WT p53 protein.

In certain embodiments, the mutant p53 protein is not recognized by a monoclonal antibody directed against a WT p53 protein. In certain embodiments, the mutant p53 protein, upon binding to the peptide, is recognized by a monoclonal antibody directed against a WT p53 protein. In certain embodiments, the monoclonal antibody is Ab1620.

In some embodiments, the reactivating peptide can reactivate a Mut-p53 to have structural properties, biochemical properties, physiological properties and/or functional properties similar to or identical to a WT p53 protein.

According to some embodiments, there are provided Mut-p53 reactivating peptides, wherein the peptides are in the length of about 3-25 amino acids. In some embodiments, the Mut-p53 reactivating peptides are in the length of about 4-15 amino acids. In some embodiments, the Mut-p53 reactivating peptides are in the length of about 7-12 amino acids. In some embodiments, the Mut-p53 reactivating peptides are in the length of 7 amino acids. In some embodiments, the Mut-p53 reactivating peptides are in the length of 12 amino acids. Each possibility represents a separate embodiment of the invention.

Other peptide lengths are recited throughout the application. Each possibility represents a separate embodiment of the invention.

According to some embodiments, a Mut-p53 reactivating peptide can affect Mut-p53 such that it can trans-activates a reporter gene (such as Luciferase) having WT p53 binding element in its promoter. In some embodiments the transactivation of the reporter gene may be performed in vitro (for example, in a test tube or well), or in-vivo in a cell, harboring the reporter gene construct.

According to some embodiments, a Mut-p53 reactivating peptide can bind to the DNA binding Domain (DBD) of a mutated p53. In some embodiments, the mutated p53 harbors a mutation in its DNA binding domain (DBD).

The term "pharmaceutical composition" as used herein refers to any composition comprising at least one pharmaceutically active ingredient.

The term "associated with a mutant p53 protein" as used herein refers to any disease, disorder or condition which is caused by a mutant p53 protein or its progression relates to the presence of a mutant p53 protein in a cell or an organ.

It should be understood that since p53 is expressed from both alleles, the overall content of intra-cellular p53 can be either wild-type (wt/wt), mixture of wt and mutant p53 (wt/mut) or mutant p53 only (when both alleles are mutated (mut/mut), or one allele is deleted (mut/-)). In cancer, the situation is often wt/mut, mut/mut or mut/-. Since p53 acts as a tetramer, mutant p53 proteins may abrogate the activity of wild type p53 proteins, which do exist in the cancer's cells. Therefore, the peptides provided by the present invention are particularly useful in treating cancers. Of note, the cell may have more than two p53 alleles at least one of which being of mutant p53.

The term "therapeutically effective amount" as used herein refers to an amount of a composition containing a peptide according to the present invention that is sufficient to reduce, decrease, and/or inhibit a disease, disorder or condition in an individual.

According to an aspect of the invention there is provided a method of treating a disease, disorder or condition associated with a mutant p53 protein, comprising administering to a subject in need thereof a therapeutically effective amount of the isolated peptide as described herein (e.g., SEQ ID NO: 8, 412-464), thereby treating said disease, disorder or condition.

According to an aspect of the invention there is provided a method of treating a disease, disorder or condition associated with a mutant p53 protein, comprising administering to a subject in need thereof a therapeutically effective amount of an isolated peptide comprising an amino acid sequence having a space and configuration that allow binding of the peptide to the DNA Binding Domain (DBD) of p53 in the same mode as pCAP 250 (SEQ ID NO: 1) binds said DBD, wherein said peptide at least partially reactivates a mutant p53 protein and wherein said therapeutically effective amount is 0.01-0.3 mg/kg per day or 0.01-0.2 mg/kg per day (e.g., 0.01-0.35 mg/kg per day, 0.01-0.35 mg/kg per day, 0.01-0.15 mg/kg per day, 0.01-0.1 mg/kg per day, 0.01-0.095 mg/kg per day, 0.01-0.09 mg/kg per day, 0.01-0.085 mg/kg per day, 0.01-0.08 mg/kg per day, 0.01-0.075 mg/kg per day, 0.01-0.07 mg/kg per day, 0.01-0.065 mg/kg per day, 0.01-0.06 mg/kg per day, 0.01-0.055 mg/kg per day, 0.01-0.05 mg/kg per day, 0.01-0.45 mg/kg per day, 0.01-0.04 mg/kg per day, 0.01-0.035 mg/kg per day, 0.01-0.03 mg/kg per day), thereby treating said disease, disorder or condition.

As referred to herein, the term "treating a disease" or "treating a condition" is directed to administering a composition, which includes at least one agent, effective to ameliorate symptoms associated with a disease, to lessen the severity or cure the disease, or to prevent the disease from occurring in a subject. Administration may include any administration route. In some embodiments, the disease is a disease that is caused by or related to the presence of a mutated p53 in a cell, tissue, organ, body, and the like. In some embodiments, the disease is cancer. In some embodiments, the cancer is selected from the group consisting of breast cancer, colon cancer, ovarian cancer and lung cancer.

In some embodiments, the cancer is a metastatic cancer.

In some embodiments, the cancer is a metastatic breast cancer, metastatic colon cancer, metastatic ovarian cancer or metastatic lung cancer.

Each possibility represents a separate embodiment of the invention. In some embodiments, the subject is a mammal, such as a human. In some embodiments, the subject is a mammal animal. In some embodiments, the subject is a non-mammal animal. In some embodiments the subject is diagnosed with the disease, condition or disorder.

In some embodiments, cancer is adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, hodgkin's disease, non-hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, skin cancer, kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or wilms' tumor.

In some embodiments, the cancer is a lung cancer.

In some embodiments, the cancer is an ovarian cancer.

In some embodiments, the cancer is a triple negative breast cancer.

In some embodiments, the cancer is a metastatic lung cancer.

In some embodiments, the cancer is a metastatic ovarian cancer.

In some embodiments, the cancer is a metastatic triple negative breast cancer.

In some embodiments, cancer is a non-solid tumor such as a blood cancer. In another embodiment, a non-solid tumor or blood cancer is leukemia or lymphoma. In another embodiment, a non-solid tumor or blood cancer is acute lymphoblastic leukemia (ALL). In another embodiment, a non-solid tumor or blood cancer is acute myelogenous leukemia (AML). In another embodiment, a non-solid tumor or blood cancer is chronic lymphocytic leukemia (CLL). In another embodiment, a non-solid tumor or blood cancer is small lymphocytic lymphoma (SLL). In another embodiment, a non-solid tumor or blood cancer is chronic myelogenous leukemia (CML). In another embodiment, a non-solid tumor or blood cancer is acute monocytic leukemia (AMOL). In another embodiment, a non-solid tumor or blood cancer is Hodgkin's lymphomas (any of the four subtypes). In another embodiment, a non-solid tumor or blood cancer is Non-Hodgkin's lymphomas (any of the subtypes). In another embodiment, a non-solid tumor or blood cancer is myeloid leukemia.

For use in the methods of the invention, the reactivating peptides may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient thereof. Suitable carriers typically include physiological saline or ethanol polyols such as glycerol or propylene glycol.

The reactivating peptides may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethylamino ethanol, histidine and procaine.

The compositions may be suitably formulated for intravenous, intramuscular, subcutaneous, or intraperitoneal administration and conveniently comprise sterile aqueous solutions of the reactivating peptides, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the reactivating peptides, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the reactivating peptides into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

In some embodiments, the reactivating peptides of the invention may be formulated in peroral or oral compositions and in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.9% of reactivating peptides, or in another embodiment, from about 0.01% to about 10%.

In some embodiments, compositions for use in the methods of this invention comprise solutions or emulsions, which in some embodiments are aqueous solutions or emulsions comprising a safe and effective amount of a reactivating peptide and optionally, other compounds, intended for topical intranasal administration.

In some embodiments, injectable solutions of the invention are formulated in aqueous solutions. In one embodiment, injectable solutions of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The reactivating peptides of the invention may be administered by any suitable administration route, selected from oral, topical, transdermal or parenteral administration. According to some embodiments the route of administration is via topical application selected from dermal, vaginal, rectal, inhalation, intranasal, ocular, auricular and buccal. According to some embodiments the route of administration is via parenteral injection. In various embodiments, the step of administering is carried out by a parenteral route selected from the group consisting of intravenous, intramuscular, subcutaneous, intradermal, intraperitoneal, intraarterial, intracerebral, intracerebroventricular, intraosseus and intrathecal. For example, the reactivating peptides may be administered systemically, for example, by parenteral routes, such as, intraperitoneal (i.p.), intravenous (i.v.), subcutaneous, or intramuscular routes. The reactivating peptides of the invention and/or any optional additional agent may be administered systemically, for example, by intranasal administration. The reactivating peptides of the invention and/or any optional additional agent may be administered systemically, for example, by oral administration, by using specific compositions or formulations capable of providing oral bioavailability to proteins. The reactivating peptides of the invention and/or any optional additional agent may be administered locally.

According to a specific embodiment, administering comprises subcutaneous administering.

Alternatively or additionally, according to a specific embodiment, administering comprises continuous infusion.

Thus the reactivating peptides (e.g., SEQ ID NO: 1, 8, or 412-464 or 429, 448, 449, 446, 462) can also be delivered by slow-release delivery systems, pumps, and other known delivery systems for continuous infusion for example in the following doses e.g., 0.01-0.3 mg/kg per day, 0.01-0.15 mg/kg per day, 0.01-0.1 mg/kg per day, 0.01-0.095 mg/kg per day, 0.01-0.09 mg/kg per day, 0.01-0.085 mg/kg per day, 0.01-0.08 mg/kg per day, 0.01-0.075 mg/kg per day, 0.01-0.07 mg/kg per day, 0.01-0.065 mg/kg per day, 0.01-0.06 mg/kg per day, 0.01-0.055 mg/kg per day, 0.01-0.05 mg/kg per day, 0.01-0.45 mg/kg per day, 0.01-0.04 mg/kg per day, 0.01-0.035 mg/kg per day, 0.01-0.03 mg/kg per day). Dosing regimens may be varied to provide the desired circulating levels of particular reactivating peptides based on its pharmacokinetics. Thus, doses are calculated so that the desired circulating level of therapeutic agent is maintained.

Typically, the effective dose is determined by the activity of the reactivating peptides and the condition of the subject, as well as the body weight or surface area of the subject to be treated. The size of the dose and the dosing regime is also determined by the existence, nature, and extent of any adverse side effects that accompany the administration of the reactivating peptides in the particular subject.

In some embodiments, there is provided a kit for treating or preventing a p53 related condition. In some embodiments, the kit comprises a container (such as a vial) comprising a Mut-p53 reactivating peptide in a suitable buffer and instructions for use for administration of the reactivating peptide.

It is suggested that the efficacy of treatment with the peptides of the invention may be augmented when combined with gold standard treatments (e.g., anti-cancer therapy). Thus, the peptide can be used to treat diseases or conditions associated with p53 (as described hereinabove) alone or in combination with other established or experimental therapeutic regimen for such disorders. It will be appreciated that treatment with additional therapeutic methods or compositions has the potential to significantly reduce the effective clinical doses of such treatments, thereby reducing the often devastating negative side effects and high cost of the treatment.

Therapeutic regimen for treatment of cancer suitable for combination with the peptides of some embodiments of the invention or polynucleotide encoding same include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. According to a specific embodiment, the chemotherapy is platinum-based.

Anti-Cancer Drugs

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to another aspect of the invention there is provided a method of treating a disease, disorder or condition associated with a mutant p53 protein, comprising administering to a subject in need thereof a therapeutically effective amount of a platin-based chemotherapy and an isolated peptide comprising an amino acid sequence having a space and configuration that allow binding of the peptide to the DNA Binding Domain (DBD) of p53 in the same mode as pCAP 250 (SEQ ID NO: 1) binds said DBD (e.g., SEQ ID NO: 1, 8, 412-464, 429, 448, 449, 446, 462), wherein said peptide at least partially reactivates a mutant p53 protein, thereby treating said disease, disorder or condition.

Specific examples of platinum-based chemotherapies include, but are not limited to, cisplatin, the first to be developed, carboplatin, a second-generation platinum-based antineoplastic agent, oxaliplatin, satraplatin, picoplatin, Nedaplatin, Triplatin, Lipoplatin, a liposomal version of cisplatin.

Kits and articles or manufacture for effecting combination treatments as described herein (e.g., the peptide together with platinum-based chemotherapy) are also contemplated herein.

It will be appreciated that a peptide comprising the amino acid sequence selected from the group consisting of 59-382 can also be implemented in the above-described methods.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures

Crystal Violet Viability Assay

Cells were cultured in 96 wells plates with 2500-4000 cells/well. Serial dilutions of different peptides were added and the plates incubated for additional 48 h at 37° C. Then medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm.

ChIP Analysis

Cells were cross-linked with formaldehyde (1% final concentration) at room temperature for 10 min. The formaldehyde was neutralized with glycine 0.25M for 5 min. Cells were washed twice with 10 ml of ice-cold PBS and harvested by scraping. Eventually, cells were resuspended in 0.3 ml of lysis buffer (1% SDS, 10 mM EDTA, 50 mM Tris-HCl, pH 8.1, protease inhibitor cocktail) and sonicated for 6 min in sonication bath followed by centrifugation for 10 min on ice to produce 200-500 bp fragments. Supernatants were collected and diluted 10 times in the ChIP dilution buffer (1% Triton X-100, 2 mM EDTA, 150 mM NaCl, 20 mM Tris-HCl, pH 8.1) followed by immuno-clearing with 40 µl of pre-blocked protein A-sepharose with 2 µg sheared salmon sperm DNA and 10 µg BSA for 2 hour at 4° C. Immuno-precipitation was performed overnight at 4° C. with specific αp53 or αRNApolII poly clonal antibodies. Following immuno-precipitation, 40 µl protein A-Sepharose were added and further incubated for another 1 hr. Precipitates were sequentially washed in TSE I (0.1% SDS, 1% Triton X-100, 2 mM EDTA, 20 mM Tris-HCl, pH 8.1, 150 mM NaCl), TSE II (500 mM NaCl), and buffer III (0.25 M LiCl, 1% NP-40, 1% deoxycholate, 1 mM EDTA, 10 mM Tris-HCl, pH 8.1). Precipitates were washed three times with TE buffer and extracted twice with 1% SDS, 0.1 M NaHCO$_3$. Eluates were pooled and heated at 65° C. for overnight to reverse the formaldehyde cross-linking. DNA fragments were purified with a QIAquick Spin Kit (Qiagen, CA). Immuno-precipitation reactions were performed in triplicate. Beads only served as a non-specific control. Quantitative analysis of the active and repressive histone marks in the CUP products from clones were assessed by quantitative RT-PCR. In order to normalize the efficiency of immunoprecipitation (IP), the normalization of chromatin IP was done using specific primers for necdin promoter region and 5' region.

CRISPR p53 Knockout

Plasmid #42230, containing a TP53 exon 3 single guide RNA (sgRNA), was from Addgene. ES2 cells were transfected using jetPEI reagent (Polyplus) according to the manufacturer's protocol. After 48 hours, cells were seeded in a 96 well plate as single cell clones. Single cell clones were expanded and their p53 status was examined by Western blot analysis, using the DO-1 anti-p53 antibody.

sgRNA sequences:

```
                                          (SEQ ID NO: 47)
F:      5'-CACCGCCATTGTTCAATATCGTCCG-3'

(SEQ ID NO: 48)
R:      5'-AACCGGACGATATTGAACAATGG-3'
```

Preclinical Testing of Peptides

Mice (6 weeks Athymic nude) were injected subcutaneously with $2 \times 10^5$-$10^6$ cells into each femur. All the cell lines employed in these experiments stably express a luciferase reporter gene to enable monitoring of tumor growth by live imaging. 4-18 days later, when tumors reached visible size, the mice were randomly divided into several groups: a control group, treated with either a single control peptide, and groups treated with effective peptide, either a single peptide. Peptides were administered either by intratumoral injection of 10 µg peptide per tumor in 40 µl PBS, three times a week or by Alzet mini pumps 0.8 mg for two weeks. Tumor growth over time was measured by live imaging, using the IVIS2000 system. Exposure time was calibrated to 20 seconds. 16 images were taken over 8 minutes and peak luminescence values were taken for each tumor. Experiments were conducted until tumors reached maximal allowed size of 1 cm$^3$, at which mice were sacrificed and tumors extracted, measured and weighed.

RT-PCR

RNA was obtained using Macherey-Nagel NucleoSpin RNA II Kit on cells pellet according to the manufacturer's protocol. Aliquots of 0.4-1 µg were reverse transcribed using Bio-RT 2000 (Bio-Lab) and random hexamer primers. QRT-PCR was performed on an ABI 7300 instrument (Applied Biosystems) using SYBR Green FastMix ROX (Quanta).
RT-PCR primers (All primers sequences are presented 5' to 3'):

Primers List

| Gene | Forward primer/(SEQ ID NO: 20-31) | Reverse primer/(SEQ ID NO: 32-43) |
| --- | --- | --- |
| p53 | CCCAAGCAATGGATGATTTGA | GGCATTCTGGGAGCTTCATCT |
| p21 | GGCAGACCAGCATGACAGATT | GCGGATTAGGGCTTCCTCTT |
| PUMA | GACCTCAACGCACAGTACGAG | AGGAGTCCCATGATGAGATTGT |
| MDM2 | AGGCAAATGTGCAATACCAACA | GGTTACAGCACCATCAGTAGGTACAG |
| CD95 | ACTGTGACCCTTGCACCAAAT | GCCACCCAAGTTAGATCTGG |
| Btg2 | AGGCACTCACAGAGCACTACAAAC | GCCCTTGGACGGCTTTTC |
| GAPDH | ACCCACTCCTCCACCTTTGA | CTGTTGCTGTAGCCAAATTCGT |
| p21 (ChIP) | GTGGCTCTGATTGGCTTTCTG | CTTGGGCTGCCTGTTTTCAG |
| PUMA (ChIP) | GCGAGACTGTGGCCTTGTGTC | ACTTTGTGGACCCTGGAACG |
| MDM2 (ChIP) | GGTTGACTCAGCTTTTCCTCTTG | TATTTAAACCATGCATTTTCC |
| CD95 (ChIP) | GGATAATTAGACGTACGTGGGC | GGACAATTGACAAAATCAGTATC |
| GAPDH (ChIP) | GTATTCCCCCAGGTTTACAT | AGGAGTGAGTGGAAGACAGAA |

NMR

Purified 15N labeled p53 core domain 1 ml 40 µM (aa 94-296) was dialyzed against 1 L of NMR buffer—(157.5 mM sodium phosphate buffer containing 52.5 mM NaCl and 2.625 mM DTT pH 7.2) for 48 h, buffer was changed and sample was dialyzed against 1 L of NMR buffer for an additional 24-48 hour (72 hour in total). 0.5 ml of the sample was subjected to high-resolution NMR. NMR analysis was carried out at the Weizmann institute of science.

Two-dimensional 1H-15N Heteronuclear Single Quantum Coherence (HSQC) spectra of 15N-p53 by itself and when complexed with the peptides as indicated, were recorded at 293 K. Spectra were acquired on a Bruker AVIII-800 NMR spectrometer equipped with a 5 mm inverse detection triple resonance CryoProbe (TCI). Solvent suppression was achieved using WATERGATE sequence.

Example 1 pCAP-250 Synergizes with Cisplatin in Reducing Viability of ES2 Ovarian Cancer Cells ES2 Cells were cultured in 96 wells plates with 3000 cells/well. Serial dilutions of pCAP-250 were added either alone or together with 1 µg/ml of cisplatin and the plates incubated for additional 48 h at 37° C. Then medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm. The viability of ES2 cells treated with 1 µg/ml was 39%. The IC50 for pCAP-250 was estimated at 3.2 µM and in combination with cisplatin the IC50 for pCAP-250 was estimated at 1.9 µM indicating a synergistic effect between the two compounds.

FIG. 1 shows the results of the experiment. Evidently, the viability of the cancer cells reduced significantly in the presence of pCAP 250. A synergy is envisaged by the combined treatment of pCAP 250 with platinum-based chemotherapy.

Example 2

Characterizing the Activity of pCAP-250 and Different Derivatives

Cells, ES2 Con expressing endogenous mp53S241F, and ES2 KO cells in which p53 was stably knocked out using CRISPR/Cas9 (ES2 p53KO), to control for specificity for mutp53 were cultured in 96 wells plates with 3000 cells/well. The indicated peptides were added at a concentration of 8 µg/ml and the plates incubated for additional 48 h at 37° C. Then medium was removed and cell viability was determined by staining the cells with crystal violet (0.05%) in methanol/PBS (1:5, v/v), for 10 min, followed by 3 washes with PBS. 10% acetic acid was added to each well for 10 min. OD was determined at 595 nm.

FIG. 2 shows the difference in the effect of a particular peptide for ES2 Con compared to ES KO indicates specificity of peptide to mutp53 expression. Several peptide derivatives in which amino acids that were substituted to Alanine (Serine and Histidine for example) showed a decreased effect on ES2 Con cells indicating the importance of these amino acids for peptide efficacy.

The results were further augmented in an affinity binding assay as described below.

Example 3 pCAP 250 Binding to p53 DBD

FIGS. 3A-K show microscale thermophoresis analysis for the binding of fluorescently labeled WTp53DBD and pCAP-250. Experiment was performed according to manufacturer instructions; 10 serial dilutions of pCAP-250 were prepared, labeled protein was added to each peptide sample and loaded to capillaries. The samples were analyzed for movement of fluorescent wtp53DBD in temperature gradient with different concentrations of pCAP-250. Microscale thermophoresis analysis results are presented as a curve obtained from manufacturer data analysis software.

Example 4

Pharmacokinetic Study—pCAP 250 Administration Mode and Half Life in Plasma

The results of FIGS. 4A-D show that pCAP 250 (SEQ ID NO: 1) has a plasma half-life of 0.8-1.8 hours when administered intravenously. The results further show that pCAP 250 has a plasma half-life of 3-8 hours when administered subcutaneously.

Example 5

In-Vivo Effect of pCAP-250 Peptide in a Mouse Xenograft Model

FIGS. 5A-D show that pCAP 250 (SEQ ID NO: 1) when administered by intratumoral injections at dose 0.4 mg/kg 3 times a week has a significant effect on tumor development of ES2 cells in ovarian cancer xenograft model. Further shown is that pCAP 250, when administered subcutaneously by Alzet minipumps, a dose of 2.3 mg/kg per day has a significant effect on tumor development of ES2 cells in ovarian cancer xenograft model.

Example 6

Anti-Cancer Activity of pCAP 250 Peptide Variants as Determined by In Vitro Cell Viability Assay

TABLE 3

| SEQ ID NO: | pCAP number | Peptide sequence |
|---|---|---|
| 412 | 483 | myr-RRHSTPHPGE |
| 413 | 485 | myr-RRHSTPHPSE |
| 414 | 488 | myr-RRHSTPHPAD |
| 415 | 489 | myr-RRHSTPHPAE |
| 416 | 504 | myr-RRHSSPHPD |
| 417 | 505 | myr-RRHSVPHPD |
| 418 | 507 | myr-RRHSCPHPD |
| 419 | 513 | myr-RRHSePHPD |
| 420 | 514 | myr-RRHStPHPD |
| 421 | 515 | myr-RRHSsPHPD |
| 422 | 516 | myr-RRHSvPHPD |
| 423 | 518 | myr-RR(L-DAB)STPHPD |
| 424 | 519 | myr-RRHSTP(L-DAB)PD |
| 425 | 530 | myr-RRHSTPHPDD-ch3 |
| 426 | 541 | myr-RRHSTPHAD |
| 427 | 551 | myr-RRHSKPHPD |
| 428 | 552 | myr-RRHSSP(L-DAB)PD |
| 429 | 553 | myr-RRHSvP(L-DAB)PD |
| 430 | 554 | myr-RRHSTP(L-DAB)AD |

TABLE 3-continued

| SEQ ID NO: | pCAP number | Peptide sequence |
|---|---|---|
| 431 | 590 | myr-RRHSsP(L-DAB)PD |
| 432 | 594 | myr-RRHSKPHPDD-NH2 |
| 433 | 595 | myr-RR(L-DAB)STP(L-DAB)PD |
| 434 | 596 | myr-RRHSKP(L-DAB)PD |
| 435 | 597 | myr-RR(L-DAB)SKPHPD |
| 436 | 598 | myr-RR(L-DAB)SKP(L-DAB)PD |
| 437 | 599 | myr-RRHSKPHAD |
| 438 | 600 | myr-RRHSKPHASE |
| 439 | 601 | myr-RRHSKPHPSE |
| 440 | 602 | myr-RR(L-DAB)SsP(L-DAB)PD |
| 441 | 603 | myr-RR(L-DAB)SvP(L-DAB)PD |
| 442 | 606 | myr-RRHSTPHASE |
| 443 | 607 | myr-RRHSkPHPD |
| 444 | 608 | myr-RRHS(L-DAB)PHPD |
| 445 | 609 | myr-RRHS(L-DAB)PHAD |
| 446 | 610 | myr-RRHSEP(L-DAB)PD |
| 447 | 611 | myr-RR(L-DAB)SEPHPD |
| 448 | 622 | myr-RRHSvP(L-DAB)PD-NH2 |
| 449 | 624 | myr-RRHST(Aib)HAD |
| 450 | 630 | myr-RRHSTPHPDIEGR |
| 451 | 632 | myr-RRHSTPHPDIEGRGWQRPSSW |
| 452 | 633 | myr-RR(L-DAB)SEP(L-DAB)PD |
| 453 | 634 | myr-RRHSEP(L-DAB)PD-NH2 |
| 454 | 635 | myr-RR(L-DAB)SEPHPD |
| 455 | 636 | myr-RRHS(PSER)P(L-DAB)PD |
| 456 | 637 | myr-RRHS(pser)P(L-DAB)PD |
| 457 | 638 | myr-RRHS(PSER)P(L-DAB)PD-NH2 |
| 458 | 639 | myr-RRHSKP(L-DAB)PD |
| 459 | 640 | myr-RR(L-DAB)SKPHPD |
| 460 | 642 | myr-RRHSTPHPAH |
| 461 | 643 | myr-RRHSTPHPA(L-DAB) |
| 462 | 644 | myr-RRHSTPHPDH |
| 463 | 645 | myr-RRHSvP(L-DAB)PDH |
| 464 | 646 | myr-RRHSTPHADH |

Table 3: list of 53 pCAP-250 peptide variants. mys stands for myristoyl group, Uppercase and lowercase letters stands for L-type and D-type amino acids respectively. L-DAB stands for L-type Diaminobutyric Acid. PSER and pser stand for L-type and D-type Phosphoserine, respectively. AIB stand for Aminoisobutyric acid.

The peptides were tested in anti-cancer assays on two cell lines. As can be seen in FIGS. 7-8 the indicated peptides are endowed with anti-cancer activity as determined by cell viability (crystal violet viability assay).

Example 7

NMR Experiments of pCAP-250-DBD Complex and its Peptide Variants

NMR experiments (1H-15N HSQC spectra) were performed in order to assess the structural effects that are induced by the binding of the pCAP-250 peptide (PCAP 250) to the p53 DBD. Since residue peak assignment was previously produced for WT DBD (94-312 of SEQ ID NO: 44) [Wong et al. supra], the NMR experiments were conducted using WT DBD (94-296, SEQ ID NO: 44), keeping the same conditions as described by Wong et al [supra].

FIG. 9 presents the NMR peak assignment obtained by Wong et al. (supra) together with the NMR peak map obtained for the free DBD and for the DBD-pCAP 250 complex. From FIG. 9 it can be seen that, in general, the map of Wong et al. (supra) was successfully reproduced despite the differences in the C-terminal lengths of the two DBD constructs, 296 versus 312. Many peak changes in a variety of intensities are observed between the maps of the free DBD and the DBD-pCAP 250, including the disappearing and emerging of a few unassigned peaks, thus clearly providing an indication for binding of pCAP 250 to the WT DBD. Mapping these changes on the DBD structure provides a clear picture regarding the three-dimensional structural region which is influenced by the binding of pCAP 250. This region mainly involves the helix-2 and the L1 loop of DBD-DNA interface motifs and it further extends into the central region of the protein (see magenta in FIG. 10). C277 and R280 are examples of moderate peak movements of residues located on helix-2, where the most dramatic peak movement is observed for G117, located on the L1 loop (see magenta and brown circles in FIG. 9).

Interestingly, the relatively low intensity peaks originally observed by Wong et al. (supra) for H115 and Y126 are not observed for the free DBD, but do appear upon the addition of the pCAP 250 peptide (see yellow circles in FIG. 10). Such a significant difference in the peaks assignment can be considered as the most dominant peak changes induced by pCAP 250. The low intensity of the original peaks and the absence of the peaks from the free DBD spectra indicate that these residues are located in a low stability structural region of the protein, which can adopt more than one dominant stable conformation, and thus is highly sensitive to small changes in protein conditions. Indeed, a dramatic structural reorganization is shown for H115 and Y126 when comparing the top two low energy conformations of a DBD structure solved by NMR (pdb code 2FEJ). Notably, the three-dimensional organization of H115 and Y126 is in close proximity to G117 and can directly affect it, and together these three residues are highly related to the structural integrity of the L1 loop (see FIGS. 11A-B). The appearance of the H115 and Y126 peaks upon peptide addition was further validated by additional NMR experiment using a different pCAP 250 peptide variant, pCAP-615 (RRHSTP{DAB}PD), SEQ ID NO: 465 (see FIG. 12).

The pCAP-553 (myr-RRHSvP(L-DAB)PD, v stands for D-type valine, SEQ ID NO: 429) pCAP 250 peptide variant was found to be two times more potent than P-250 in SW-480 cell-based assays harbouring mutant p53R273H (see FIG. 7). The NMR analysis indicates that pCAP-553 (P553) tends to bind the DBD with improved affinity. This is primarily reflected by the emergence of seven different novel and very strong unassigned peaks at the NMR peak map produced for the DBD-pCAP 553 complex in comparison to the free DBD. Additionally, the shapes of the peaks obtained for the DBD-pCAP 553 complex tend to be more unified and circular, indicating that the binding of the P553 peptide improves the structural stability of the DBD (see FIG. 13).

The NMR experimental results provide evidence for the explicit binding of pCAP 250 and its peptide variants to the WT DBD of the p53 protein. These results support the findings regarding the binding of pCAP 250 to the DBD using the MST methodology (FIGS. 3A-K). The NMR results further indicate that the binding of pCAP 250 and its peptide variants induces structural changes in the DBD, which directly influence the integrity and stability of the DBD-DNA binding interface region, namely the Helix-2 and the L1 loop structural motifs which are essential for the ability of the DBD to bind the DNA. The binding of pCAP 250 and its peptide variants further affects additional residues at the surroundings of the helix 2 and the L1 loop structural motifs, creating a relatively large yet decisive affected patch on the DBD surface.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated peptide comprising the amino acid sequence set forth in SEQ ID NO. 429, wherein said isolated peptide has greater cytotoxicity than pCAP 250 (SEQ ID NO: 1) for cancer cells having mutant p53.

2. The isolated peptide of claim 1 comprising at least one additional amino acid attached to the C-terminus of said amino acid sequence.

3. The isolated peptide of claim 1, further comprising a cell penetrating moiety.

4. The isolated peptide of claim 1, wherein said peptide binds to p53 protein via the p53 consensus DNA binding element comprising the nucleic acid sequences set forth in SEQ ID NO: 55 and 56).

5. The isolated peptide of claim 1, wherein binding of said peptide to a mutant p53 protein at least partially reactivates said mutant p53 protein.

6. The isolated peptide of claim 1, consisting of the amino acid sequence set forth in SEQ ID NO: 429.

7. The isolated peptide of claim 1, wherein said cancer cells having a mutant p53 protein are selected from the group consisting of ES2 ovarian cells and SW480 cells.

8. A method of treating a cancer associated with a mutant p53 protein, comprising administering to a subject in need thereof a therapeutically effective amount of the isolated peptide of claim 1.

9. The method according to claim 8, further comprising administering to the subject in need thereof a therapeutically effective amount of a platin-based chemotherapy.

10. The method according to claim 8, wherein said therapeutically effective amount of the isolated peptide is 0.01-0.3 mg/kg per day.

11. The method according to claim 8, wherein the cancer is selected from the group consisting of breast cancer, colon cancer, ovarian cancer and lung cancer.

* * * * *

SEQUENCE LISTING

```
<160> NUMBER OF SEQ ID NOS: 465

<210> SEQ ID NO 1
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
```

```
<222> LOCATION: (1)..(1)
<223> OTHER INFORMATION: N terminus myristlyated

<400> SEQUENCE: 1

Arg Arg His Ser Thr Pro His Pro Asp
1               5

<210> SEQ ID NO 2
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (9)..(9)
<223> OTHER INFORMATION: Amidated c terminus

<400> SEQUENCE: 2

Arg Arg His Ser Thr Pro His Pro Asp
1               5

<210> SEQ ID NO 3
<211> LENGTH: 7
<212> TYPE: PRT
<213> ORGANISM: Artificial sequence
<220> FEATURE:
<223> OTHER INFORMATION: synthetic peptide

<400> SEQUENCE: 3

His Ser Thr Pro His Pro Asp
1               5

<210> SEQ ID NO 4
<211> LENGTH: 10
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (10)..(10)
<223> OTHER INFORMATION: DOTA conjugate

<400> SEQUENCE: 4

Arg Arg His Ser Thr Pro His Pro Asp Lys
1               5                   10

<210> SEQ ID NO 5
<211> LENGTH: 9
<212> TYPE: PRT
<213> ORGANISM: Artificial sequence
<220> FEATURE:
<223> OTHER INFORMATION: synthetic peptide

<400> SEQUENCE: 5

Arg Arg Ala Ser Thr Pro His Pro Asp
1               5

<210> SEQ ID NO 6
<211> LENGTH: 9
```

```
<212> TYPE: PRT
<213> ORGANISM: Artificial sequence
<220> FEATURE:
<223> OTHER INFORMATION: synthetic peptide

<400> SEQUENCE: 6

Arg Arg His Ala Thr Pro His Pro Asp
1               5

<210> SEQ ID NO 7
<211> LENGTH: 9
<212> TYPE: PRT
<213> ORGANISM: Artificial sequence
<220> FEATURE:
<223> OTHER INFORMATION: synthetic peptide

<400> SEQUENCE: 7

Arg Arg His Ser Ala Pro His Pro Asp
1               5

<210> SEQ ID NO 8
<211> LENGTH: 9
<212> TYPE: PRT
<213> ORGANISM: Artificial sequence
<220> FEATURE:
<223> OTHER INFORMATION: synthetic peptide

<400> SEQUENCE: 8

Arg Arg His Ser Thr Ala His Pro Asp
1               5

<210> SEQ ID NO 9
<211> LENGTH: 9
<212> TYPE: PRT
<213> ORGANISM: Artificial sequence
<220> FEATURE:
<223> OTHER INFORMATION: synthetic peptide

<400> SEQUENCE: 9

Arg Arg His Ser Thr Pro Ala Pro Asp
1               5

<210> SEQ ID NO 10
<211> LENGTH: 9
<212> TYPE: PRT
<213> ORGANISM: Artificial sequence
<220> FEATURE:
<223> OTHER INFORMATION: synthetic peptide

<400> SEQUENCE: 10

Arg Arg His Ser Thr Pro His Ala Asp
1               5

<210> SEQ ID NO 11
<211> LENGTH: 9
<212> TYPE: PRT
<213> ORGANISM: Artificial sequence
<220> FEATURE:
<223> OTHER INFORMATION: synthetic peptide

<400> SEQUENCE: 11

Arg Arg His Ser Thr Pro His Pro Asp
1               5

<210> SEQ ID NO 12
<211> LENGTH: 9
<212> TYPE: PRT
```

```
<213> ORGANISM: Artificial sequence
<220> FEATURE:
<223> OTHER INFORMATION: synthetic peptide

<400> SEQUENCE: 12

Arg Arg His Ser Thr Pro His Pro Ala
1               5

<210> SEQ ID NO 13
<211> LENGTH: 9
<212> TYPE: PRT
<213> ORGANISM: Artificial sequence
<220> FEATURE:
<223> OTHER INFORMATION: synthetic peptide

<400> SEQUENCE: 13

Arg Arg His Ser Thr Pro His Pro Asp
1               5

<210> SEQ ID NO 14
<211> LENGTH: 10
<212> TYPE: PRT
<213> ORGANISM: Artificial sequence
<220> FEATURE:
<223> OTHER INFORMATION: synthetic peptide

<400> SEQUENCE: 14

Arg Arg His Ser Thr Pro His Pro Asp Cys
1               5                   10

<210> SEQ ID NO 15
<211> LENGTH: 10
<212> TYPE: PRT
<213> ORGANISM: Artificial sequence
<220> FEATURE:
<223> OTHER INFORMATION: synthetic peptide

<400> SEQUENCE: 15

Arg Arg His Ser Thr Pro His Pro Asp Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic peptide

<400> SEQUENCE: 16

Arg Arg His Ser Thr Pro His Pro Asp Lys
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation
<220> FEATURE:
<221> NAME/KEY: MISC_FEATURE
<222> LOCATION: (10)..(10)
<223> OTHER INFORMATION: Acetylated C terminus

<400> SEQUENCE: 17
```

Arg Arg His Ser Thr Pro His Pro Asp Lys
1               5                   10

<210> SEQ ID NO 18
<211> LENGTH: 9
<212> TYPE: PRT
<213> ORGANISM: Artificial sequence
<220> FEATURE:
<223> OTHER INFORMATION: synthetic peptide

<400> SEQUENCE: 18

Arg Arg His Ser Thr Pro His Pro Asp
1               5

<210> SEQ ID NO 19
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation
<220> FEATURE:
<221> NAME/KEY: MISC_FEATURE
<222> LOCATION: (9)..(9)
<223> OTHER INFORMATION: Biotin conjugate

<400> SEQUENCE: 19

Arg Arg His Ser Thr Pro His Pro Asp
1               5

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
cccaagcaat ggatgatttg a                                              21

<210> SEQ ID NO 21
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 21
ggcagaccag catgacagat t                                              21

<210> SEQ ID NO 22
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 22
gacctcaacg cacagtacga g                                              21

<210> SEQ ID NO 23
<211> LENGTH: 22
<212> TYPE: DNA
<213> ORGANISM: Artificial sequence
<220> FEATURE:

```
<223> OTHER INFORMATION: Single strand DNA oligonucleotide

<400> SEQUENCE: 23
aggcaaatgt gcaataccaa ca                                              22

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
actgtgaccc ttgcaccaaa t                                               21

<210> SEQ ID NO 25
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 25
aggcactcac agagcactac aaac                                            24

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
acccactcct ccacctttga                                                 20

<210> SEQ ID NO 27
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 27
gtggctctga ttggctttct g                                               21

<210> SEQ ID NO 28
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 28
gcgagactgt ggccttgtgt c                                               21

<210> SEQ ID NO 29
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 29
ggttgactca gcttttcctc ttg                                             23
```

```
<210> SEQ ID NO 30
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 30
ggataattag acgtacgtgg gc                                              22

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
gtattccccc aggtttacat                                                 20

<210> SEQ ID NO 32
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 32
ggcattctgg gagcttcatc t                                               21

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
gcggattagg gcttcctctt                                                 20

<210> SEQ ID NO 34
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 34
aggagtccca tgatgagatt gt                                              22

<210> SEQ ID NO 35
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 35
ggttacagca ccatcagtag gtacag                                          26

<210> SEQ ID NO 36
<211> LENGTH: 21
<212> TYPE: DNA
<213> ORGANISM: Artificial sequence
<220> FEATURE:
<223> OTHER INFORMATION: Single strand DNA oligonucleotide
```

<400> SEQUENCE: 36
gccaccccaa gttagatctg g                                          21

<210> SEQ ID NO 37
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 37
gcccttggac ggcttttc                                              18

<210> SEQ ID NO 38
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 38
ctgttgctgt agccaaattc gt                                         22

<210> SEQ ID NO 39
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 39
cttgggctgc ctgttttcag                                            20

<210> SEQ ID NO 40
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 40
actttgtgga ccctggaacg                                            20

<210> SEQ ID NO 41
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 41
tatttaaacc atgcattttc c                                          21

<210> SEQ ID NO 42
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 42
ggacaattga caaaatcagt atc                                        23

<210> SEQ ID NO 43
<211> LENGTH: 21

```
<212> TYPE: DNA
<213> ORGANISM: Artificial sequence
<220> FEATURE:
<223> OTHER INFORMATION: Single strand DNA oligonucleotide

<400> SEQUENCE: 43
aggagtgagt ggaagacaga a                                              21

<210> SEQ ID NO 44
<211> LENGTH: 393
<212> TYPE: PRT
<213> ORGANISM: homo sapiens

<400> SEQUENCE: 44
```

| Met | Glu | Glu | Pro | Gln | Ser | Asp | Pro | Ser | Val | Glu | Pro | Pro | Leu | Ser | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Thr | Phe | Ser | Asp | Leu | Trp | Lys | Leu | Leu | Pro | Glu | Asn | Asn | Val | Leu |
|     |     |     | 20  |     |     |     |     | 25  |     |     |     |     | 30  |     |     |

| Ser | Pro | Leu | Pro | Ser | Gln | Ala | Met | Asp | Asp | Leu | Met | Leu | Ser | Pro | Asp |
|     |     |     | 35  |     |     |     |     | 40  |     |     |     |     | 45  |     |     |

| Asp | Ile | Glu | Gln | Trp | Phe | Thr | Glu | Asp | Pro | Gly | Pro | Asp | Glu | Ala | Pro |
|     | 50  |     |     |     |     | 55  |     |     |     |     | 60  |     |     |     |     |

| Arg | Met | Pro | Glu | Ala | Ala | Pro | Arg | Val | Ala | Pro | Ala | Pro | Ala | Ala | Pro |
| 65  |     |     |     |     | 70  |     |     |     |     | 75  |     |     |     |     | 80  |

| Thr | Pro | Ala | Ala | Pro | Ala | Pro | Ala | Pro | Ser | Trp | Pro | Leu | Ser | Ser | Ser |
|     |     |     |     | 85  |     |     |     |     | 90  |     |     |     |     | 95  |     |

| Val | Pro | Ser | Gln | Lys | Thr | Tyr | Gln | Gly | Ser | Tyr | Gly | Phe | Arg | Leu | Gly |
|     |     |     |     | 100 |     |     |     |     | 105 |     |     |     |     | 110 |     |

| Phe | Leu | His | Ser | Gly | Thr | Ala | Lys | Ser | Val | Thr | Cys | Thr | Tyr | Ser | Pro |
|     |     |     | 115 |     |     |     |     | 120 |     |     |     |     | 125 |     |     |

| Ala | Leu | Asn | Lys | Met | Phe | Cys | Gln | Leu | Ala | Lys | Thr | Cys | Pro | Val | Gln |
|     | 130 |     |     |     |     | 135 |     |     |     |     | 140 |     |     |     |     |

| Leu | Trp | Val | Asp | Ser | Thr | Pro | Pro | Pro | Gly | Thr | Arg | Val | Arg | Ala | Met |
| 145 |     |     |     |     | 150 |     |     |     |     | 155 |     |     |     |     | 160 |

| Ala | Ile | Tyr | Lys | Gln | Ser | Gln | His | Met | Thr | Glu | Val | Val | Arg | Arg | Cys |
|     |     |     |     | 165 |     |     |     |     | 170 |     |     |     |     | 175 |     |

| Pro | His | His | Glu | Arg | Cys | Ser | Asp | Ser | Asp | Gly | Leu | Ala | Pro | Pro | Gln |
|     |     |     | 180 |     |     |     |     | 185 |     |     |     |     | 190 |     |     |

| His | Leu | Ile | Arg | Val | Glu | Gly | Asn | Leu | Arg | Val | Glu | Tyr | Leu | Asp | Asp |
|     |     |     | 195 |     |     |     |     | 200 |     |     |     |     | 205 |     |     |

| Arg | Asn | Thr | Phe | Arg | His | Ser | Val | Val | Pro | Tyr | Glu | Pro | Pro | Glu |
|     | 210 |     |     |     |     | 215 |     |     |     |     | 220 |     |     |     |

| Val | Gly | Ser | Asp | Cys | Thr | Thr | Ile | His | Tyr | Asn | Tyr | Met | Cys | Asn | Ser |
| 225 |     |     |     |     | 230 |     |     |     |     | 235 |     |     |     |     | 240 |

| Ser | Cys | Met | Gly | Gly | Met | Asn | Arg | Arg | Pro | Ile | Leu | Thr | Ile | Ile | Thr |
|     |     |     |     | 245 |     |     |     |     | 250 |     |     |     |     | 255 |     |

| Leu | Glu | Asp | Ser | Ser | Gly | Asn | Leu | Leu | Gly | Arg | Asn | Ser | Phe | Glu | Val |
|     |     |     | 260 |     |     |     |     | 265 |     |     |     |     | 270 |     |     |

| His | Val | Cys | Ala | Cys | Pro | Gly | Arg | Asp | Arg | Arg | Thr | Glu | Glu | Glu | Asn |
|     | 275 |     |     |     |     | 280 |     |     |     |     | 285 |     |     |     |     |

| Leu | Arg | Lys | Lys | Gly | Glu | Pro | His | His | Glu | Leu | Pro | Pro | Gly | Ser | Thr |
|     | 290 |     |     |     |     | 295 |     |     |     |     | 300 |     |     |     |     |

| Lys | Arg | Ala | Leu | Ser | Asn | Asn | Thr | Ser | Ser | Ser | Pro | Gln | Pro | Lys | Lys |
| 305 |     |     |     |     | 310 |     |     |     |     | 315 |     |     |     |     | 320 |

| Lys | Pro | Leu | Asp | Gly | Glu | Tyr | Phe | Thr | Leu | Gln | Ile | Arg | Gly | Arg | Glu |
|     |     |     |     | 325 |     |     |     |     | 330 |     |     |     |     | 335 |     |

```
Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 45
<211> LENGTH: 199
<212> TYPE: PRT
<213> ORGANISM: homo sapiens

<400> SEQUENCE: 45

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
        35                  40                  45

Pro Val Gln Leu Trp Val Asp Ser Thr Pro Pro Gly Thr Arg Val
    50                  55                  60

Arg Ala Met Ala Ile Tyr Lys Gln Ser Gln His Met Thr Glu Val Val
65                  70                  75                  80

Arg Arg Cys Pro His His Glu Arg Cys Ser Asp Ser Asp Gly Leu Ala
                85                  90                  95

Pro Pro Gln His Leu Ile Arg Val Glu Gly Asn Leu Arg Val Glu Tyr
            100                 105                 110

Leu Asp Asp Arg Asn Thr Phe Arg His Ser Val Val Val Pro Tyr Glu
        115                 120                 125

Pro Pro Glu Val Gly Ser Asp Cys Thr Thr Ile His Tyr Asn Tyr Met
    130                 135                 140

Cys Asn Ser Ser Cys Met Gly Gly Met Asn Arg Arg Pro Ile Leu Thr
145                 150                 155                 160

Ile Ile Thr Leu Glu Asp Ser Ser Gly Asn Leu Leu Gly Arg Asn Ser
                165                 170                 175

Phe Glu Val His Val Cys Ala Cys Pro Gly Arg Asp Arg Arg Thr Glu
            180                 185                 190

Glu Glu Asn Leu Arg Lys Lys
        195

<210> SEQ ID NO 46
<211> LENGTH: 6
<212> TYPE: PRT
<213> ORGANISM: Artificial sequence
<220> FEATURE:
<223> OTHER INFORMATION: synthetic peptide

<400> SEQUENCE: 46

His Ser Ala Pro His Pro
1               5

<210> SEQ ID NO 47
<211> LENGTH: 18
<212> TYPE: RNA
<213> ORGANISM: Artificial sequence
<220> FEATURE:
```

<223> OTHER INFORMATION: single guide RNA (sgRNA)

<400> SEQUENCE: 47
caccgccagc aaacgccg                                              18

<210> SEQ ID NO 48
<211> LENGTH: 19
<212> TYPE: RNA
<213> ORGANISM: Artificial sequence
<220> FEATURE:
<223> OTHER INFORMATION: single guide RNA (sgRNA)

<400> SEQUENCE: 48
aaccggacga agaacaagg                                             19

<210> SEQ ID NO 49
<211> LENGTH: 6
<212> TYPE: PRT
<213> ORGANISM: Artificial sequence
<220> FEATURE:
<223> OTHER INFORMATION: synthetic peptide

<400> SEQUENCE: 49

His Ser Ala Pro His Pro
1               5

<210> SEQ ID NO 50
<211> LENGTH: 6
<212> TYPE: PRT
<213> ORGANISM: Artificial sequence
<220> FEATURE:
<223> OTHER INFORMATION: synthetic peptide

<400> SEQUENCE: 50

His Ser Glu Pro His Pro
1               5

<210> SEQ ID NO 51
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation
<220> FEATURE:
<221> NAME/KEY: MISC_FEATURE
<222> LOCATION: (9)..(9)
<223> OTHER INFORMATION: BSA conjugate

<400> SEQUENCE: 51

Arg Arg His Ser Thr Pro His Pro Asp
1               5

<210> SEQ ID NO 52
<211> LENGTH: 9
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation
<220> FEATURE:
<221> NAME/KEY: MISC_FEATURE
<222> LOCATION: (9)..(9)

<223> OTHER INFORMATION: KLH conjugate

<400> SEQUENCE: 52

Arg Arg His Ser Thr Pro His Pro Asp
1               5

<210> SEQ ID NO 53
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: selected from the group consisting of
      positively charged amino acid
<220> FEATURE:
<221> NAME/KEY: MISC_FEATURE
<222> LOCATION: (2)..(2)
<223> OTHER INFORMATION: selected from the group consisting of Ser, Thr,
      Asn, Gln, Pro, Ala and Gly
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: selected from the group consisting of an alpha
      methyl amino and a beta-breaker amino acid
<220> FEATURE:
<221> NAME/KEY: MISC_FEATURE
<222> LOCATION: (5)..(5)
<223> OTHER INFORMATION: selected from the group consisting of
      positively charged amino acid
<220> FEATURE:
<221> NAME/KEY: MISC_FEATURE
<222> LOCATION: (6)..(6)
<223> OTHER INFORMATION: selected from the group consisting of an alpha
      methyl amino and a beta-breaker amino acid

<400> SEQUENCE: 53

Xaa Xaa Xaa Xaa Xaa Xaa
1               5

<210> SEQ ID NO 54
<211> LENGTH: 6
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: selected from the group consisting of His, Arg
      and Lys
<220> FEATURE:
<221> NAME/KEY: MISC_FEATURE
<222> LOCATION: (2)..(2)
<223> OTHER INFORMATION: selected from the group consisting of Ser, Thr,
      Asn, Gln, Pro, Ala and Gly
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: selected from the group consisting of His, Arg
      and Lys

```
<220> FEATURE:
<221> NAME/KEY: misc_feature
<222> LOCATION: (6)..(6)
<223> OTHER INFORMATION: Xaa can be any amino acid

<400> SEQUENCE: 54

Xaa Xaa Xaa Xaa Xaa Xaa
1               5

<210> SEQ ID NO 55
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 55
catgcccaga catgtccttg ctgctgcgaa catgtcccaa catgttg              47

<210> SEQ ID NO 56
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 56
caacatgttg ggacatgttc gcagcagcaa ggacatgtct gggcatg              47

<210> SEQ ID NO 57
<211> LENGTH: 10
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation
<220> FEATURE:
<221> NAME/KEY: MISC_FEATURE
<222> LOCATION: (10)..(10)
<223> OTHER INFORMATION: folate conjugate

<400> SEQUENCE: 57

Arg Arg His Ser Thr Pro His Pro Asp Lys
1               5                   10

<210> SEQ ID NO 58
<211> LENGTH: 15
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N terminus myristoylation

<400> SEQUENCE: 58

Arg Arg His Ser Thr Pro His Pro Asp His Ala Tyr Pro His Ala
1               5                   10                  15

<210> SEQ ID NO 59
<211> LENGTH: 21
<212> TYPE: PRT
<213> ORGANISM: Artificial
<220> FEATURE:
<223> OTHER INFORMATION: Peptide
```

```
<220> FEATURE:
<221> NAME/KEY: MISC_FEATURE
<222> LOCATION: (12)..(21)
<223> OTHER INFORMATION: X= Arg or absent

<400> SEQUENCE: 59

Ile Arg Ile Leu Met Phe Leu Ile Gly Cys Gly Xaa Xaa Xaa Xaa Xaa
1               5                   10                  15

Xaa Xaa Xaa Xaa Xaa
            20

<210> SEQ ID NO 60
<211> LENGTH: 28
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (19)..(28)
<223> OTHER INFORMATION: X=Arg or absent

<400> SEQUENCE: 60

Leu Arg Cys Leu Leu Leu Leu Ile Gly Arg Val Gly Arg Lys Lys Arg
1               5                   10                  15

Arg Gln Xaa Xaa Xaa Xaa Xaa Xaa Xaa Xaa Xaa Xaa
            20                  25

<210> SEQ ID NO 61
<211> LENGTH: 17
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (8)..(17)
<223> OTHER INFORMATION: X=Arg or absent

<400> SEQUENCE: 61

Tyr Pro Thr Gln Gly His Leu Xaa Xaa Xaa Xaa Xaa Xaa Xaa Xaa Xaa
1               5                   10                  15

Xaa

<210> SEQ ID NO 62
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(22)
<223> OTHER INFORMATION: X=Arg or absent

<400> SEQUENCE: 62

Ser Trp Gln Ala Leu Ala Leu Tyr Ala Ala Gly Trp Xaa Xaa Xaa Xaa
1               5                   10                  15

Xaa Xaa Xaa Xaa Xaa Xaa
            20

<210> SEQ ID NO 63
<211> LENGTH: 20
<212> TYPE: PRT
<213> ORGANISM: Artificial
<220> FEATURE:
<223> OTHER INFORMATION: Peptide
```

```
<220> FEATURE:
<221> NAME/KEY: MISC_FEATURE
<222> LOCATION: (11)..(20)
<223> OTHER INFORMATION: X=Arg or absent

<400> SEQUENCE: 63

Thr Leu Tyr Leu Pro His Trp His Arg His Xaa Xaa Xaa Xaa Xaa Xaa
1               5                   10                  15

Xaa Xaa Xaa Xaa
            20

<210> SEQ ID NO 64
<211> LENGTH: 16
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (7)..(16)
<223> OTHER INFORMATION: X=Arg or absent

<400> SEQUENCE: 64

Ile Arg Gly Arg Ile Ile Xaa Xaa Xaa Xaa Xaa Xaa Xaa Xaa Xaa Xaa
1               5                   10                  15

<210> SEQ ID NO 65
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(22)
<223> OTHER INFORMATION: X=Arg or absent

<400> SEQUENCE: 65

Ser Phe Ile Leu Phe Ile Arg Arg Gly Arg Leu Gly Xaa Xaa Xaa Xaa
1               5                   10                  15

Xaa Xaa Xaa Xaa Xaa Xaa
            20

<210> SEQ ID NO 66
<211> LENGTH: 22
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (13)..(22)
<223> OTHER INFORMATION: X=Arg or absent

<400> SEQUENCE: 66

His Ser Ser His His His Pro Val His Ser Trp Asn Xaa Xaa Xaa Xaa
1               5                   10                  15

Xaa Xaa Xaa Xaa Xaa Xaa
            20

<210> SEQ ID NO 67
<211> LENGTH: 17
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
```

<222> LOCATION: (8)..(17)
<223> OTHER INFORMATION: X=Arg or absent

<400> SEQUENCE: 67

```
His Ala Asn Leu His His Thr Xaa Xaa Xaa Xaa Xaa Xaa Xaa Xaa Xaa
1               5                   10                  15

Xaa
```

<210> SEQ ID NO 68
<211> LENGTH: 20
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (11)..(20)
<223> OTHER INFORMATION: X=Arg or absent

<400> SEQUENCE: 68

```
Trp Asn His His His Ser Thr Pro His Pro Xaa Xaa Xaa Xaa Xaa Xaa
1               5                   10                  15

Xaa Xaa Xaa Xaa
            20
```

<210> SEQ ID NO 69
<211> LENGTH: 16
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
<222> LOCATION: (7)..(16)
<223> OTHER INFORMATION: X=Arg or absent

<400> SEQUENCE: 69

```
His Ser Thr Pro His Pro Xaa Xaa Xaa Xaa Xaa Xaa Xaa Xaa Xaa Xaa
1               5                   10                  15
```

<210> SEQ ID NO 70
<211> LENGTH: 14
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
<222> LOCATION: (5)..(14)
<223> OTHER INFORMATION: X=Arg or absent

<400> SEQUENCE: 70

```
Ser Ile Leu Thr Xaa Xaa Xaa Xaa Xaa Xaa Xaa Xaa Xaa Xaa
1               5                   10
```

<210> SEQ ID NO 71
<211> LENGTH: 20
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (11)..(20)
<223> OTHER INFORMATION: X=Arg or absent

<400> SEQUENCE: 71

```
Tyr Arg Arg Leu Leu Ile Gly Met Met Trp Xaa Xaa Xaa Xaa Xaa Xaa
```

```
1               5                   10                  15

Xaa Xaa Xaa Xaa
            20

<210> SEQ ID NO 72
<211> LENGTH: 20
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
<222> LOCATION: (11)..(20)
<223> OTHER INFORMATION: X=Arg or absent

<400> SEQUENCE: 72

Tyr Arg Arg Leu Leu Ile Gly Met Met Trp Xaa Xaa Xaa Xaa Xaa Xaa
1               5                   10                  15

Xaa Xaa Xaa Xaa
            20

<210> SEQ ID NO 73
<211> LENGTH: 17
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
<222> LOCATION: (8)..(17)
<223> OTHER INFORMATION: X=Arg or absent

<400> SEQUENCE: 73

Phe Pro Gly His Thr Ile His Xaa Xaa Xaa Xaa Xaa Xaa Xaa Xaa Xaa
1               5                   10                  15

Xaa

<210> SEQ ID NO 74
<211> LENGTH: 22
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(10)
<223> OTHER INFORMATION: X=Arg or absent
<220> FEATURE:
<221> NAME/KEY: MISC_FEATURE
<222> LOCATION: (1)..(22)
<223> OTHER INFORMATION: D-amino_acid_peptide

<400> SEQUENCE: 74

Xaa Xaa Xaa Xaa Xaa Xaa Xaa Xaa Xaa Xaa Gly Leu Arg Gly Arg Arg
1               5                   10                  15

Ile Phe Leu Ile Phe Ser
            20

<210> SEQ ID NO 75
<211> LENGTH: 12
<212> TYPE: PRT
<213> ORGANISM: Artificial sequence
<220> FEATURE:
<223> OTHER INFORMATION: Peptide

<400> SEQUENCE: 75

Leu Thr Phe Glu His Tyr Trp Ala Gln Leu Thr Ser
```

<210> SEQ ID NO 76
<211> LENGTH: 12
<212> TYPE: PRT
<213> ORGANISM: Artificial sequence
<220> FEATURE:
<223> OTHER INFORMATION: Peptide

<400> SEQUENCE: 76

Gly Gly Gly Gly Gly Gly Gly Gly Gly Gly Gly Gly
1               5                   10

<210> SEQ ID NO 77
<211> LENGTH: 12
<212> TYPE: PRT
<213> ORGANISM: Artificial sequence
<220> FEATURE:
<223> OTHER INFORMATION: Peptide

<400> SEQUENCE: 77

Asn Pro Asn Thr Tyr Val Pro His Trp Met Arg Gln
1               5                   10

<210> SEQ ID NO 78
<211> LENGTH: 10
<212> TYPE: PRT
<213> ORGANISM: Artificial sequence
<220> FEATURE:
<223> OTHER INFORMATION: peptide

<400> SEQUENCE: 78

Tyr Arg Arg Leu Leu Ile Gly Met Met Trp
1               5                   10

<210> SEQ ID NO 79
<211> LENGTH: 13
<212> TYPE: PRT
<213> ORGANISM: Artificial sequence
<220> FEATURE:
<223> OTHER INFORMATION: peptide

<400> SEQUENCE: 79

Asp Glu Phe His Ser Phe Tyr Thr Ala Arg Gln Thr Gly
1               5                   10

<210> SEQ ID NO 80
<211> LENGTH: 7
<212> TYPE: PRT
<213> ORGANISM: Artificial sequence
<220> FEATURE:
<223> OTHER INFORMATION: Peptide

<400> SEQUENCE: 80

Lys Pro Asp Ser Pro Arg Val
1               5

<210> SEQ ID NO 81
<211> LENGTH: 12
<212> TYPE: PRT
<213> ORGANISM: Artificial sequence
<220> FEATURE:
<223> OTHER INFORMATION: peptide

<400> SEQUENCE: 81

Pro Pro Tyr Ser Gln Phe Leu Gln Trp Tyr Leu Ser
1               5                   10

```
<210> SEQ ID NO 82
<211> LENGTH: 12
<212> TYPE: PRT
<213> ORGANISM: Artificial sequence
<220> FEATURE:
<223> OTHER INFORMATION: peptide

<400> SEQUENCE: 82

Ser Glu Phe Pro Arg Ser Trp Asp Met Glu Thr Asn
1               5                   10

<210> SEQ ID NO 83
<211> LENGTH: 9
<212> TYPE: PRT
<213> ORGANISM: Artificial sequence
<220> FEATURE:
<223> OTHER INFORMATION: peptide

<400> SEQUENCE: 83

His Asp Thr His Asn Ala His Val Gly
1               5

<210> SEQ ID NO 84
<211> LENGTH: 13
<212> TYPE: PRT
<213> ORGANISM: Artificial sequence
<220> FEATURE:
<223> OTHER INFORMATION: peptide

<400> SEQUENCE: 84

Trp Ser Glu Tyr Asp Ile Pro Thr Pro Gln Ile Pro Pro
1               5                   10

<210> SEQ ID NO 85
<211> LENGTH: 16
<212> TYPE: PRT
<213> ORGANISM: Artificial sequence
<220> FEATURE:
<223> OTHER INFORMATION: peptide

<400> SEQUENCE: 85

Ser Ile Leu Thr Leu Ser Arg Arg Arg Arg Arg Arg Arg Arg Arg Arg
1               5                   10                  15

<210> SEQ ID NO 86
<211> LENGTH: 13
<212> TYPE: PRT
<213> ORGANISM: Artificial sequence
<220> FEATURE:
<223> OTHER INFORMATION: peptide

<400> SEQUENCE: 86

Ser Cys Arg Cys Arg Leu Arg Gly Asp Arg Gly Asp Arg
1               5                   10

<210> SEQ ID NO 87
<211> LENGTH: 16
<212> TYPE: PRT
<213> ORGANISM: Artificial sequence
<220> FEATURE:
<223> OTHER INFORMATION: peptide

<400> SEQUENCE: 87

Gly Gly Gly Gly Gly Gly Gly Gly Gly Arg Arg Arg Arg Arg Arg Arg
1               5                   10                  15
```

```
<210> SEQ ID NO 88
<211> LENGTH: 12
<212> TYPE: PRT
<213> ORGANISM: Artificial sequence
<220> FEATURE:
<223> OTHER INFORMATION: peptide

<400> SEQUENCE: 88

Ser Glu Tyr Leu Cys Ser Ser Leu Asp Ala Ala Gly
1               5                   10

<210> SEQ ID NO 89
<211> LENGTH: 12
<212> TYPE: PRT
<213> ORGANISM: Artificial sequence
<220> FEATURE:
<223> OTHER INFORMATION: peptide

<400> SEQUENCE: 89

Gly Glu Ser Phe Val Gln His Val Phe Arg Gln Asn
1               5                   10

<210> SEQ ID NO 90
<211> LENGTH: 12
<212> TYPE: PRT
<213> ORGANISM: Artificial sequence
<220> FEATURE:
<223> OTHER INFORMATION: peptide

<400> SEQUENCE: 90

Ser Val His His His His Arg Met His Leu Val Ala
1               5                   10

<210> SEQ ID NO 91
<211> LENGTH: 7
<212> TYPE: PRT
<213> ORGANISM: Artificial sequence
<220> FEATURE:
<223> OTHER INFORMATION: peptide

<400> SEQUENCE: 91

Gly Arg Arg Arg Phe Cys Met
1               5

<210> SEQ ID NO 92
<211> LENGTH: 7
<212> TYPE: PRT
<213> ORGANISM: Artificial sequence
<220> FEATURE:
<223> OTHER INFORMATION: peptide

<400> SEQUENCE: 92

Lys Leu Thr Ile His His His
1               5

<210> SEQ ID NO 93
<211> LENGTH: 7
<212> TYPE: PRT
<213> ORGANISM: Artificial sequence
<220> FEATURE:
<223> OTHER INFORMATION: peptide

<400> SEQUENCE: 93

Phe Gly Ser His His Glu Leu
1               5
```

```
<210> SEQ ID NO 94
<211> LENGTH: 7
<212> TYPE: PRT
<213> ORGANISM: Artificial sequence
<220> FEATURE:
<223> OTHER INFORMATION: peptide

<400> SEQUENCE: 94

Gly Thr Val Asp His His Ala
1               5

<210> SEQ ID NO 95
<211> LENGTH: 10
<212> TYPE: PRT
<213> ORGANISM: Artificial sequence
<220> FEATURE:
<223> OTHER INFORMATION: peptide

<400> SEQUENCE: 95

Asp Arg Leu Ser Val Phe Leu Phe Ile Met
1               5                   10

<210> SEQ ID NO 96
<211> LENGTH: 7
<212> TYPE: PRT
<213> ORGANISM: Artificial sequence
<220> FEATURE:
<223> OTHER INFORMATION: peptide

<400> SEQUENCE: 96

Ala Ile Ser His His Thr Arg
1               5

<210> SEQ ID NO 97
<211> LENGTH: 12
<212> TYPE: PRT
<213> ORGANISM: Artificial sequence
<220> FEATURE:
<223> OTHER INFORMATION: peptide

<400> SEQUENCE: 97

Lys His His Pro Phe Asp His Arg Leu Gly Asn Gln
1               5                   10

<210> SEQ ID NO 98
<211> LENGTH: 7
<212> TYPE: PRT
<213> ORGANISM: Artificial sequence
<220> FEATURE:
<223> OTHER INFORMATION: peptide

<400> SEQUENCE: 98

His Ser Ala His His Thr Met
1               5

<210> SEQ ID NO 99
<211> LENGTH: 7
<212> TYPE: PRT
<213> ORGANISM: Artificial sequence
<220> FEATURE:
<223> OTHER INFORMATION: peptide

<400> SEQUENCE: 99

Glu Leu Gly Leu His Arg His
1               5

<210> SEQ ID NO 100
```

```
<211> LENGTH: 7
<212> TYPE: PRT
<213> ORGANISM: Artificial sequence
<220> FEATURE:
<223> OTHER INFORMATION: peptide

<400> SEQUENCE: 100

Arg Arg Leu Arg Ile Cys Val
1               5

<210> SEQ ID NO 101
<211> LENGTH: 16
<212> TYPE: PRT
<213> ORGANISM: Artificial sequence
<220> FEATURE:
<223> OTHER INFORMATION: peptide

<400> SEQUENCE: 101

Val Pro His Ile His Glu Phe Thr Arg Arg Arg Arg Arg Arg Arg Arg
1               5                   10                  15

<210> SEQ ID NO 102
<211> LENGTH: 5
<212> TYPE: PRT
<213> ORGANISM: Artificial sequence
<220> FEATURE:
<223> OTHER INFORMATION: peptide

<400> SEQUENCE: 102

Pro Leu Thr Leu Ile
1               5

<210> SEQ ID NO 103
<211> LENGTH: 5
<212> TYPE: PRT
<213> ORGANISM: Artificial sequence
<220> FEATURE:
<223> OTHER INFORMATION: peptide

<400> SEQUENCE: 103

Ser Leu Leu Ile Gly
1               5

<210> SEQ ID NO 104
<211> LENGTH: 5
<212> TYPE: PRT
<213> ORGANISM: Artificial sequence
<220> FEATURE:
<223> OTHER INFORMATION: peptide

<400> SEQUENCE: 104

Lys Pro Pro Glu Arg
1               5

<210> SEQ ID NO 105
<211> LENGTH: 5
<212> TYPE: PRT
<213> ORGANISM: Artificial sequence
<220> FEATURE:
<223> OTHER INFORMATION: peptide

<400> SEQUENCE: 105

Cys Arg Ile Ile Arg
1               5

<210> SEQ ID NO 106
<211> LENGTH: 5
```

```
<212> TYPE: PRT
<213> ORGANISM: Artificial sequence
<220> FEATURE:
<223> OTHER INFORMATION: peptide

<400> SEQUENCE: 106

Ser Phe Ile Leu Ile
1               5

<210> SEQ ID NO 107
<211> LENGTH: 5
<212> TYPE: PRT
<213> ORGANISM: Artificial sequence
<220> FEATURE:
<223> OTHER INFORMATION: peptide

<400> SEQUENCE: 107

Pro His His His Ser
1               5

<210> SEQ ID NO 108
<211> LENGTH: 4
<212> TYPE: PRT
<213> ORGANISM: Artificial sequence
<220> FEATURE:
<223> OTHER INFORMATION: peptide

<400> SEQUENCE: 108

Glu Phe His Ser
1

<210> SEQ ID NO 109
<211> LENGTH: 5
<212> TYPE: PRT
<213> ORGANISM: Artificial sequence
<220> FEATURE:
<223> OTHER INFORMATION: peptide

<400> SEQUENCE: 109

Arg Leu Arg Arg Leu
1               5

<210> SEQ ID NO 110
<211> LENGTH: 4
<212> TYPE: PRT
<213> ORGANISM: Artificial sequence
<220> FEATURE:
<223> OTHER INFORMATION: peptide

<400> SEQUENCE: 110

Asp Ser Pro Arg
1

<210> SEQ ID NO 111
<211> LENGTH: 5
<212> TYPE: PRT
<213> ORGANISM: Artificial sequence
<220> FEATURE:
<223> OTHER INFORMATION: peptide

<400> SEQUENCE: 111

His Pro Trp Thr His
1               5

<210> SEQ ID NO 112
<211> LENGTH: 5
<212> TYPE: PRT
```

```
<213> ORGANISM: Artificial sequence
<220> FEATURE:
<223> OTHER INFORMATION: peptide

<400> SEQUENCE: 112

His Phe Ser His His
1               5

<210> SEQ ID NO 113
<211> LENGTH: 4
<212> TYPE: PRT
<213> ORGANISM: Artificial sequence
<220> FEATURE:
<223> OTHER INFORMATION: peptide

<400> SEQUENCE: 113

Arg Arg Val Ile
1

<210> SEQ ID NO 114
<211> LENGTH: 4
<212> TYPE: PRT
<213> ORGANISM: Artificial sequence
<220> FEATURE:
<223> OTHER INFORMATION: peptide

<400> SEQUENCE: 114

Ile Leu Val Ile
1

<210> SEQ ID NO 115
<211> LENGTH: 16
<212> TYPE: PRT
<213> ORGANISM: Artificial sequence
<220> FEATURE:
<223> OTHER INFORMATION: peptide

<400> SEQUENCE: 115

Arg Arg Ser Arg Ser Asn Glu Asp Val Glu Asp Lys Thr Glu Asp Glu
1               5                   10                  15

<210> SEQ ID NO 116
<211> LENGTH: 19
<212> TYPE: PRT
<213> ORGANISM: Artificial sequence
<220> FEATURE:
<223> OTHER INFORMATION: peptide

<400> SEQUENCE: 116

Arg Arg Ile Arg Ser Gly Gly Lys Asp His Ala Trp Thr Pro Leu His
1               5                   10                  15

Glu Asn His

<210> SEQ ID NO 117
<211> LENGTH: 18
<212> TYPE: PRT
<213> ORGANISM: Artificial sequence
<220> FEATURE:
<223> OTHER INFORMATION: peptide

<400> SEQUENCE: 117

His Thr Pro His Pro Pro Val Ala Arg Thr Ser Pro Leu Gln Thr Pro
1               5                   10                  15

Arg Arg
```

```
<210> SEQ ID NO 118
<211> LENGTH: 13
<212> TYPE: PRT
<213> ORGANISM: Artificial sequence
<220> FEATURE:
<223> OTHER INFORMATION: peptide

<400> SEQUENCE: 118

Pro Asp Ser Glu Pro Pro Arg Met Glu Leu Arg Arg Arg
1               5                   10

<210> SEQ ID NO 119
<211> LENGTH: 13
<212> TYPE: PRT
<213> ORGANISM: Artificial sequence
<220> FEATURE:
<223> OTHER INFORMATION: peptide

<400> SEQUENCE: 119

Arg Arg Asp Thr Phe Asp Ile Arg Ile Leu Met Ala Phe
1               5                   10

<210> SEQ ID NO 120
<211> LENGTH: 15
<212> TYPE: PRT
<213> ORGANISM: Artificial sequence
<220> FEATURE:
<223> OTHER INFORMATION: peptide

<400> SEQUENCE: 120

Arg Arg Glu Val Thr Glu Leu His His Thr His Glu Asp Arg Arg
1               5                   10                  15

<210> SEQ ID NO 121
<211> LENGTH: 12
<212> TYPE: PRT
<213> ORGANISM: Artificial sequence
<220> FEATURE:
<223> OTHER INFORMATION: peptide

<400> SEQUENCE: 121

Ser Pro Trp Thr His Glu Arg Arg Cys Arg Gln Arg
1               5                   10

<210> SEQ ID NO 122
<211> LENGTH: 15
<212> TYPE: PRT
<213> ORGANISM: Artificial sequence
<220> FEATURE:
<223> OTHER INFORMATION: peptide

<400> SEQUENCE: 122

Arg Ser Arg Ser Ser His Leu Arg Asp His Glu Arg Thr His Thr
1               5                   10                  15

<210> SEQ ID NO 123
<211> LENGTH: 15
<212> TYPE: PRT
<213> ORGANISM: Artificial sequence
<220> FEATURE:
<223> OTHER INFORMATION: peptide

<400> SEQUENCE: 123

Arg Arg Arg Ser Thr Asn Thr Phe Leu Gly Glu Asp Phe Asp Gln
1               5                   10                  15

<210> SEQ ID NO 124
```

```
<211> LENGTH: 14
<212> TYPE: PRT
<213> ORGANISM: Artificial sequence
<220> FEATURE:
<223> OTHER INFORMATION: peptide

<400> SEQUENCE: 124

Leu Ile Gly Leu Ser Thr Ser Pro Arg Pro Arg Ile Ile Arg
1               5                   10

<210> SEQ ID NO 125
<211> LENGTH: 20
<212> TYPE: PRT
<213> ORGANISM: Artificial sequence
<220> FEATURE:
<223> OTHER INFORMATION: peptide

<400> SEQUENCE: 125

Glu Ile Tyr Gly Glu Ser Gly Lys Thr Asp Glu His Ala Leu Asp Thr
1               5                   10                  15

Glu Tyr Arg Arg
            20

<210> SEQ ID NO 126
<211> LENGTH: 18
<212> TYPE: PRT
<213> ORGANISM: Artificial sequence
<220> FEATURE:
<223> OTHER INFORMATION: peptide

<400> SEQUENCE: 126

Arg Arg Val Ile Leu Arg Ser Tyr Asp Gly Gly His Ser Thr Pro His
1               5                   10                  15

Pro Asp

<210> SEQ ID NO 127
<211> LENGTH: 18
<212> TYPE: PRT
<213> ORGANISM: Artificial sequence
<220> FEATURE:
<223> OTHER INFORMATION: peptide

<400> SEQUENCE: 127

Thr Gly Lys Thr Phe Val Lys Arg His Leu Thr Glu Phe Glu Lys Lys
1               5                   10                  15

Tyr Arg

<210> SEQ ID NO 128
<211> LENGTH: 20
<212> TYPE: PRT
<213> ORGANISM: Artificial sequence
<220> FEATURE:
<223> OTHER INFORMATION: peptide

<400> SEQUENCE: 128

Asn His Phe Asp Tyr Asp Thr Ile Glu Leu Asp Thr Ala Gly Glu Tyr
1               5                   10                  15

Ser Arg Arg Arg
            20

<210> SEQ ID NO 129
<211> LENGTH: 15
<212> TYPE: PRT
<213> ORGANISM: Artificial sequence
<220> FEATURE:
```

<223> OTHER INFORMATION: peptide

<400> SEQUENCE: 129

Asp Pro Glu Pro Pro Arg Tyr Leu Pro Pro Pro Glu Arg Arg
1               5                   10                  15

<210> SEQ ID NO 130
<211> LENGTH: 20
<212> TYPE: PRT
<213> ORGANISM: Artificial sequence
<220> FEATURE:
<223> OTHER INFORMATION: peptide

<400> SEQUENCE: 130

Arg Arg Thr Phe Ile Arg His Arg Ile Asp Ser Thr Glu Val Ile Tyr
1               5                   10                  15

Gln Asp Glu Asp
            20

<210> SEQ ID NO 131
<211> LENGTH: 17
<212> TYPE: PRT
<213> ORGANISM: Artificial sequence
<220> FEATURE:
<223> OTHER INFORMATION: peptide

<400> SEQUENCE: 131

Glu Ser Lys Thr Gly His Lys Ser Glu Glu Gln Arg Leu Arg Arg Tyr
1               5                   10                  15

Arg

<210> SEQ ID NO 132
<211> LENGTH: 17
<212> TYPE: PRT
<213> ORGANISM: Artificial sequence
<220> FEATURE:
<223> OTHER INFORMATION: peptide

<400> SEQUENCE: 132

Tyr Asp Asp Glu His Asn His His Pro His His Ser Thr His Arg Arg
1               5                   10                  15

Arg

<210> SEQ ID NO 133
<211> LENGTH: 18
<212> TYPE: PRT
<213> ORGANISM: Artificial sequence
<220> FEATURE:
<223> OTHER INFORMATION: peptide

<400> SEQUENCE: 133

Arg Arg Arg Arg Glu Val His Thr Ile His Gln His Gly Ile Val His
1               5                   10                  15

Ser Asp

<210> SEQ ID NO 134
<211> LENGTH: 11
<212> TYPE: PRT
<213> ORGANISM: Artificial sequence
<220> FEATURE:
<223> OTHER INFORMATION: peptide

<400> SEQUENCE: 134

Asp Glu Pro Leu Pro Pro Pro Glu Arg Arg Arg

```
1               5                   10
```

<210> SEQ ID NO 135
<211> LENGTH: 6
<212> TYPE: PRT
<213> ORGANISM: Artificial sequence
<220> FEATURE:
<223> OTHER INFORMATION: peptide

<400> SEQUENCE: 135

```
Ser Pro His Pro Pro Tyr
1               5
```

<210> SEQ ID NO 136
<211> LENGTH: 19
<212> TYPE: PRT
<213> ORGANISM: Artificial sequence
<220> FEATURE:
<223> OTHER INFORMATION: peptide

<400> SEQUENCE: 136

```
Ser Pro His Pro Pro Tyr Ser Pro His Pro Pro Tyr Ser Pro His Pro
1               5                   10                  15
Pro Tyr Pro
```

<210> SEQ ID NO 137
<211> LENGTH: 9
<212> TYPE: PRT
<213> ORGANISM: Artificial sequence
<220> FEATURE:
<223> OTHER INFORMATION: peptide

<400> SEQUENCE: 137

```
Arg Arg Pro His Asn Leu His His Asp
1               5
```

<210> SEQ ID NO 138
<211> LENGTH: 12
<212> TYPE: PRT
<213> ORGANISM: Artificial sequence
<220> FEATURE:
<223> OTHER INFORMATION: peptide

<400> SEQUENCE: 138

```
Leu Arg Asp Pro His Pro Pro Glu Arg Arg Ile Arg
1               5                   10
```

<210> SEQ ID NO 139
<211> LENGTH: 15
<212> TYPE: PRT
<213> ORGANISM: Artificial sequence
<220> FEATURE:
<223> OTHER INFORMATION: peptide

<400> SEQUENCE: 139

```
Arg Arg Pro Ala Asp Gln Ile Ser Tyr Leu His Pro Pro Glu Arg
1               5                   10                  15
```

<210> SEQ ID NO 140
<211> LENGTH: 11
<212> TYPE: PRT
<213> ORGANISM: Artificial sequence
<220> FEATURE:
<223> OTHER INFORMATION: peptide

<400> SEQUENCE: 140

Asp Leu Gln Tyr Asp Phe Pro Arg Ile Arg Arg
1               5                   10

<210> SEQ ID NO 141
<211> LENGTH: 14
<212> TYPE: PRT
<213> ORGANISM: Artificial sequence
<220> FEATURE:
<223> OTHER INFORMATION: peptide

<400> SEQUENCE: 141

Tyr Asp Glu Leu Tyr Gln Lys Glu Asp Pro His Arg Arg Arg
1               5                   10

<210> SEQ ID NO 142
<211> LENGTH: 13
<212> TYPE: PRT
<213> ORGANISM: Artificial sequence
<220> FEATURE:
<223> OTHER INFORMATION: peptide

<400> SEQUENCE: 142

Phe Lys Pro Glu Arg Phe Pro Gln Asn Asp Arg Arg Arg
1               5                   10

<210> SEQ ID NO 143
<211> LENGTH: 8
<212> TYPE: PRT
<213> ORGANISM: Artificial sequence
<220> FEATURE:
<223> OTHER INFORMATION: peptide

<400> SEQUENCE: 143

Arg Pro Ala Asp Arg Ile Arg Arg
1               5

<210> SEQ ID NO 144
<211> LENGTH: 11
<212> TYPE: PRT
<213> ORGANISM: Artificial sequence
<220> FEATURE:
<223> OTHER INFORMATION: peptide

<400> SEQUENCE: 144

His Asp Phe Asp Pro Arg Tyr Arg Asp Arg Arg
1               5                   10

<210> SEQ ID NO 145
<211> LENGTH: 14
<212> TYPE: PRT
<213> ORGANISM: Artificial sequence
<220> FEATURE:
<223> OTHER INFORMATION: peptide

<400> SEQUENCE: 145

Arg Ile Arg Arg Asp Pro Asp Ser Pro Leu Pro His Pro Glu
1               5                   10

<210> SEQ ID NO 146
<211> LENGTH: 15
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

```
<400> SEQUENCE: 146

Arg Arg Ile Arg Ile Leu Met Phe Leu Ile Gly Cys Gly Arg Val
1               5                   10                  15

<210> SEQ ID NO 147
<211> LENGTH: 14
<212> TYPE: PRT
<213> ORGANISM: Artificial sequence
<220> FEATURE:
<223> OTHER INFORMATION: peptide

<400> SEQUENCE: 147

His Pro His Val Ile Leu Pro Arg Ile Arg Ile Arg Ile Arg
1               5                   10

<210> SEQ ID NO 148
<211> LENGTH: 12
<212> TYPE: PRT
<213> ORGANISM: Artificial sequence
<220> FEATURE:
<223> OTHER INFORMATION: peptide

<400> SEQUENCE: 148

Glu Ile His Thr Ile His Leu Leu Pro Glu Arg Arg
1               5                   10

<210> SEQ ID NO 149
<211> LENGTH: 13
<212> TYPE: PRT
<213> ORGANISM: Artificial sequence
<220> FEATURE:
<223> OTHER INFORMATION: peptide

<400> SEQUENCE: 149

Glu Pro Ser His Pro Arg Ser Arg Tyr Pro Arg Thr Phe
1               5                   10

<210> SEQ ID NO 150
<211> LENGTH: 16
<212> TYPE: PRT
<213> ORGANISM: Artificial sequence
<220> FEATURE:
<223> OTHER INFORMATION: peptide

<400> SEQUENCE: 150

Arg Asn Ile Ile Ile Arg Asp Phe Ile His Phe Ser His Ile Asp Arg
1               5                   10                  15

<210> SEQ ID NO 151
<211> LENGTH: 18
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (9)..(10)
<223> OTHER INFORMATION: May have a myristoyl group conjugate

<400> SEQUENCE: 151

Arg Arg Ile Arg Asp Pro Gln Ile Lys Leu Glu Ile His Phe Ser His
1               5                   10                  15

Ile Asp

<210> SEQ ID NO 152
```

```
<211> LENGTH: 12
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 152

Asp Leu His Thr Ile His Ile Pro Arg Asp Arg Arg
1               5                   10

<210> SEQ ID NO 153
<211> LENGTH: 14
<212> TYPE: PRT
<213> ORGANISM: Artificial sequence
<220> FEATURE:
<223> OTHER INFORMATION: peptide

<400> SEQUENCE: 153

Ser His Asp Phe Pro His Arg Glu Pro Arg Pro Glu Arg Arg
1               5                   10

<210> SEQ ID NO 154
<211> LENGTH: 14
<212> TYPE: PRT
<213> ORGANISM: Artificial sequence
<220> FEATURE:
<223> OTHER INFORMATION: peptide

<400> SEQUENCE: 154

Ser Tyr Arg His Tyr Ser Asp His Trp Glu Asp Arg Arg Arg
1               5                   10

<210> SEQ ID NO 155
<211> LENGTH: 20
<212> TYPE: PRT
<213> ORGANISM: Artificial sequence
<220> FEATURE:
<223> OTHER INFORMATION: peptide

<400> SEQUENCE: 155

Val Trp Val His Asp Ser Cys His Ala Asn Leu Gln Asn Tyr Arg Asn
1               5                   10                  15

Tyr Leu Leu Pro
            20

<210> SEQ ID NO 156
<211> LENGTH: 20
<212> TYPE: PRT
<213> ORGANISM: Artificial sequence
<220> FEATURE:
<223> OTHER INFORMATION: peptide

<400> SEQUENCE: 156

Glu His Asp Phe Glu Val Arg Gly Asp Val Val Asn Gly Arg Asn His
1               5                   10                  15

Gln Gly Pro Lys
            20

<210> SEQ ID NO 157
<211> LENGTH: 7
<212> TYPE: PRT
<213> ORGANISM: Artificial sequence
<220> FEATURE:
```

```
<223> OTHER INFORMATION: peptide

<400> SEQUENCE: 157

Leu Glu Val Ile Tyr Met Ile
1               5

<210> SEQ ID NO 158
<211> LENGTH: 7
<212> TYPE: PRT
<213> ORGANISM: Artificial sequence
<220> FEATURE:
<223> OTHER INFORMATION: peptide

<400> SEQUENCE: 158

Trp Thr Leu Ser Asn Tyr Leu
1               5

<210> SEQ ID NO 159
<211> LENGTH: 7
<212> TYPE: PRT
<213> ORGANISM: Artificial sequence
<220> FEATURE:
<223> OTHER INFORMATION: peptide

<400> SEQUENCE: 159

Asp Ser Leu His Ser Thr Tyr
1               5

<210> SEQ ID NO 160
<211> LENGTH: 12
<212> TYPE: PRT
<213> ORGANISM: Artificial sequence
<220> FEATURE:
<223> OTHER INFORMATION: peptide

<400> SEQUENCE: 160

Trp His His Arg Gln Gln Ile Pro Arg Pro Leu Glu
1               5                   10

<210> SEQ ID NO 161
<211> LENGTH: 12
<212> TYPE: PRT
<213> ORGANISM: Artificial sequence
<220> FEATURE:
<223> OTHER INFORMATION: peptide

<400> SEQUENCE: 161

Ala Pro Ser Ile Phe Thr Pro His Ala Trp Arg Gln
1               5                   10

<210> SEQ ID NO 162
<211> LENGTH: 18
<212> TYPE: PRT
<213> ORGANISM: Artificial sequence
<220> FEATURE:
<223> OTHER INFORMATION: peptide

<400> SEQUENCE: 162

Thr His Phe Ser His His Leu Lys Gly Gly Gly Arg Arg Gln Arg Arg
1               5                   10                  15

Arg Pro

<210> SEQ ID NO 163
<211> LENGTH: 18
<212> TYPE: PRT
<213> ORGANISM: Artificial sequence
```

```
<220> FEATURE:
<223> OTHER INFORMATION: peptide

<400> SEQUENCE: 163

Leu His Ser Lys Thr Leu Val Leu Gly Gly Gly Arg Arg Arg Gly
1               5                   10                  15

Asp Arg

<210> SEQ ID NO 164
<211> LENGTH: 19
<212> TYPE: PRT
<213> ORGANISM: Artificial sequence
<220> FEATURE:
<223> OTHER INFORMATION: peptide

<400> SEQUENCE: 164

Trp Thr Leu Ser Asn Tyr Leu Gly Gly Arg Lys Arg Arg Gln Arg
1               5                   10                  15

Arg Arg Arg

<210> SEQ ID NO 165
<211> LENGTH: 12
<212> TYPE: PRT
<213> ORGANISM: Artificial sequence
<220> FEATURE:
<223> OTHER INFORMATION: peptide

<400> SEQUENCE: 165

Val Arg Cys Ile Phe Arg Gly Ile Trp Val Arg Leu
1               5                   10

<210> SEQ ID NO 166
<211> LENGTH: 12
<212> TYPE: PRT
<213> ORGANISM: Artificial sequence
<220> FEATURE:
<223> OTHER INFORMATION: peptide

<400> SEQUENCE: 166

His Ser Ser Gly His Asn Phe Val Leu Val Arg Gln
1               5                   10

<210> SEQ ID NO 167
<211> LENGTH: 7
<212> TYPE: PRT
<213> ORGANISM: Artificial sequence
<220> FEATURE:
<223> OTHER INFORMATION: peptide

<400> SEQUENCE: 167

Leu Phe Ile Leu Val Phe Arg
1               5

<210> SEQ ID NO 168
<211> LENGTH: 7
<212> TYPE: PRT
<213> ORGANISM: Artificial sequence
<220> FEATURE:
<223> OTHER INFORMATION: peptide

<400> SEQUENCE: 168

Thr Thr Ser His His Pro Lys
1               5

<210> SEQ ID NO 169
```

<211> LENGTH: 12
<212> TYPE: PRT
<213> ORGANISM: Artificial sequence
<220> FEATURE:
<223> OTHER INFORMATION: peptide

<400> SEQUENCE: 169

Val Met Val Leu Phe Arg Ile Leu Arg Gly Ser Met
1               5                   10

<210> SEQ ID NO 170
<211> LENGTH: 4
<212> TYPE: PRT
<213> ORGANISM: Artificial sequence
<220> FEATURE:
<223> OTHER INFORMATION: peptide

<400> SEQUENCE: 170

Ser Ile Leu Thr
1

<210> SEQ ID NO 171
<211> LENGTH: 17
<212> TYPE: PRT
<213> ORGANISM: Artificial sequence
<220> FEATURE:
<223> OTHER INFORMATION: peptide

<400> SEQUENCE: 171

Arg Arg Arg Glu Ser Glu Gln Arg Ser Ile Ser Leu His His His Ser
1               5                   10                  15

Thr

<210> SEQ ID NO 172
<211> LENGTH: 16
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 172

His Phe Asn His Tyr Thr Phe Glu Ser Thr Cys Arg Arg Arg Arg Cys
1               5                   10                  15

<210> SEQ ID NO 173
<211> LENGTH: 14
<212> TYPE: PRT
<213> ORGANISM: Artificial sequence
<220> FEATURE:
<223> OTHER INFORMATION: peptide

<400> SEQUENCE: 173

His Ser Thr Pro His Pro Pro Gln Pro Pro Glu Arg Arg Arg
1               5                   10

<210> SEQ ID NO 174
<211> LENGTH: 18
<212> TYPE: PRT
<213> ORGANISM: Artificial sequence
<220> FEATURE:
<223> OTHER INFORMATION: peptide

<400> SEQUENCE: 174

-continued

```
Arg Arg Lys Ser Glu Pro His Ser Leu Ser Gly Gly Tyr Gln Thr Gly
1               5                   10                  15

Ala Asp

<210> SEQ ID NO 175
<211> LENGTH: 21
<212> TYPE: PRT
<213> ORGANISM: Artificial sequence
<220> FEATURE:
<223> OTHER INFORMATION: peptide

<400> SEQUENCE: 175

His Arg Thr Gly His Tyr Thr Arg Cys Arg Gln Arg Cys Arg Ser Arg
1               5                   10                  15

Ser His Asn Arg His
            20

<210> SEQ ID NO 176
<211> LENGTH: 14
<212> TYPE: PRT
<213> ORGANISM: Artificial sequence
<220> FEATURE:
<223> OTHER INFORMATION: peptide

<400> SEQUENCE: 176

Arg Arg Cys Arg Ser Ile Leu Pro Leu Leu Leu Leu Ser Arg
1               5                   10

<210> SEQ ID NO 177
<211> LENGTH: 21
<212> TYPE: PRT
<213> ORGANISM: Artificial sequence
<220> FEATURE:
<223> OTHER INFORMATION: peptide

<400> SEQUENCE: 177

Arg Thr Leu His Gly Arg Arg Val Ile Leu His Glu Gly Gly His Ser
1               5                   10                  15

Ile Ser Asp Leu Lys
            20

<210> SEQ ID NO 178
<211> LENGTH: 18
<212> TYPE: PRT
<213> ORGANISM: Artificial sequence
<220> FEATURE:
<223> OTHER INFORMATION: peptide

<400> SEQUENCE: 178

His His Arg Leu Ser Tyr Phe Ile Val Arg Arg His Ser Thr His Ala
1               5                   10                  15

Ser Arg

<210> SEQ ID NO 179
<211> LENGTH: 10
<212> TYPE: PRT
<213> ORGANISM: Artificial sequence
<220> FEATURE:
<223> OTHER INFORMATION: peptide

<400> SEQUENCE: 179

Arg Arg Ile Arg Ile Asp Pro Gln His Asp
1               5                   10
```

```
<210> SEQ ID NO 180
<211> LENGTH: 11
<212> TYPE: PRT
<213> ORGANISM: Artificial sequence
<220> FEATURE:
<223> OTHER INFORMATION: peptide

<400> SEQUENCE: 180

Ile Leu Gln Pro Asp Phe Leu Ile Arg Pro Glu
1               5                   10

<210> SEQ ID NO 181
<211> LENGTH: 9
<212> TYPE: PRT
<213> ORGANISM: Artificial sequence
<220> FEATURE:
<223> OTHER INFORMATION: peptide

<400> SEQUENCE: 181

His Asp Pro Arg Ile Ile Arg Ile Arg
1               5

<210> SEQ ID NO 182
<211> LENGTH: 7
<212> TYPE: PRT
<213> ORGANISM: Artificial sequence
<220> FEATURE:
<223> OTHER INFORMATION: peptide

<400> SEQUENCE: 182

Ser Pro Tyr Pro Ile Arg Thr
1               5

<210> SEQ ID NO 183
<211> LENGTH: 9
<212> TYPE: PRT
<213> ORGANISM: Artificial sequence
<220> FEATURE:
<223> OTHER INFORMATION: peptide

<400> SEQUENCE: 183

Ile Leu Val Ile Ile Gln Arg Ile Met
1               5

<210> SEQ ID NO 184
<211> LENGTH: 7
<212> TYPE: PRT
<213> ORGANISM: Artificial sequence
<220> FEATURE:
<223> OTHER INFORMATION: peptide

<400> SEQUENCE: 184

Ile Arg Phe Ile Leu Ile Arg
1               5

<210> SEQ ID NO 185
<211> LENGTH: 7
<212> TYPE: PRT
<213> ORGANISM: Artificial sequence
<220> FEATURE:
<223> OTHER INFORMATION: peptide

<400> SEQUENCE: 185

Ser Ser Val His His Arg Gly
1               5

<210> SEQ ID NO 186
```

```
<211> LENGTH: 7
<212> TYPE: PRT
<213> ORGANISM: Artificial sequence
<220> FEATURE:
<223> OTHER INFORMATION: peptide

<400> SEQUENCE: 186

Leu Arg Arg Gln Leu Gln Leu
1               5

<210> SEQ ID NO 187
<211> LENGTH: 7
<212> TYPE: PRT
<213> ORGANISM: Artificial sequence
<220> FEATURE:
<223> OTHER INFORMATION: peptide

<400> SEQUENCE: 187

His Thr Thr Ala His Thr His
1               5

<210> SEQ ID NO 188
<211> LENGTH: 12
<212> TYPE: PRT
<213> ORGANISM: Artificial sequence
<220> FEATURE:
<223> OTHER INFORMATION: peptide

<400> SEQUENCE: 188

His Pro His Asn His Thr Val His Asn Val Val Tyr
1               5                   10

<210> SEQ ID NO 189
<211> LENGTH: 12
<212> TYPE: PRT
<213> ORGANISM: Artificial sequence
<220> FEATURE:
<223> OTHER INFORMATION: peptide

<400> SEQUENCE: 189

Asp His Ser Lys Phe Val Pro Leu Phe Val Arg Gln
1               5                   10

<210> SEQ ID NO 190
<211> LENGTH: 13
<212> TYPE: PRT
<213> ORGANISM: Artificial sequence
<220> FEATURE:
<223> OTHER INFORMATION: peptide

<400> SEQUENCE: 190

Ser Ile Arg Thr Leu Gly Arg Phe Leu Ile Ile Arg Val
1               5                   10

<210> SEQ ID NO 191
<211> LENGTH: 7
<212> TYPE: PRT
<213> ORGANISM: Artificial sequence
<220> FEATURE:
<223> OTHER INFORMATION: peptide

<400> SEQUENCE: 191

Gly Leu Cys Arg Ile Ile Leu
1               5

<210> SEQ ID NO 192
<211> LENGTH: 7
```

```
<212> TYPE: PRT
<213> ORGANISM: Artificial sequence
<220> FEATURE:
<223> OTHER INFORMATION: peptide

<400> SEQUENCE: 192

Ser Pro Pro Ile Arg His His
1               5

<210> SEQ ID NO 193
<211> LENGTH: 14
<212> TYPE: PRT
<213> ORGANISM: Artificial sequence
<220> FEATURE:
<223> OTHER INFORMATION: peptide

<400> SEQUENCE: 193

His Pro Thr His Pro Ile Arg Leu Arg Asp Asn Leu Thr Arg
1               5                   10

<210> SEQ ID NO 194
<211> LENGTH: 12
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 194

Arg Glu Glu Glu Thr Ile Leu Ile Ile Arg Arg Arg
1               5                   10

<210> SEQ ID NO 195
<211> LENGTH: 18
<212> TYPE: PRT
<213> ORGANISM: Artificial sequence
<220> FEATURE:
<223> OTHER INFORMATION: peptide

<400> SEQUENCE: 195

His Thr Ile His Ser Ile Ser Asp Phe Pro Glu Pro Pro Asp Arg Arg
1               5                   10                  15

Arg Arg

<210> SEQ ID NO 196
<211> LENGTH: 20
<212> TYPE: PRT
<213> ORGANISM: Artificial sequence
<220> FEATURE:
<223> OTHER INFORMATION: peptide

<400> SEQUENCE: 196

Asp Glu Asp Ala Ala His Ser Thr Gly His Pro His Asn Ser Gln His
1               5                   10                  15

Arg Arg Arg Arg
            20

<210> SEQ ID NO 197
<211> LENGTH: 12
<212> TYPE: PRT
<213> ORGANISM: Artificial sequence
<220> FEATURE:
<223> OTHER INFORMATION: peptide
```

<400> SEQUENCE: 197

Thr Glu Gln His His Tyr Ile Pro His Arg Arg
1               5                   10

<210> SEQ ID NO 198
<211> LENGTH: 12
<212> TYPE: PRT
<213> ORGANISM: Artificial sequence
<220> FEATURE:
<223> OTHER INFORMATION: peptide

<400> SEQUENCE: 198

Arg Leu Arg Arg Val Ile Leu Arg Ser Tyr His Glu
1               5                   10

<210> SEQ ID NO 199
<211> LENGTH: 19
<212> TYPE: PRT
<213> ORGANISM: Artificial sequence
<220> FEATURE:
<223> OTHER INFORMATION: peptide

<400> SEQUENCE: 199

Glu Glu Pro Asp Arg Gln Pro Ser Gly Lys Arg Gly Gly Arg Lys Arg
1               5                   10                  15

Arg Ser Arg

<210> SEQ ID NO 200
<211> LENGTH: 13
<212> TYPE: PRT
<213> ORGANISM: Artificial sequence
<220> FEATURE:
<223> OTHER INFORMATION: peptide

<400> SEQUENCE: 200

Arg Asp Phe His Thr Ile His Pro Ser Ile Ser Arg Arg
1               5                   10

<210> SEQ ID NO 201
<211> LENGTH: 11
<212> TYPE: PRT
<213> ORGANISM: Artificial sequence
<220> FEATURE:
<223> OTHER INFORMATION: peptide

<400> SEQUENCE: 201

Arg Arg Val Asp Ile His Asp Gly Gln Arg Arg
1               5                   10

<210> SEQ ID NO 202
<211> LENGTH: 10
<212> TYPE: PRT
<213> ORGANISM: Artificial sequence
<220> FEATURE:
<223> OTHER INFORMATION: peptide

<400> SEQUENCE: 202

Asp Gln Pro Tyr Pro His Arg Arg Ile Arg
1               5                   10

<210> SEQ ID NO 203
<211> LENGTH: 13
<212> TYPE: PRT
<213> ORGANISM: Artificial sequence
<220> FEATURE:
<223> OTHER INFORMATION: peptide

```
<220> FEATURE:
<221> NAME/KEY: MISC_FEATURE
<222> LOCATION: (1)..(1)
<223> OTHER INFORMATION: N terminus myristlyated

<400> SEQUENCE: 203

Arg Asp Phe Ile Leu Phe Ile Arg Arg Leu Gly Arg Arg
1               5                   10

<210> SEQ ID NO 204
<211> LENGTH: 10
<212> TYPE: PRT
<213> ORGANISM: Artificial sequence
<220> FEATURE:
<223> OTHER INFORMATION: peptide

<400> SEQUENCE: 204

Leu Asp Leu Tyr His Pro Arg Glu Arg Arg
1               5                   10

<210> SEQ ID NO 205
<211> LENGTH: 12
<212> TYPE: PRT
<213> ORGANISM: Artificial sequence
<220> FEATURE:
<223> OTHER INFORMATION: peptide

<400> SEQUENCE: 205

Arg Arg Ile Arg Asp Pro Leu Gly Asn Glu His Glu
1               5                   10

<210> SEQ ID NO 206
<211> LENGTH: 8
<212> TYPE: PRT
<213> ORGANISM: Artificial sequence
<220> FEATURE:
<223> OTHER INFORMATION: peptide

<400> SEQUENCE: 206

Ile Val Glu Phe Arg Ile Arg Arg
1               5

<210> SEQ ID NO 207
<211> LENGTH: 10
<212> TYPE: PRT
<213> ORGANISM: Artificial sequence
<220> FEATURE:
<223> OTHER INFORMATION: peptide

<400> SEQUENCE: 207

Arg Arg Pro Arg Ile Pro Asp Tyr Ile Leu
1               5                   10

<210> SEQ ID NO 208
<211> LENGTH: 12
<212> TYPE: PRT
<213> ORGANISM: Artificial sequence
<220> FEATURE:
<223> OTHER INFORMATION: peptide

<400> SEQUENCE: 208

Arg Ser Thr Pro His Ile His Glu Phe Ile Arg Arg
1               5                   10

<210> SEQ ID NO 209
<211> LENGTH: 14
<212> TYPE: PRT
```

```
<213> ORGANISM: Artificial sequence
<220> FEATURE:
<223> OTHER INFORMATION: peptide

<400> SEQUENCE: 209

Ser His Asp Phe Tyr Pro His Trp Met Arg Glu Arg Ile Arg
1               5                   10

<210> SEQ ID NO 210
<211> LENGTH: 7
<212> TYPE: PRT
<213> ORGANISM: Artificial sequence
<220> FEATURE:
<223> OTHER INFORMATION: peptide

<400> SEQUENCE: 210

His Phe Ser His His Leu Lys
1               5

<210> SEQ ID NO 211
<211> LENGTH: 8
<212> TYPE: PRT
<213> ORGANISM: Artificial sequence
<220> FEATURE:
<223> OTHER INFORMATION: peptide

<400> SEQUENCE: 211

Thr Ser Pro Leu Gln Ser Leu Lys
1               5

<210> SEQ ID NO 212
<211> LENGTH: 13
<212> TYPE: PRT
<213> ORGANISM: Artificial sequence
<220> FEATURE:
<223> OTHER INFORMATION: peptide

<400> SEQUENCE: 212

Ala Ile Leu Thr Leu Ile Leu Arg Arg Val Ile Trp Pro
1               5                   10

<210> SEQ ID NO 213
<211> LENGTH: 7
<212> TYPE: PRT
<213> ORGANISM: Artificial sequence
<220> FEATURE:
<223> OTHER INFORMATION: peptide

<400> SEQUENCE: 213

Leu Arg Phe Ile Asp Tyr Pro
1               5

<210> SEQ ID NO 214
<211> LENGTH: 10
<212> TYPE: PRT
<213> ORGANISM: Artificial sequence
<220> FEATURE:
<223> OTHER INFORMATION: peptide

<400> SEQUENCE: 214

Gly Pro Ile Lys His His Leu Gln His His
1               5                   10

<210> SEQ ID NO 215
<211> LENGTH: 4
<212> TYPE: PRT
<213> ORGANISM: Artificial sequence
```

```
<220> FEATURE:
<223> OTHER INFORMATION: peptide

<400> SEQUENCE: 215

Leu Thr Leu Ser
1

<210> SEQ ID NO 216
<211> LENGTH: 20
<212> TYPE: PRT
<213> ORGANISM: Artificial sequence
<220> FEATURE:
<223> OTHER INFORMATION: peptide

<400> SEQUENCE: 216

Arg Tyr Glu Glu Asn Asn Gly Val Asn Pro Pro Val Gln Val Phe Glu
1               5                   10                  15

Ser Arg Thr Arg
            20

<210> SEQ ID NO 217
<211> LENGTH: 14
<212> TYPE: PRT
<213> ORGANISM: Artificial sequence
<220> FEATURE:
<223> OTHER INFORMATION: peptide

<400> SEQUENCE: 217

Arg Glu Gly Phe Tyr Gly Pro Trp His Glu Gln Arg Arg Arg
1               5                   10

<210> SEQ ID NO 218
<211> LENGTH: 11
<212> TYPE: PRT
<213> ORGANISM: Artificial sequence
<220> FEATURE:
<223> OTHER INFORMATION: peptide

<400> SEQUENCE: 218

Arg Arg Asp Ile Ile Arg His Asn Ala His Ser
1               5                   10

<210> SEQ ID NO 219
<211> LENGTH: 10
<212> TYPE: PRT
<213> ORGANISM: Artificial sequence
<220> FEATURE:
<223> OTHER INFORMATION: peptide

<400> SEQUENCE: 219

His Asp Phe His Asp Tyr Leu Glu Arg Arg
1               5                   10

<210> SEQ ID NO 220
<211> LENGTH: 10
<212> TYPE: PRT
<213> ORGANISM: Artificial sequence
<220> FEATURE:
<223> OTHER INFORMATION: peptide

<400> SEQUENCE: 220

Ile Arg Glu Phe Asp Pro Arg Arg Ile Arg
1               5                   10

<210> SEQ ID NO 221
<211> LENGTH: 15
```

```
<212> TYPE: PRT
<213> ORGANISM: Artificial sequence
<220> FEATURE:
<223> OTHER INFORMATION: peptide

<400> SEQUENCE: 221

Arg Leu Arg Cys Leu Leu Leu Ile Gly Arg Val Gly Arg Arg
1               5                   10                  15

<210> SEQ ID NO 222
<211> LENGTH: 14
<212> TYPE: PRT
<213> ORGANISM: Artificial sequence
<220> FEATURE:
<223> OTHER INFORMATION: peptide

<400> SEQUENCE: 222

Leu Gly Ile Asp Glu Asp Glu Glu Thr Glu Thr Ala Pro Glu
1               5                   10

<210> SEQ ID NO 223
<211> LENGTH: 12
<212> TYPE: PRT
<213> ORGANISM: Artificial sequence
<220> FEATURE:
<223> OTHER INFORMATION: peptide

<400> SEQUENCE: 223

Ser Leu Leu Ile Gly Phe Gly Ile Ile Arg Ser Arg
1               5                   10

<210> SEQ ID NO 224
<211> LENGTH: 9
<212> TYPE: PRT
<213> ORGANISM: Artificial sequence
<220> FEATURE:
<223> OTHER INFORMATION: peptide

<400> SEQUENCE: 224

Val His Glu Val Thr His His Trp Leu
1               5

<210> SEQ ID NO 225
<211> LENGTH: 7
<212> TYPE: PRT
<213> ORGANISM: Artificial sequence
<220> FEATURE:
<223> OTHER INFORMATION: peptide

<400> SEQUENCE: 225

Ala Thr Pro Phe His Gln Thr
1               5

<210> SEQ ID NO 226
<211> LENGTH: 12
<212> TYPE: PRT
<213> ORGANISM: Artificial sequence
<220> FEATURE:
<223> OTHER INFORMATION: peptide

<400> SEQUENCE: 226

Ser Ile Leu Pro Leu Phe Leu Ile Arg Arg Ser Gly
1               5                   10

<210> SEQ ID NO 227
<211> LENGTH: 16
<212> TYPE: PRT
```

```
<213> ORGANISM: Artificial sequence
<220> FEATURE:
<223> OTHER INFORMATION: peptide

<400> SEQUENCE: 227

Ser Cys Arg Cys Arg Leu Arg Arg Arg Arg Arg Arg Arg Arg
1               5                   10                  15

<210> SEQ ID NO 228
<211> LENGTH: 7
<212> TYPE: PRT
<213> ORGANISM: Artificial sequence
<220> FEATURE:
<223> OTHER INFORMATION: peptide

<400> SEQUENCE: 228

Ser Arg Ile Val Leu Gly Trp
1               5

<210> SEQ ID NO 229
<211> LENGTH: 7
<212> TYPE: PRT
<213> ORGANISM: Artificial sequence
<220> FEATURE:
<223> OTHER INFORMATION: peptide

<400> SEQUENCE: 229

Ser Asn Ile His His Gln Val
1               5

<210> SEQ ID NO 230
<211> LENGTH: 10
<212> TYPE: PRT
<213> ORGANISM: Artificial sequence
<220> FEATURE:
<223> OTHER INFORMATION: peptide

<400> SEQUENCE: 230

Leu Thr Leu Met Arg Leu Arg Ile Ile Gly
1               5                   10

<210> SEQ ID NO 231
<211> LENGTH: 12
<212> TYPE: PRT
<213> ORGANISM: Artificial sequence
<220> FEATURE:
<223> OTHER INFORMATION: peptide

<400> SEQUENCE: 231

His Ser Tyr Ser Pro Tyr Tyr Thr Phe Arg Gln His
1               5                   10

<210> SEQ ID NO 232
<211> LENGTH: 5
<212> TYPE: PRT
<213> ORGANISM: Artificial sequence
<220> FEATURE:
<223> OTHER INFORMATION: peptide

<400> SEQUENCE: 232

Phe Ile Leu Ile Arg
1               5

<210> SEQ ID NO 233
<211> LENGTH: 19
<212> TYPE: PRT
<213> ORGANISM: Artificial sequence
```

```
<220> FEATURE:
<223> OTHER INFORMATION: peptide

<400> SEQUENCE: 233

Arg Cys Arg Asn Arg Lys Lys Glu Lys Thr Glu Cys Leu Gln Lys Glu
1               5                   10                  15

Ser Glu Lys

<210> SEQ ID NO 234
<211> LENGTH: 18
<212> TYPE: PRT
<213> ORGANISM: Artificial sequence
<220> FEATURE:
<223> OTHER INFORMATION: peptide

<400> SEQUENCE: 234

Arg Arg Ile Lys Met Ile Arg Thr Ser Glu Ser Phe Ile Gln His Ile
1               5                   10                  15

Val Ser

<210> SEQ ID NO 235
<211> LENGTH: 17
<212> TYPE: PRT
<213> ORGANISM: Artificial sequence
<220> FEATURE:
<223> OTHER INFORMATION: peptide

<400> SEQUENCE: 235

Arg Arg Val Ser Glu Leu Gln Arg Asn Lys His Gly Arg Lys His Glu
1               5                   10                  15

Leu

<210> SEQ ID NO 236
<211> LENGTH: 19
<212> TYPE: PRT
<213> ORGANISM: Artificial sequence
<220> FEATURE:
<223> OTHER INFORMATION: peptide

<400> SEQUENCE: 236

Arg Arg Arg Leu Asp Asp Glu Asp Val Gln Thr Pro Thr Pro Ser Glu
1               5                   10                  15

Tyr Gln Asn

<210> SEQ ID NO 237
<211> LENGTH: 14
<212> TYPE: PRT
<213> ORGANISM: Artificial sequence
<220> FEATURE:
<223> OTHER INFORMATION: peptide

<400> SEQUENCE: 237

Arg Arg Arg Gln Pro Leu Pro Ser Ala Pro Glu Asn Glu Glu
1               5                   10

<210> SEQ ID NO 238
<211> LENGTH: 20
<212> TYPE: PRT
<213> ORGANISM: Artificial sequence
<220> FEATURE:
<223> OTHER INFORMATION: peptide

<400> SEQUENCE: 238

Ser Pro Leu Gln Thr Pro Ala Ala Pro Gly Ala Ala Ala Gly Pro Ala
```

```
1               5                   10                  15
Leu Ser Pro Val
            20

<210> SEQ ID NO 239
<211> LENGTH: 10
<212> TYPE: PRT
<213> ORGANISM: Artificial sequence
<220> FEATURE:
<223> OTHER INFORMATION: peptide

<400> SEQUENCE: 239

Ser His Gln Val His Thr His His Asn Asn
1               5                   10

<210> SEQ ID NO 240
<211> LENGTH: 7
<212> TYPE: PRT
<213> ORGANISM: Artificial sequence
<220> FEATURE:
<223> OTHER INFORMATION: peptide

<400> SEQUENCE: 240

Lys Leu Gln Val Pro Ile Lys
1               5

<210> SEQ ID NO 241
<211> LENGTH: 20
<212> TYPE: PRT
<213> ORGANISM: Artificial sequence
<220> FEATURE:
<223> OTHER INFORMATION: peptide

<400> SEQUENCE: 241

Ile Arg Gly Arg Ile Ile Arg Arg Lys Lys Arg Arg Gln Arg Arg
1               5                   10                  15

Arg Gly Asp Arg
            20

<210> SEQ ID NO 242
<211> LENGTH: 12
<212> TYPE: PRT
<213> ORGANISM: Artificial sequence
<220> FEATURE:
<223> OTHER INFORMATION: peptide

<400> SEQUENCE: 242

Gln Ile Pro His Arg Ser Ser Thr Ala Leu Gln Leu
1               5                   10

<210> SEQ ID NO 243
<211> LENGTH: 7
<212> TYPE: PRT
<213> ORGANISM: Artificial sequence
<220> FEATURE:
<223> OTHER INFORMATION: peptide

<400> SEQUENCE: 243

Ser Tyr Gln Thr Met Gln Pro
1               5

<210> SEQ ID NO 244
<211> LENGTH: 18
<212> TYPE: PRT
<213> ORGANISM: Artificial sequence
<220> FEATURE:
```

<223> OTHER INFORMATION: peptide

<400> SEQUENCE: 244

Thr Asp Ser His Ser His His Arg Arg Arg Arg Arg Arg Arg Arg
1               5                   10                  15

Arg Arg

<210> SEQ ID NO 245
<211> LENGTH: 21
<212> TYPE: PRT
<213> ORGANISM: Artificial sequence
<220> FEATURE:
<223> OTHER INFORMATION: peptide

<400> SEQUENCE: 245

Ile Pro Met Asn Phe Thr Ser His Ser Leu Arg Gln Arg Arg Arg
1               5                   10                  15

Arg Arg Arg Arg Arg
                20

<210> SEQ ID NO 246
<211> LENGTH: 20
<212> TYPE: PRT
<213> ORGANISM: Artificial sequence
<220> FEATURE:
<223> OTHER INFORMATION: peptide

<400> SEQUENCE: 246

Tyr Trp Ser Ala Pro Gln Pro Ala Thr Arg Arg Arg Arg Arg Arg
1               5                   10                  15

Arg Arg Arg Arg
                20

<210> SEQ ID NO 247
<211> LENGTH: 19
<212> TYPE: PRT
<213> ORGANISM: Artificial sequence
<220> FEATURE:
<223> OTHER INFORMATION: peptide

<400> SEQUENCE: 247

Ser Thr Thr His Pro His Pro Gly Thr Ser Ala Pro Glu Pro Ala Thr
1               5                   10                  15

Arg Arg Arg

<210> SEQ ID NO 248
<211> LENGTH: 12
<212> TYPE: PRT
<213> ORGANISM: Artificial sequence
<220> FEATURE:
<223> OTHER INFORMATION: peptide

<400> SEQUENCE: 248

Asp Asp Ser Asp Asn Arg Ile Ile Arg Tyr Arg Arg
1               5                   10

<210> SEQ ID NO 249
<211> LENGTH: 15
<212> TYPE: PRT
<213> ORGANISM: Artificial sequence
<220> FEATURE:
<223> OTHER INFORMATION: peptide

<400> SEQUENCE: 249

```
Thr Ser Pro His Pro Ser Leu Pro Arg His Ile Tyr Pro Arg Arg
1               5                   10                  15
```

<210> SEQ ID NO 250
<211> LENGTH: 20
<212> TYPE: PRT
<213> ORGANISM: Artificial sequence
<220> FEATURE:
<223> OTHER INFORMATION: peptide

<400> SEQUENCE: 250

```
Arg Arg Ile Thr Glu Ile Arg Gly Arg Thr Gly Lys Thr Thr Leu Thr
1               5                   10                  15

Tyr Ile Glu Asp
            20
```

<210> SEQ ID NO 251
<211> LENGTH: 18
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 251

```
Asp Glu Arg Thr Gly Lys Thr Arg Arg Tyr Ile Asp Thr Arg Asp Ile
1               5                   10                  15

Arg Arg
```

<210> SEQ ID NO 252
<211> LENGTH: 18
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 252

```
Met Thr Tyr Ser Asp Met Pro Arg Arg Ile Ile Thr Asp Glu Asp Arg
1               5                   10                  15

Arg Arg
```

<210> SEQ ID NO 253
<211> LENGTH: 14
<212> TYPE: PRT
<213> ORGANISM: Artificial sequence
<220> FEATURE:
<223> OTHER INFORMATION: peptide

<400> SEQUENCE: 253

```
Arg Arg Tyr Asp Thr Val Ile Asp Asp Ile Glu Tyr Arg Arg
1               5                   10
```

<210> SEQ ID NO 254
<211> LENGTH: 11
<212> TYPE: PRT
<213> ORGANISM: Artificial sequence
<220> FEATURE:
<223> OTHER INFORMATION: peptide

<400> SEQUENCE: 254

Arg Asp Thr Ile Glu Arg Pro Glu Ile Arg Arg
1               5                   10

<210> SEQ ID NO 255
<211> LENGTH: 12
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 255

Arg Tyr Arg Arg Leu Ile Leu Glu Ile Trp Arg Arg
1               5                   10

<210> SEQ ID NO 256
<211> LENGTH: 11
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 256

Arg His Asp Thr His Asn Ala His Ile Arg Arg
1               5                   10

<210> SEQ ID NO 257
<211> LENGTH: 13
<212> TYPE: PRT
<213> ORGANISM: Artificial sequence
<220> FEATURE:
<223> OTHER INFORMATION: peptide

<400> SEQUENCE: 257

Thr His Asp Phe Asp Arg Leu Leu Arg Ile Arg Arg Arg
1               5                   10

<210> SEQ ID NO 258
<211> LENGTH: 10
<212> TYPE: PRT
<213> ORGANISM: Artificial sequence
<220> FEATURE:
<223> OTHER INFORMATION: peptide

<400> SEQUENCE: 258

Arg His Asn His Ile Arg Pro Asp Asn Gln
1               5                   10

<210> SEQ ID NO 259
<211> LENGTH: 11
<212> TYPE: PRT
<213> ORGANISM: Artificial sequence
<220> FEATURE:
<223> OTHER INFORMATION: peptide

<400> SEQUENCE: 259

Arg Tyr Lys Glu Pro Arg Ile Thr Pro Arg Glu
1               5                   10

<210> SEQ ID NO 260

```
<211> LENGTH: 9
<212> TYPE: PRT
<213> ORGANISM: Artificial sequence
<220> FEATURE:
<223> OTHER INFORMATION: peptide

<400> SEQUENCE: 260

Leu Arg Ile Glu Pro Ile Arg Ile Arg
1               5

<210> SEQ ID NO 261
<211> LENGTH: 9
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 261

Arg Leu Ile Arg Ile Arg Ile Leu Met
1               5

<210> SEQ ID NO 262
<211> LENGTH: 14
<212> TYPE: PRT
<213> ORGANISM: Artificial sequence
<220> FEATURE:
<223> OTHER INFORMATION: peptide

<400> SEQUENCE: 262

Arg Pro Glu Phe His Ser Phe His Pro Ile Tyr Glu Arg Arg
1               5                   10

<210> SEQ ID NO 263
<211> LENGTH: 7
<212> TYPE: PRT
<213> ORGANISM: Artificial sequence
<220> FEATURE:
<223> OTHER INFORMATION: peptide

<400> SEQUENCE: 263

Ser Thr Thr His Ile His Ala
1               5

<210> SEQ ID NO 264
<211> LENGTH: 10
<212> TYPE: PRT
<213> ORGANISM: Artificial sequence
<220> FEATURE:
<223> OTHER INFORMATION: peptide

<400> SEQUENCE: 264

Phe Pro His Leu Val Ser Ser Leu Thr Thr
1               5                   10

<210> SEQ ID NO 265
<211> LENGTH: 12
<212> TYPE: PRT
<213> ORGANISM: Artificial sequence
<220> FEATURE:
<223> OTHER INFORMATION: peptide

<400> SEQUENCE: 265

Gly Leu His Leu Phe Thr Thr Asp Arg Gln Gly Trp
1               5                   10
```

<210> SEQ ID NO 266
<211> LENGTH: 17
<212> TYPE: PRT
<213> ORGANISM: Artificial sequence
<220> FEATURE:
<223> OTHER INFORMATION: peptide

<400> SEQUENCE: 266

Asn His Pro Trp Gln Phe Pro Asn Arg Trp Thr Arg Arg Arg Arg
1               5                   10                  15

Arg

<210> SEQ ID NO 267
<211> LENGTH: 19
<212> TYPE: PRT
<213> ORGANISM: Artificial sequence
<220> FEATURE:
<223> OTHER INFORMATION: peptide

<400> SEQUENCE: 267

His Ser Ser His His His Pro Val His Ser Trp Asn Arg Arg Arg
1               5                   10                  15

Arg Arg Arg

<210> SEQ ID NO 268
<211> LENGTH: 13
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 268

Asp Ile His Thr Ile His Leu Pro Asp Thr His Arg Arg
1               5                   10

<210> SEQ ID NO 269
<211> LENGTH: 20
<212> TYPE: PRT
<213> ORGANISM: Artificial sequence
<220> FEATURE:
<223> OTHER INFORMATION: peptide

<400> SEQUENCE: 269

Val Ala Glu Phe Ala Gln Ser Ile Gln Ser Arg Ile Val Glu Trp Lys
1               5                   10                  15

Glu Arg Leu Asp
            20

<210> SEQ ID NO 270
<211> LENGTH: 9
<212> TYPE: PRT
<213> ORGANISM: Artificial sequence
<220> FEATURE:
<223> OTHER INFORMATION: peptide

<400> SEQUENCE: 270

Thr Arg Ile Leu Cys Ile Val Met Met
1               5

<210> SEQ ID NO 271

```
<211> LENGTH: 12
<212> TYPE: PRT
<213> ORGANISM: Artificial sequence
<220> FEATURE:
<223> OTHER INFORMATION: peptide

<400> SEQUENCE: 271

Phe Leu Leu Pro Glu Pro Asp Glu Asn Thr Arg Trp
1               5                   10

<210> SEQ ID NO 272
<211> LENGTH: 7
<212> TYPE: PRT
<213> ORGANISM: Artificial sequence
<220> FEATURE:
<223> OTHER INFORMATION: peptide

<400> SEQUENCE: 272

Leu Met Ser Asn Ala Gln Tyr
1               5

<210> SEQ ID NO 273
<211> LENGTH: 15
<212> TYPE: PRT
<213> ORGANISM: Artificial sequence
<220> FEATURE:
<223> OTHER INFORMATION: peptide

<400> SEQUENCE: 273

Ser Ile Leu Thr Leu Ser Cys Arg Cys Arg Leu Arg Leu Trp Arg
1               5                   10                  15

<210> SEQ ID NO 274
<211> LENGTH: 9
<212> TYPE: PRT
<213> ORGANISM: Artificial sequence
<220> FEATURE:
<223> OTHER INFORMATION: peptide

<400> SEQUENCE: 274

His Gln Ile His Arg Asn His Thr Tyr
1               5

<210> SEQ ID NO 275
<211> LENGTH: 9
<212> TYPE: PRT
<213> ORGANISM: Artificial sequence
<220> FEATURE:
<223> OTHER INFORMATION: peptide

<400> SEQUENCE: 275

Leu Ile Arg Arg Cys Ser Leu Gln Arg
1               5

<210> SEQ ID NO 276
<211> LENGTH: 17
<212> TYPE: PRT
<213> ORGANISM: Artificial sequence
<220> FEATURE:
<223> OTHER INFORMATION: peptide

<400> SEQUENCE: 276

Gly Ala Met His Leu Pro Trp His Met Gly Thr Arg Arg Arg Arg
1               5                   10                  15

Arg
```

```
<210> SEQ ID NO 277
<211> LENGTH: 14
<212> TYPE: PRT
<213> ORGANISM: Artificial sequence
<220> FEATURE:
<223> OTHER INFORMATION: peptide

<400> SEQUENCE: 277

Asp Glu Asp Ala Lys Phe Arg Ile Arg Ile Leu Met Arg Arg
1               5                   10

<210> SEQ ID NO 278
<211> LENGTH: 20
<212> TYPE: PRT
<213> ORGANISM: Artificial sequence
<220> FEATURE:
<223> OTHER INFORMATION: peptide

<400> SEQUENCE: 278

Asn His Ile Thr Asn Gly Gly Glu Glu Asp Ser Asp Cys Ser Ser Arg
1               5                   10                  15

Arg Arg Arg Leu
            20

<210> SEQ ID NO 279
<211> LENGTH: 13
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 279

His Ser Ser His His His Pro Thr Val Gln His Arg Arg
1               5                   10

<210> SEQ ID NO 280
<211> LENGTH: 10
<212> TYPE: PRT
<213> ORGANISM: Artificial sequence
<220> FEATURE:
<223> OTHER INFORMATION: peptide

<400> SEQUENCE: 280

Arg Asp Phe Glu Arg Thr Ile Val Asp Ile
1               5                   10

<210> SEQ ID NO 281
<211> LENGTH: 15
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 281

Arg Arg Arg Glu Ile Leu His Pro Glu Phe Arg Ile Leu Tyr Glu
1               5                   10                  15

<210> SEQ ID NO 282
<211> LENGTH: 9
<212> TYPE: PRT
```

```
<213> ORGANISM: Artificial sequence
<220> FEATURE:
<223> OTHER INFORMATION: peptide

<400> SEQUENCE: 282

His His Phe Ser His His Trp Lys Thr
1               5

<210> SEQ ID NO 283
<211> LENGTH: 7
<212> TYPE: PRT
<213> ORGANISM: Artificial sequence
<220> FEATURE:
<223> OTHER INFORMATION: peptide

<400> SEQUENCE: 283

Phe Leu Ile Arg Arg Ser Gly
1               5

<210> SEQ ID NO 284
<211> LENGTH: 12
<212> TYPE: PRT
<213> ORGANISM: Artificial sequence
<220> FEATURE:
<223> OTHER INFORMATION: peptide

<400> SEQUENCE: 284

His Asn His His His Ser Gln His Thr Pro Gln His
1               5                   10

<210> SEQ ID NO 285
<211> LENGTH: 12
<212> TYPE: PRT
<213> ORGANISM: Artificial sequence
<220> FEATURE:
<223> OTHER INFORMATION: peptide

<400> SEQUENCE: 285

His Leu His Lys His His Tyr Lys Asp Ser Arg Met
1               5                   10

<210> SEQ ID NO 286
<211> LENGTH: 17
<212> TYPE: PRT
<213> ORGANISM: Artificial sequence
<220> FEATURE:
<223> OTHER INFORMATION: peptide

<400> SEQUENCE: 286

His Arg Thr Gln Ser Thr Leu Ile Leu Phe Ile Arg Arg Gly Arg Glu
1               5                   10                  15

Thr

<210> SEQ ID NO 287
<211> LENGTH: 9
<212> TYPE: PRT
<213> ORGANISM: Artificial sequence
<220> FEATURE:
<223> OTHER INFORMATION: peptide

<400> SEQUENCE: 287

Leu His Phe Ser His Ile Asp Arg Arg
1               5

<210> SEQ ID NO 288
<211> LENGTH: 10
```

```
<212> TYPE: PRT
<213> ORGANISM: Artificial sequence
<220> FEATURE:
<223> OTHER INFORMATION: peptide

<400> SEQUENCE: 288

Tyr Glu Leu Pro His His Ala Tyr Pro Ala
1               5                   10

<210> SEQ ID NO 289
<211> LENGTH: 19
<212> TYPE: PRT
<213> ORGANISM: Artificial sequence
<220> FEATURE:
<223> OTHER INFORMATION: peptide

<400> SEQUENCE: 289

Ser Leu Leu Ile Gly Phe Gly Ile Ile Arg Ser Arg Arg Arg Arg
1               5                   10                  15

Arg Arg Arg

<210> SEQ ID NO 290
<211> LENGTH: 17
<212> TYPE: PRT
<213> ORGANISM: Artificial sequence
<220> FEATURE:
<223> OTHER INFORMATION: peptide

<400> SEQUENCE: 290

His Thr Asp Ser His Pro His His His Pro His Arg Arg Arg Arg
1               5                   10                  15

Arg

<210> SEQ ID NO 291
<211> LENGTH: 19
<212> TYPE: PRT
<213> ORGANISM: Artificial sequence
<220> FEATURE:
<223> OTHER INFORMATION: peptide

<400> SEQUENCE: 291

Ala Thr Gln His His Tyr Ile Lys Arg Arg Arg Arg Arg Arg Arg
1               5                   10                  15

Arg Arg Arg

<210> SEQ ID NO 292
<211> LENGTH: 19
<212> TYPE: PRT
<213> ORGANISM: Artificial sequence
<220> FEATURE:
<223> OTHER INFORMATION: peptide

<400> SEQUENCE: 292

Phe Arg Ser Phe Ala Ile Pro Leu Val Val Pro Phe Arg Arg Arg
1               5                   10                  15

Arg Arg Arg

<210> SEQ ID NO 293
<211> LENGTH: 19
<212> TYPE: PRT
<213> ORGANISM: Artificial sequence
<220> FEATURE:
<223> OTHER INFORMATION: peptide

<400> SEQUENCE: 293
```

```
Tyr Pro Thr Gln Gly His Leu Arg Arg Arg Arg Arg Arg Arg Arg
1               5                   10                  15

Arg Arg Arg

<210> SEQ ID NO 294
<211> LENGTH: 18
<212> TYPE: PRT
<213> ORGANISM: Artificial sequence
<220> FEATURE:
<223> OTHER INFORMATION: peptide

<400> SEQUENCE: 294

His Ala Asn Leu His His Thr Arg Arg Arg Arg Arg Arg Arg Arg
1               5                   10                  15

Arg Arg

<210> SEQ ID NO 295
<211> LENGTH: 20
<212> TYPE: PRT
<213> ORGANISM: Artificial sequence
<220> FEATURE:
<223> OTHER INFORMATION: peptide

<400> SEQUENCE: 295

Tyr Arg Arg Leu Leu Ile Gly Met Arg Arg Arg Arg Arg Arg Arg
1               5                   10                  15

Arg Arg Arg Arg
            20

<210> SEQ ID NO 296
<211> LENGTH: 15
<212> TYPE: PRT
<213> ORGANISM: Artificial sequence
<220> FEATURE:
<223> OTHER INFORMATION: peptide

<400> SEQUENCE: 296

Ser His Tyr His Thr Pro Gln Asn Pro Pro Ser Thr Arg Arg Arg
1               5                   10                  15

<210> SEQ ID NO 297
<211> LENGTH: 17
<212> TYPE: PRT
<213> ORGANISM: Artificial sequence
<220> FEATURE:
<223> OTHER INFORMATION: peptide

<400> SEQUENCE: 297

Arg Ser Tyr Ser Lys Leu Leu Cys Leu Leu Glu Arg Leu Arg Ile Ser
1               5                   10                  15

Pro

<210> SEQ ID NO 298
<211> LENGTH: 20
<212> TYPE: PRT
<213> ORGANISM: Artificial sequence
<220> FEATURE:
<223> OTHER INFORMATION: peptide

<400> SEQUENCE: 298

Phe Trp Thr Gln Ser Ile Lys Glu Arg Lys Met Leu Asn Glu His Asp
1               5                   10                  15

Phe Glu Val Arg
```

20

<210> SEQ ID NO 299
<211> LENGTH: 9
<212> TYPE: PRT
<213> ORGANISM: Artificial sequence
<220> FEATURE:
<223> OTHER INFORMATION: peptide

<400> SEQUENCE: 299

Thr His Phe Ser His His Leu Lys His
1               5

<210> SEQ ID NO 300
<211> LENGTH: 7
<212> TYPE: PRT
<213> ORGANISM: Artificial sequence
<220> FEATURE:
<223> OTHER INFORMATION: peptide

<400> SEQUENCE: 300

Ser Cys Arg Cys Arg Leu Arg
1               5

<210> SEQ ID NO 301
<211> LENGTH: 18
<212> TYPE: PRT
<213> ORGANISM: Artificial sequence
<220> FEATURE:
<223> OTHER INFORMATION: peptide

<400> SEQUENCE: 301

Met His Pro Pro Asp Trp Tyr His His Thr Pro Lys Arg Arg Arg
1               5                   10                  15

Arg Arg

<210> SEQ ID NO 302
<211> LENGTH: 21
<212> TYPE: PRT
<213> ORGANISM: Artificial sequence
<220> FEATURE:
<223> OTHER INFORMATION: peptide

<400> SEQUENCE: 302

His Thr Ile His Val His Tyr Pro Gly Asn Arg Gln Pro Asn Pro Pro
1               5                   10                  15

Leu Ile Leu Gln Arg
            20

<210> SEQ ID NO 303
<211> LENGTH: 14
<212> TYPE: PRT
<213> ORGANISM: Artificial sequence
<220> FEATURE:
<223> OTHER INFORMATION: peptide

<400> SEQUENCE: 303

Thr Pro Ser Tyr Gly His Thr Pro Ser His His Arg Arg Arg
1               5                   10

<210> SEQ ID NO 304
<211> LENGTH: 12
<212> TYPE: PRT
<213> ORGANISM: Artificial sequence
<220> FEATURE:
<223> OTHER INFORMATION: peptide

```
<220> FEATURE:
<221> NAME/KEY: MISC_FEATURE
<222> LOCATION: (1)..(1)
<223> OTHER INFORMATION: N terminus myristlyated

<400> SEQUENCE: 304

Ile Arg Gly Arg Ile Arg Ile Arg Arg Ile Arg
1               5                   10

<210> SEQ ID NO 305
<211> LENGTH: 11
<212> TYPE: PRT
<213> ORGANISM: Artificial sequence
<220> FEATURE:
<223> OTHER INFORMATION: peptide

<400> SEQUENCE: 305

His His Pro Trp Thr His His Gln Arg Trp Ser
1               5                   10

<210> SEQ ID NO 306
<211> LENGTH: 12
<212> TYPE: PRT
<213> ORGANISM: Artificial sequence
<220> FEATURE:
<223> OTHER INFORMATION: peptide

<400> SEQUENCE: 306

Ile Pro Met Asn Phe Thr Ser His Ser Leu Arg Gln
1               5                   10

<210> SEQ ID NO 307
<211> LENGTH: 12
<212> TYPE: PRT
<213> ORGANISM: Artificial sequence
<220> FEATURE:
<223> OTHER INFORMATION: peptide

<400> SEQUENCE: 307

Ser Asn His His His Arg His His Thr Asn Thr His
1               5                   10

<210> SEQ ID NO 308
<211> LENGTH: 20
<212> TYPE: PRT
<213> ORGANISM: Artificial sequence
<220> FEATURE:
<223> OTHER INFORMATION: peptide

<400> SEQUENCE: 308

Glu Val Thr Phe Arg His Ser Val Val Arg Arg Arg Arg Arg Arg
1               5                   10                  15

Arg Arg Arg Arg
            20

<210> SEQ ID NO 309
<211> LENGTH: 18
<212> TYPE: PRT
<213> ORGANISM: Artificial sequence
<220> FEATURE:
<223> OTHER INFORMATION: peptide

<400> SEQUENCE: 309

Phe Pro Gly His Thr Ile His Arg Arg Arg Arg Arg Arg Arg Arg
1               5                   10                  15

Arg Arg
```

```
<210> SEQ ID NO 310
<211> LENGTH: 13
<212> TYPE: PRT
<213> ORGANISM: Artificial sequence
<220> FEATURE:
<223> OTHER INFORMATION: peptide

<400> SEQUENCE: 310

Ser Ile Leu Thr Leu Ser Arg Ile Val Leu Gly Trp Trp
1               5                   10

<210> SEQ ID NO 311
<211> LENGTH: 10
<212> TYPE: PRT
<213> ORGANISM: Artificial sequence
<220> FEATURE:
<223> OTHER INFORMATION: peptide

<400> SEQUENCE: 311

Thr Leu Tyr Leu Pro His Trp His Arg His
1               5                   10

<210> SEQ ID NO 312
<211> LENGTH: 18
<212> TYPE: PRT
<213> ORGANISM: Artificial sequence
<220> FEATURE:
<223> OTHER INFORMATION: peptide

<400> SEQUENCE: 312

Ser Ile Leu Thr Leu Arg Leu Arg Arg Leu Arg Arg Arg Arg Arg
1               5                   10                  15

Arg Arg

<210> SEQ ID NO 313
<211> LENGTH: 20
<212> TYPE: PRT
<213> ORGANISM: Artificial sequence
<220> FEATURE:
<223> OTHER INFORMATION: peptide

<400> SEQUENCE: 313

Thr Leu Tyr Leu Pro His Trp His Arg His Arg Arg Arg Arg Arg
1               5                   10                  15

Arg Arg Arg Arg
            20

<210> SEQ ID NO 314
<211> LENGTH: 7
<212> TYPE: PRT
<213> ORGANISM: Artificial sequence
<220> FEATURE:
<223> OTHER INFORMATION: peptide

<400> SEQUENCE: 314

Thr Asp Ser His Ser His His
1               5

<210> SEQ ID NO 315
<211> LENGTH: 20
<212> TYPE: PRT
<213> ORGANISM: Artificial sequence
<220> FEATURE:
<223> OTHER INFORMATION: peptide
```

```
<400> SEQUENCE: 315

Glu Trp Lys Glu Arg Leu Asp Lys Glu Phe Ser Leu Ser Val Tyr Gln
1               5                   10                  15

Lys Met Lys Phe
            20

<210> SEQ ID NO 316
<211> LENGTH: 7
<212> TYPE: PRT
<213> ORGANISM: Artificial sequence
<220> FEATURE:
<223> OTHER INFORMATION: peptide

<400> SEQUENCE: 316

Thr Ile His Pro Ser Ile Ser
1               5

<210> SEQ ID NO 317
<211> LENGTH: 12
<212> TYPE: PRT
<213> ORGANISM: Artificial sequence
<220> FEATURE:
<223> OTHER INFORMATION: peptide

<400> SEQUENCE: 317

Ser Ile Leu Thr Leu Arg Leu Arg Arg Leu Arg Arg
1               5                   10

<210> SEQ ID NO 318
<211> LENGTH: 8
<212> TYPE: PRT
<213> ORGANISM: Artificial sequence
<220> FEATURE:
<223> OTHER INFORMATION: peptide

<400> SEQUENCE: 318

Val Pro His Ile His Glu Phe Thr
1               5

<210> SEQ ID NO 319
<211> LENGTH: 13
<212> TYPE: PRT
<213> ORGANISM: Artificial sequence
<220> FEATURE:
<223> OTHER INFORMATION: peptide

<400> SEQUENCE: 319

Thr Ile Ile His Arg Glu Asp Glu Asp Glu Ile Glu Trp
1               5                   10

<210> SEQ ID NO 320
<211> LENGTH: 12
<212> TYPE: PRT
<213> ORGANISM: Artificial sequence
<220> FEATURE:
<223> OTHER INFORMATION: peptide

<400> SEQUENCE: 320

Lys Asp Leu Pro Phe Tyr Ser His Leu Ser Arg Gln
1               5                   10

<210> SEQ ID NO 321
<211> LENGTH: 19
<212> TYPE: PRT
<213> ORGANISM: Artificial sequence
<220> FEATURE:
```

<223> OTHER INFORMATION: peptide

<400> SEQUENCE: 321

Thr His Phe Ser His His Leu Lys His Arg Arg Arg Arg Arg Arg
1               5                   10                  15

Arg Arg Arg

<210> SEQ ID NO 322
<211> LENGTH: 8
<212> TYPE: PRT
<213> ORGANISM: Artificial sequence
<220> FEATURE:
<223> OTHER INFORMATION: peptide

<400> SEQUENCE: 322

Ala Thr Gln His His Tyr Ile Lys
1               5

<210> SEQ ID NO 323
<211> LENGTH: 12
<212> TYPE: PRT
<213> ORGANISM: Artificial sequence
<220> FEATURE:
<223> OTHER INFORMATION: peptide

<400> SEQUENCE: 323

Ile Ile Arg Gly Asn Phe Leu Ile Gly Gly Arg Leu
1               5                   10

<210> SEQ ID NO 324
<211> LENGTH: 20
<212> TYPE: PRT
<213> ORGANISM: Artificial sequence
<220> FEATURE:
<223> OTHER INFORMATION: peptide

<400> SEQUENCE: 324

Leu Pro Asn Pro Pro Glu Arg His His Arg Arg Arg Arg Arg Arg
1               5                   10                  15

Arg Arg Arg Arg
            20

<210> SEQ ID NO 325
<211> LENGTH: 16
<212> TYPE: PRT
<213> ORGANISM: Artificial sequence
<220> FEATURE:
<223> OTHER INFORMATION: peptide

<400> SEQUENCE: 325

Ser Phe Ile Leu Phe Ile Arg Arg Gly Arg Leu Gly Arg Gly Asp Arg
1               5                   10                  15

<210> SEQ ID NO 326
<211> LENGTH: 7
<212> TYPE: PRT
<213> ORGANISM: Artificial sequence
<220> FEATURE:
<223> OTHER INFORMATION: peptide

<400> SEQUENCE: 326

Phe Pro Gly His Thr Ile His
1               5

<210> SEQ ID NO 327

```
<211> LENGTH: 7
<212> TYPE: PRT
<213> ORGANISM: Artificial sequence
<220> FEATURE:
<223> OTHER INFORMATION: peptide

<400> SEQUENCE: 327

Cys Ile Leu Arg Leu Trp Trp
1               5

<210> SEQ ID NO 328
<211> LENGTH: 16
<212> TYPE: PRT
<213> ORGANISM: Artificial sequence
<220> FEATURE:
<223> OTHER INFORMATION: peptide

<400> SEQUENCE: 328

Arg Arg Arg Ser His Ser Gln Glu Asn Val Asp Gln Asp Thr Asp Glu
1               5                   10                  15

<210> SEQ ID NO 329
<211> LENGTH: 18
<212> TYPE: PRT
<213> ORGANISM: Artificial sequence
<220> FEATURE:
<223> OTHER INFORMATION: peptide

<400> SEQUENCE: 329

Met Ser Thr Glu Ser Asn Met Pro Arg Leu Ile Gln Asn Asp Asp Arg
1               5                   10                  15

Arg Arg

<210> SEQ ID NO 330
<211> LENGTH: 7
<212> TYPE: PRT
<213> ORGANISM: Artificial sequence
<220> FEATURE:
<223> OTHER INFORMATION: peptide

<400> SEQUENCE: 330

Leu Leu Arg Leu Gly Leu Ile
1               5

<210> SEQ ID NO 331
<211> LENGTH: 12
<212> TYPE: PRT
<213> ORGANISM: Artificial sequence
<220> FEATURE:
<223> OTHER INFORMATION: peptide

<400> SEQUENCE: 331

Ile Arg Ile Leu Met Phe Leu Ile Gly Cys Gly Arg
1               5                   10

<210> SEQ ID NO 332
<211> LENGTH: 8
<212> TYPE: PRT
<213> ORGANISM: Artificial sequence
<220> FEATURE:
<223> OTHER INFORMATION: peptide

<400> SEQUENCE: 332

Leu His Ser Lys Thr Leu Val Leu
1               5
```

```
<210> SEQ ID NO 333
<211> LENGTH: 12
<212> TYPE: PRT
<213> ORGANISM: Artificial sequence
<220> FEATURE:
<223> OTHER INFORMATION: peptide

<400> SEQUENCE: 333

Leu Arg Cys Leu Leu Leu Ile Gly Arg Val Gly
1               5                   10

<210> SEQ ID NO 334
<211> LENGTH: 12
<212> TYPE: PRT
<213> ORGANISM: Artificial sequence
<220> FEATURE:
<223> OTHER INFORMATION: peptide

<400> SEQUENCE: 334

Phe Leu Ile Gly Pro Asp Arg Leu Ile Arg Ser Arg
1               5                   10

<210> SEQ ID NO 335
<211> LENGTH: 9
<212> TYPE: PRT
<213> ORGANISM: Artificial sequence
<220> FEATURE:
<223> OTHER INFORMATION: peptide

<400> SEQUENCE: 335

Leu Pro Asn Pro Pro Glu Arg His His
1               5

<210> SEQ ID NO 336
<211> LENGTH: 12
<212> TYPE: PRT
<213> ORGANISM: Artificial sequence
<220> FEATURE:
<223> OTHER INFORMATION: peptide

<400> SEQUENCE: 336

His Thr Asp Ser His Pro His His His His Pro His
1               5                   10

<210> SEQ ID NO 337
<211> LENGTH: 21
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus Fluorescein isothiocyanate (FITC)
      labeled

<400> SEQUENCE: 337

Ser Phe Ile Leu Phe Ile Arg Arg Gly Arg Leu Gly Arg Arg Arg
1               5                   10                  15

Arg Arg Arg Arg Arg
                20

<210> SEQ ID NO 338
<211> LENGTH: 12
<212> TYPE: PRT
<213> ORGANISM: Artificial sequence
<220> FEATURE:
<223> OTHER INFORMATION: peptide
```

```
<400> SEQUENCE: 338

His Ser Ser His His Pro Val His Ser Trp Asn
1               5                   10

<210> SEQ ID NO 339
<211> LENGTH: 17
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 339

Arg Thr Leu Ile Gly Ile Ile Arg Ser His His Leu Thr Leu Ile Arg
1               5                   10                  15

Arg

<210> SEQ ID NO 340
<211> LENGTH: 7
<212> TYPE: PRT
<213> ORGANISM: Artificial sequence
<220> FEATURE:
<223> OTHER INFORMATION: peptide

<400> SEQUENCE: 340

Ile Arg Gly Arg Ile Ile Arg
1               5

<210> SEQ ID NO 341
<211> LENGTH: 21
<212> TYPE: PRT
<213> ORGANISM: Artificial sequence
<220> FEATURE:
<223> OTHER INFORMATION: peptide

<400> SEQUENCE: 341

Ile Ile Arg Gly Asn Phe Leu Ile Gly Gly Arg Leu Arg Arg Arg Arg
1               5                   10                  15

Arg Arg Arg Arg Arg
            20

<210> SEQ ID NO 342
<211> LENGTH: 5
<212> TYPE: PRT
<213> ORGANISM: Artificial sequence
<220> FEATURE:
<223> OTHER INFORMATION: peptide

<400> SEQUENCE: 342

Ile Arg Ile Leu Met
1               5

<210> SEQ ID NO 343
<211> LENGTH: 12
<212> TYPE: PRT
<213> ORGANISM: Artificial sequence
<220> FEATURE:
<223> OTHER INFORMATION: peptide

<400> SEQUENCE: 343

Gly Ala Met His Leu Pro Trp His Met Gly Thr Leu
1               5                   10
```

<210> SEQ ID NO 344
<211> LENGTH: 20
<212> TYPE: PRT
<213> ORGANISM: Artificial sequence
<220> FEATURE:
<223> OTHER INFORMATION: peptide

<400> SEQUENCE: 344

Lys Arg Gly Gly Arg Lys Arg Arg Gly Gly His Arg Leu Ser Tyr
1               5                   10                  15

Phe Ile Arg Arg
            20

<210> SEQ ID NO 345
<211> LENGTH: 12
<212> TYPE: PRT
<213> ORGANISM: Artificial sequence
<220> FEATURE:
<223> OTHER INFORMATION: peptide

<400> SEQUENCE: 345

Asn His Pro Trp Gln Phe Pro Asn Arg Trp Thr Val
1               5                   10

<210> SEQ ID NO 346
<211> LENGTH: 13
<212> TYPE: PRT
<213> ORGANISM: Artificial sequence
<220> FEATURE:
<223> OTHER INFORMATION: peptide

<400> SEQUENCE: 346

Met His Pro Pro Asp Trp Tyr His His Thr Pro Lys His
1               5                   10

<210> SEQ ID NO 347
<211> LENGTH: 18
<212> TYPE: PRT
<213> ORGANISM: Artificial sequence
<220> FEATURE:
<223> OTHER INFORMATION: peptide

<400> SEQUENCE: 347

Ser Trp Gln Ala Leu Ala Leu Tyr Ala Ala Gly Trp Arg Arg Arg
1               5                   10                  15

Arg Arg

<210> SEQ ID NO 348
<211> LENGTH: 4
<212> TYPE: PRT
<213> ORGANISM: Artificial sequence
<220> FEATURE:
<223> OTHER INFORMATION: peptide

<400> SEQUENCE: 348

His Asn Ala His
1

<210> SEQ ID NO 349
<211> LENGTH: 15
<212> TYPE: PRT
<213> ORGANISM: Artificial sequence
<220> FEATURE:
<223> OTHER INFORMATION: peptide

```
<400> SEQUENCE: 349

Asp Glu Phe Glu Arg Tyr Arg Arg Phe Ser Thr Ser Arg Arg Arg
1               5                   10                  15

<210> SEQ ID NO 350
<211> LENGTH: 9
<212> TYPE: PRT
<213> ORGANISM: Artificial sequence
<220> FEATURE:
<223> OTHER INFORMATION: peptide

<400> SEQUENCE: 350

Glu Val Thr Phe Arg His Ser Val Val
1               5

<210> SEQ ID NO 351
<211> LENGTH: 20
<212> TYPE: PRT
<213> ORGANISM: Artificial sequence
<220> FEATURE:
<223> OTHER INFORMATION: peptide

<400> SEQUENCE: 351

Thr Arg Ile Leu Cys Ile Val Arg Lys Lys Arg Gln Arg Arg
1               5                   10                  15

Arg Gly Asp Arg
            20

<210> SEQ ID NO 352
<211> LENGTH: 18
<212> TYPE: PRT
<213> ORGANISM: Artificial sequence
<220> FEATURE:
<223> OTHER INFORMATION: peptide

<400> SEQUENCE: 352

Ser Ile Leu Thr Leu Ser Arg Gly Arg Lys Lys Arg Arg Gln Arg Arg
1               5                   10                  15

Arg Arg

<210> SEQ ID NO 353
<211> LENGTH: 18
<212> TYPE: PRT
<213> ORGANISM: Artificial sequence
<220> FEATURE:
<223> OTHER INFORMATION: peptide

<400> SEQUENCE: 353

Cys Ile Leu Arg Leu Trp Trp Arg Arg Arg Arg Arg Arg Arg Arg Arg
1               5                   10                  15

Arg Arg

<210> SEQ ID NO 354
<211> LENGTH: 13
<212> TYPE: PRT
<213> ORGANISM: Artificial sequence
<220> FEATURE:
<223> OTHER INFORMATION: peptide

<400> SEQUENCE: 354

Ala Ser Trp Gln Ala Leu Ala Leu Tyr Ala Ala Gly Trp
1               5                   10

<210> SEQ ID NO 355
```

```
<211> LENGTH: 16
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 355

Pro Arg Val Leu Pro Ser Pro His Thr Ile His Pro Ser Gln Tyr Pro
1               5                   10                  15

<210> SEQ ID NO 356
<211> LENGTH: 7
<212> TYPE: PRT
<213> ORGANISM: Artificial sequence
<220> FEATURE:
<223> OTHER INFORMATION: peptide

<400> SEQUENCE: 356

His Ala Asn Leu His His Thr
1               5

<210> SEQ ID NO 357
<211> LENGTH: 22
<212> TYPE: PRT
<213> ORGANISM: Artificial sequence
<220> FEATURE:
<223> OTHER INFORMATION: peptide

<400> SEQUENCE: 357

Ser Phe Ile Leu Phe Ile Arg Arg Gly Arg Leu Gly Arg Lys Lys Arg
1               5                   10                  15

Arg Gln Arg Arg Arg Pro
            20

<210> SEQ ID NO 358
<211> LENGTH: 8
<212> TYPE: PRT
<213> ORGANISM: Artificial sequence
<220> FEATURE:
<223> OTHER INFORMATION: peptide

<400> SEQUENCE: 358

Tyr Pro Thr Gln Gly His Leu Arg
1               5

<210> SEQ ID NO 359
<211> LENGTH: 21
<212> TYPE: PRT
<213> ORGANISM: Artificial sequence
<220> FEATURE:
<223> OTHER INFORMATION: peptide

<400> SEQUENCE: 359

Tyr Arg Arg Leu Leu Ile Gly Met Met Trp Arg Arg Arg Arg Arg Arg
1               5                   10                  15

Arg Arg Arg Arg Arg
            20

<210> SEQ ID NO 360
<211> LENGTH: 12
<212> TYPE: PRT
<213> ORGANISM: Artificial sequence
<220> FEATURE:
```

<223> OTHER INFORMATION: peptide

<400> SEQUENCE: 360

Ser Phe Ile Leu Phe Ile Arg Arg Gly Arg Leu Gly
1               5                   10

<210> SEQ ID NO 361
<211> LENGTH: 19
<212> TYPE: PRT
<213> ORGANISM: Artificial sequence
<220> FEATURE:
<223> OTHER INFORMATION: peptide

<400> SEQUENCE: 361

Ile Arg Ile Leu Met Phe Leu Ile Gly Cys Gly Arg Arg Arg Arg
1               5                   10                  15

Arg Arg Arg

<210> SEQ ID NO 362
<211> LENGTH: 13
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 362

Arg Arg Ile Cys Arg Phe Ile Arg Ile Cys Arg Val Arg
1               5                   10

<210> SEQ ID NO 363
<211> LENGTH: 16
<212> TYPE: PRT
<213> ORGANISM: Artificial sequence
<220> FEATURE:
<223> OTHER INFORMATION: peptide

<400> SEQUENCE: 363

Ile Arg Gly Arg Ile Ile Arg Arg Arg Arg Arg Arg Arg Arg Arg Arg
1               5                   10                  15

<210> SEQ ID NO 364
<211> LENGTH: 19
<212> TYPE: PRT
<213> ORGANISM: Artificial sequence
<220> FEATURE:
<223> OTHER INFORMATION: peptide

<400> SEQUENCE: 364

Arg Arg Arg His Asp Ser Cys His Asn Gln Leu Gln Asn Tyr Asp His
1               5                   10                  15

Ser Thr Glu

<210> SEQ ID NO 365
<211> LENGTH: 20
<212> TYPE: PRT
<213> ORGANISM: Artificial sequence
<220> FEATURE:
<223> OTHER INFORMATION: peptide

<400> SEQUENCE: 365

Trp Asn His His His Ser Thr Pro His Pro Arg Arg Arg Arg Arg
1               5                   10                  15

Arg Arg Arg Arg
            20

<210> SEQ ID NO 366
<211> LENGTH: 18
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 366

Arg Arg Pro Val Ala Pro Asp Leu Arg His Thr Ile His Ile Pro Pro
1               5                   10                  15

Glu Arg

<210> SEQ ID NO 367
<211> LENGTH: 12
<212> TYPE: PRT
<213> ORGANISM: Artificial sequence
<220> FEATURE:
<223> OTHER INFORMATION: peptide

<400> SEQUENCE: 367

Arg Arg Asp Ile His Thr Ile His Pro Phe Tyr Gln
1               5                   10

<210> SEQ ID NO 368
<211> LENGTH: 12
<212> TYPE: PRT
<213> ORGANISM: Artificial sequence
<220> FEATURE:
<223> OTHER INFORMATION: peptide

<400> SEQUENCE: 368

Trp Asn His His His Ser Thr Pro His Pro Ala His
1               5                   10

<210> SEQ ID NO 369
<211> LENGTH: 21
<212> TYPE: PRT
<213> ORGANISM: Artificial sequence
<220> FEATURE:
<223> OTHER INFORMATION: peptide

<400> SEQUENCE: 369

Ser Phe Ile Leu Phe Ile Arg Arg Gly Arg Leu Gly Arg Arg Arg
1               5                   10                  15

Arg Arg Arg Arg Arg
            20

<210> SEQ ID NO 370
<211> LENGTH: 20
<212> TYPE: PRT
<213> ORGANISM: Artificial sequence
<220> FEATURE:
<223> OTHER INFORMATION: peptide
<220> FEATURE:
<221> NAME/KEY: D-amino_acid
<222> LOCATION: (1)..(20)

<400> SEQUENCE: 370

Arg Arg Arg Arg Arg Arg Arg Arg Gly Leu Arg Gly Arg Arg Ile Phe

```
                1               5                  10                 15

Leu Ile Phe Ser
            20

<210> SEQ ID NO 371
<211> LENGTH: 15
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 371

Arg Arg His Asn Ala His His Ser Thr Pro His Pro Asp Asp Arg
1               5                  10                 15

<210> SEQ ID NO 372
<211> LENGTH: 6
<212> TYPE: PRT
<213> ORGANISM: Artificial sequence
<220> FEATURE:
<223> OTHER INFORMATION: peptide

<400> SEQUENCE: 372

His Ser Thr Pro His Pro
1               5

<210> SEQ ID NO 373
<211> LENGTH: 20
<212> TYPE: PRT
<213> ORGANISM: Artificial sequence
<220> FEATURE:
<223> OTHER INFORMATION: peptide

<400> SEQUENCE: 373

Leu Arg Cys Leu Leu Leu Leu Ile Gly Arg Val Gly Arg Lys Lys Arg
1               5                  10                 15

Arg Gln Arg Arg
            20

<210> SEQ ID NO 374
<211> LENGTH: 16
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 374

Arg Arg Lys His Asn Lys His Arg Pro Glu Pro Asp Ser Asp Glu Arg
1               5                  10                 15

<210> SEQ ID NO 375
<211> LENGTH: 14
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated
```

<400> SEQUENCE: 375

Arg Arg Ile Arg Asp Pro Arg Ile Leu Leu Leu His Phe Asp
1               5                   10

<210> SEQ ID NO 376
<211> LENGTH: 20
<212> TYPE: PRT
<213> ORGANISM: Artificial sequence
<220> FEATURE:
<223> OTHER INFORMATION: peptide

<400> SEQUENCE: 376

Arg Lys Arg Gly Lys Ser Tyr Ala Phe Phe Val Pro Pro Ser Glu Ser
1               5                   10                  15

Lys Glu Arg Trp
            20

<210> SEQ ID NO 377
<211> LENGTH: 14
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 377

Arg Arg Lys Ile Leu Phe Ile Arg Leu Met His Asn Lys His
1               5                   10

<210> SEQ ID NO 378
<211> LENGTH: 16
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 378

Arg Arg Leu Ile Val Arg Ile Leu Lys Leu Pro Asn Pro Pro Glu Arg
1               5                   10                  15

<210> SEQ ID NO 379
<211> LENGTH: 9
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: N terminus myristlyated

<400> SEQUENCE: 379

Arg Arg His Ser Thr Pro His Pro Asp
1               5

<210> SEQ ID NO 380
<211> LENGTH: 12
<212> TYPE: PRT
<213> ORGANISM: Artificial sequence
<220> FEATURE:

<223> OTHER INFORMATION: peptide

<400> SEQUENCE: 380

Lys Pro Pro Asp Arg Leu Trp His Tyr Thr Gln Pro
1               5                   10

<210> SEQ ID NO 381
<211> LENGTH: 12
<212> TYPE: PRT
<213> ORGANISM: Artificial sequence
<220> FEATURE:
<223> OTHER INFORMATION: peptide

<400> SEQUENCE: 381

Ala Thr Leu Pro Phe Val Thr Asp Arg Gln Gly Trp
1               5                   10

<210> SEQ ID NO 382
<211> LENGTH: 12
<212> TYPE: PRT
<213> ORGANISM: Artificial sequence
<220> FEATURE:
<223> OTHER INFORMATION: peptide

<400> SEQUENCE: 382

Phe Tyr Ser His Ser Thr Ser Pro Ala Pro Ala Lys
1               5                   10

<210> SEQ ID NO 383
<211> LENGTH: 12
<212> TYPE: PRT
<213> ORGANISM: Artificial sequence
<220> FEATURE:
<223> OTHER INFORMATION: peptide

<400> SEQUENCE: 383

Cys Tyr Ser His Ser Tyr Pro Thr Gln Gly His Leu
1               5                   10

<210> SEQ ID NO 384
<211> LENGTH: 12
<212> TYPE: PRT
<213> ORGANISM: Artificial sequence
<220> FEATURE:
<223> OTHER INFORMATION: peptide

<400> SEQUENCE: 384

Glu Phe His Ser Phe Tyr Thr Ala Arg Gln Thr Gly
1               5                   10

<210> SEQ ID NO 385
<211> LENGTH: 12
<212> TYPE: PRT
<213> ORGANISM: Artificial sequence
<220> FEATURE:
<223> OTHER INFORMATION: peptide

<400> SEQUENCE: 385

Ser Asp Gly Phe Val Pro His Phe Lys Arg Gln His
1               5                   10

<210> SEQ ID NO 386
<211> LENGTH: 7
<212> TYPE: PRT
<213> ORGANISM: Artificial sequence
<220> FEATURE:
<223> OTHER INFORMATION: peptide

```
<400> SEQUENCE: 386

Leu Pro Asn Pro Pro Glu Arg
1               5

<210> SEQ ID NO 387
<211> LENGTH: 7
<212> TYPE: PRT
<213> ORGANISM: Artificial sequence
<220> FEATURE:
<223> OTHER INFORMATION: peptide

<400> SEQUENCE: 387

Leu His Ser Lys Thr Leu Val
1               5

<210> SEQ ID NO 388
<211> LENGTH: 6
<212> TYPE: PRT
<213> ORGANISM: Artificial sequence
<220> FEATURE:
<223> OTHER INFORMATION: peptide

<400> SEQUENCE: 388

His Val His Thr His Gln
1               5

<210> SEQ ID NO 389
<211> LENGTH: 7
<212> TYPE: PRT
<213> ORGANISM: Artificial sequence
<220> FEATURE:
<223> OTHER INFORMATION: peptide

<400> SEQUENCE: 389

Ser Ser Ser Leu Gly Thr His
1               5

<210> SEQ ID NO 390
<211> LENGTH: 7
<212> TYPE: PRT
<213> ORGANISM: Artificial sequence
<220> FEATURE:
<223> OTHER INFORMATION: peptide

<400> SEQUENCE: 390

His Glu Val Thr His His Trp
1               5

<210> SEQ ID NO 391
<211> LENGTH: 7
<212> TYPE: PRT
<213> ORGANISM: Artificial sequence
<220> FEATURE:
<223> OTHER INFORMATION: peptide

<400> SEQUENCE: 391

Ser Ala Pro Gln Pro Ala Thr
1               5

<210> SEQ ID NO 392
<211> LENGTH: 7
<212> TYPE: PRT
<213> ORGANISM: Artificial sequence
<220> FEATURE:
<223> OTHER INFORMATION: peptide
```

```
<400> SEQUENCE: 392

Thr Pro Pro Leu Thr Leu Ile
1               5

<210> SEQ ID NO 393
<211> LENGTH: 6
<212> TYPE: PRT
<213> ORGANISM: Artificial sequence
<220> FEATURE:
<223> OTHER INFORMATION: peptide

<400> SEQUENCE: 393

His Pro Trp Thr His His
1               5

<210> SEQ ID NO 394
<211> LENGTH: 7
<212> TYPE: PRT
<213> ORGANISM: Artificial sequence
<220> FEATURE:
<223> OTHER INFORMATION: peptide

<400> SEQUENCE: 394

Ser Ala Ala Ser Asp Leu Arg
1               5

<210> SEQ ID NO 395
<211> LENGTH: 7
<212> TYPE: PRT
<213> ORGANISM: Artificial sequence
<220> FEATURE:
<223> OTHER INFORMATION: peptide

<400> SEQUENCE: 395

Ser Pro Leu Gln Ser Leu Lys
1               5

<210> SEQ ID NO 396
<211> LENGTH: 7
<212> TYPE: PRT
<213> ORGANISM: Artificial sequence
<220> FEATURE:
<223> OTHER INFORMATION: peptide

<400> SEQUENCE: 396

Arg Pro Thr Gln Val Leu His
1               5

<210> SEQ ID NO 397
<211> LENGTH: 12
<212> TYPE: PRT
<213> ORGANISM: Artificial sequence
<220> FEATURE:
<223> OTHER INFORMATION: peptide

<400> SEQUENCE: 397

Phe Arg Ser Phe Ala Ile Pro Leu Val Val Pro Phe
1               5                   10

<210> SEQ ID NO 398
<211> LENGTH: 12
<212> TYPE: PRT
<213> ORGANISM: Artificial sequence
<220> FEATURE:
<223> OTHER INFORMATION: peptide

<400> SEQUENCE: 398
```

```
Lys Ile Leu Phe Ile Arg Leu Met His Asn Lys His
1               5                   10
```

<210> SEQ ID NO 399
<211> LENGTH: 4
<212> TYPE: PRT
<213> ORGANISM: Artificial sequence
<220> FEATURE:
<223> OTHER INFORMATION: peptide

<400> SEQUENCE: 399

```
His His His Pro
1
```

<210> SEQ ID NO 400
<211> LENGTH: 4
<212> TYPE: PRT
<213> ORGANISM: Artificial sequence
<220> FEATURE:
<223> OTHER INFORMATION: peptide

<400> SEQUENCE: 400

```
His Thr Ile His
1
```

<210> SEQ ID NO 401
<211> LENGTH: 4
<212> TYPE: PRT
<213> ORGANISM: Artificial sequence
<220> FEATURE:
<223> OTHER INFORMATION: peptide

<400> SEQUENCE: 401

```
His Asn Lys His
1
```

<210> SEQ ID NO 402
<211> LENGTH: 5
<212> TYPE: PRT
<213> ORGANISM: Artificial sequence
<220> FEATURE:
<223> OTHER INFORMATION: peptide

<400> SEQUENCE: 402

```
Leu Leu Leu Ile Gly
1               5
```

<210> SEQ ID NO 403
<211> LENGTH: 5
<212> TYPE: PRT
<213> ORGANISM: Artificial sequence
<220> FEATURE:
<223> OTHER INFORMATION: peptide

<400> SEQUENCE: 403

```
Ile Leu Phe Ile Arg
1               5
```

<210> SEQ ID NO 404
<211> LENGTH: 6
<212> TYPE: PRT
<213> ORGANISM: Artificial sequence
<220> FEATURE:
<223> OTHER INFORMATION: peptide

<400> SEQUENCE: 404

Ile Arg Gly Arg Ile Ile
1               5

<210> SEQ ID NO 405
<211> LENGTH: 7
<212> TYPE: PRT
<213> ORGANISM: Artificial sequence
<220> FEATURE:
<223> OTHER INFORMATION: peptide

<400> SEQUENCE: 405

Ser Phe Ile Leu Phe Ile Arg
1               5

<210> SEQ ID NO 406
<211> LENGTH: 7
<212> TYPE: PRT
<213> ORGANISM: Artificial sequence
<220> FEATURE:
<223> OTHER INFORMATION: peptide

<400> SEQUENCE: 406

Tyr Pro Thr Gln Gly His Leu
1               5

<210> SEQ ID NO 407
<211> LENGTH: 10
<212> TYPE: PRT
<213> ORGANISM: Artificial sequence
<220> FEATURE:
<223> OTHER INFORMATION: peptide

<400> SEQUENCE: 407

Trp Asn His His His Ser Thr Pro His Pro
1               5                   10

<210> SEQ ID NO 408
<211> LENGTH: 11
<212> TYPE: PRT
<213> ORGANISM: Artificial sequence
<220> FEATURE:
<223> OTHER INFORMATION: peptide

<400> SEQUENCE: 408

Ile Arg Ile Leu Met Phe Leu Ile Gly Cys Gly
1               5                   10

<210> SEQ ID NO 409
<211> LENGTH: 12
<212> TYPE: PRT
<213> ORGANISM: Artificial sequence
<220> FEATURE:
<223> OTHER INFORMATION: peptide

<400> SEQUENCE: 409

Ser Trp Gln Ala Leu Ala Leu Tyr Ala Ala Gly Trp
1               5                   10

<210> SEQ ID NO 410
<211> LENGTH: 12
<212> TYPE: PRT
<213> ORGANISM: Artificial sequence
<220> FEATURE:
<223> OTHER INFORMATION: peptide
<220> FEATURE:
<221> NAME/KEY: D-amino_acids
<222> LOCATION: (1)..(12)

```
<400> SEQUENCE: 410

Gly Leu Arg Gly Arg Arg Ile Phe Leu Ile Phe Ser
1               5                   10

<210> SEQ ID NO 411
<211> LENGTH: 18
<212> TYPE: PRT
<213> ORGANISM: Artificial sequence
<220> FEATURE:
<223> OTHER INFORMATION: peptide

<400> SEQUENCE: 411

Leu Arg Cys Leu Leu Leu Leu Ile Gly Arg Val Gly Arg Lys Lys Arg
1               5                   10                  15

Arg Gln

<210> SEQ ID NO 412
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 412

Arg Arg His Ser Thr Pro His Pro Gly Glu
1               5                   10

<210> SEQ ID NO 413
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 413

Arg Arg His Ser Thr Pro His Pro Ser Glu
1               5                   10

<210> SEQ ID NO 414
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 414

Arg Arg His Ser Thr Pro His Pro Ala Asp
1               5                   10

<210> SEQ ID NO 415
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
```

```
<221> NAME/KEY: MISC_FEATURE
<222> LOCATION: (1)..(1)
<223> OTHER INFORMATION: N terminus myristlyated

<400> SEQUENCE: 415

Arg Arg His Ser Thr Pro His Pro Ala Glu
1               5                   10

<210> SEQ ID NO 416
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 416

Arg Arg His Ser Ser Pro His Pro Asp
1               5

<210> SEQ ID NO 417
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 417

Arg Arg His Ser Val Pro His Pro Asp
1               5

<210> SEQ ID NO 418
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 418

Arg Arg His Ser Cys Pro His Pro Asp
1               5

<210> SEQ ID NO 419
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Glutamic Acid

<400> SEQUENCE: 419

Arg Arg His Ser Glu Pro His Pro Asp
```

```
<210> SEQ ID NO 420
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Threonine

<400> SEQUENCE: 420

Arg Arg His Ser Thr Pro His Pro Asp
1               5

<210> SEQ ID NO 421
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Serine

<400> SEQUENCE: 421

Arg Arg His Ser Ser Pro His Pro Asp
1               5

<210> SEQ ID NO 422
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Valine

<400> SEQUENCE: 422

Arg Arg His Ser Val Pro His Pro Asp
1               5

<210> SEQ ID NO 423
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (3)..(3)
```

<223> OTHER INFORMATION: X is L- Diaminobutyric Acid (L-DAB)

<400> SEQUENCE: 423

Arg Arg Xaa Ser Thr Pro His Pro Asp
1               5

<210> SEQ ID NO 424
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 424

Arg Arg His Ser Thr Pro Xaa Pro Asp
1               5

<210> SEQ ID NO 425
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (10)..(10)
<223> OTHER INFORMATION: Methylated Amino Acid Residue

<400> SEQUENCE: 425

Arg Arg His Ser Thr Pro His Pro Asp Asp
1               5                   10

<210> SEQ ID NO 426
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 426

Arg Arg His Ser Thr Pro His Ala Asp
1               5

<210> SEQ ID NO 427
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 427

Arg Arg His Ser Lys Pro His Pro Asp
1               5

<210> SEQ ID NO 428
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 428

Arg Arg His Ser Ser Pro Xaa Pro Asp
1               5

<210> SEQ ID NO 429
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Valine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 429

Arg Arg His Ser Val Pro Xaa Pro Asp
1               5

<210> SEQ ID NO 430
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 430

Arg Arg His Ser Thr Pro Xaa Ala Asp
1               5

<210> SEQ ID NO 431
<211> LENGTH: 9
<212> TYPE: PRT
<213> ORGANISM: Artificial sequence
<220> FEATURE:
<223> OTHER INFORMATION: pCAP 250 peptide variant
<220> FEATURE:

<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Serine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 431

Arg Arg His Ser Ser Pro Xaa Pro Asp
1               5

<210> SEQ ID NO 432
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (10)..(10)
<223> OTHER INFORMATION: C-Terminal Amidation

<400> SEQUENCE: 432

Arg Arg His Ser Lys Pro His Pro Asp Asp
1               5                   10

<210> SEQ ID NO 433
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 433

Arg Arg Xaa Ser Thr Pro Xaa Pro Asp
1               5

<210> SEQ ID NO 434
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 434

Arg Arg His Ser Lys Pro Xaa Pro Asp
1               5

<210> SEQ ID NO 435
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)

<400> SEQUENCE: 435

Arg Arg Xaa Ser Lys Pro His Pro Asp
1               5

<210> SEQ ID NO 436
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 436

Arg Arg Xaa Ser Lys Pro Xaa Pro Asp
1               5

<210> SEQ ID NO 437
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 437

Arg Arg His Ser Lys Pro His Ala Asp
1               5

<210> SEQ ID NO 438
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 438

Arg Arg His Ser Lys Pro His Ala Ser Glu
1               5                   10

<210> SEQ ID NO 439
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 439

Arg Arg His Ser Lys Pro His Pro Ser Glu
1               5                   10

<210> SEQ ID NO 440
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)
<220> FEATURE:
<221> NAME/KEY: MISC_FEATURE
<222> LOCATION: (5)..(5)
<223> OTHER INFORMATION: D Serine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 440

Arg Arg Xaa Ser Ser Pro Xaa Pro Asp
1               5

<210> SEQ ID NO 441
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)
<220> FEATURE:
<221> NAME/KEY: MISC_FEATURE
<222> LOCATION: (5)..(5)
<223> OTHER INFORMATION: D Valine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 441

Arg Arg Xaa Ser Val Pro Xaa Pro Asp

```
1               5

<210> SEQ ID NO 442
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 442

Arg Arg His Ser Thr Pro His Ala Ser Glu
1               5                   10

<210> SEQ ID NO 443
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Lysine

<400> SEQUENCE: 443

Arg Arg His Ser Lys Pro His Pro Asp
1               5

<210> SEQ ID NO 444
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: MYRISTATE group attached
<220> FEATURE:
<221> NAME/KEY: misc_feature
<222> LOCATION: (5)..(5)
<223> OTHER INFORMATION: X is L- Diaminobutyric Acid (L-DAB)

<400> SEQUENCE: 444

Arg Arg His Ser Xaa Pro His Pro Asp
1               5

<210> SEQ ID NO 445
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (5)..(5)
<223> OTHER INFORMATION: X is L- Diaminobutyric Acid (L-DAB)

<400> SEQUENCE: 445
```

```
Arg Arg His Ser Xaa Pro His Ala Asp
1               5

<210> SEQ ID NO 446
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 446

Arg Arg His Ser Glu Pro Xaa Pro Asp
1               5

<210> SEQ ID NO 447
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)

<400> SEQUENCE: 447

Arg Arg Xaa Ser Glu Pro His Pro Asp
1               5

<210> SEQ ID NO 448
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D Valine
<220> FEATURE:
<221> NAME/KEY: misc_feature
<222> LOCATION: (7)..(7)
<223> OTHER INFORMATION: X is L- Diaminobutyric Acid (L-DAB)
<220> FEATURE:
<221> NAME/KEY: MISC_FEATURE
<222> LOCATION: (9)..(9)
<223> OTHER INFORMATION: C-Terminal Amidation

<400> SEQUENCE: 448

Arg Arg His Ser Val Pro Xaa Pro Asp
1               5

<210> SEQ ID NO 449
<211> LENGTH: 9
<212> TYPE: PRT
<213> ORGANISM: Artificial sequence
```

```
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (6)..(6)
<223> OTHER INFORMATION: X is 2-Aminoisobutyric acid ( Aib)

<400> SEQUENCE: 449

Arg Arg His Ser Thr Xaa His Ala Asp
1               5

<210> SEQ ID NO 450
<211> LENGTH: 13
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 450

Arg Arg His Ser Thr Pro His Pro Asp Ile Glu Gly Arg
1               5                   10

<210> SEQ ID NO 451
<211> LENGTH: 21
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 451

Arg Arg His Ser Thr Pro His Pro Asp Ile Glu Gly Arg Gly Trp Gln
1               5                   10                  15

Arg Pro Ser Ser Trp
            20

<210> SEQ ID NO 452
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 452

Arg Arg Xaa Ser Glu Pro Xaa Pro Asp
1               5
```

```
<210> SEQ ID NO 453
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)
<220> FEATURE:
<221> NAME/KEY: MISC_FEATURE
<222> LOCATION: (9)..(9)
<223> OTHER INFORMATION: C-Terminal Amidation

<400> SEQUENCE: 453

Arg Arg His Ser Glu Pro Xaa Pro Asp
1               5

<210> SEQ ID NO 454
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (3)..(3)
<223> OTHER INFORMATION: X is L- Diaminobutyric Acid (L-DAB)

<400> SEQUENCE: 454

Arg Arg Xaa Ser Glu Pro His Pro Asp
1               5

<210> SEQ ID NO 455
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: L-Phosphoserine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 455

Arg Arg His Ser Ser Pro Xaa Pro Asp
1               5

<210> SEQ ID NO 456
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
```

```
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D-Phosphoserine
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 456

Arg Arg His Ser Ser Pro Xaa Pro Asp
1               5

<210> SEQ ID NO 457
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: L-Phosphoserine
<220> FEATURE:
<221> NAME/KEY: misc_feature
<222> LOCATION: (7)..(7)
<223> OTHER INFORMATION: X is L- Diaminobutyric Acid (L-DAB)
<220> FEATURE:
<221> NAME/KEY: MISC_FEATURE
<222> LOCATION: (9)..(9)
<223> OTHER INFORMATION: C-Terminal Amidation

<400> SEQUENCE: 457

Arg Arg His Ser Ser Pro Xaa Pro Asp
1               5

<210> SEQ ID NO 458
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (7)..(7)
<223> OTHER INFORMATION: X is L- Diaminobutyric Acid (L-DAB)

<400> SEQUENCE: 458

Arg Arg His Ser Lys Pro Xaa Pro Asp
1               5

<210> SEQ ID NO 459
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
```

<222> LOCATION: (3)..(3)
<223> OTHER INFORMATION: X is L- Diaminobutyric Acid (L-DAB)

<400> SEQUENCE: 459

Arg Arg Xaa Ser Lys Pro His Pro Asp
1               5

<210> SEQ ID NO 460
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 460

Arg Arg His Ser Thr Pro His Pro Ala His
1               5                   10

<210> SEQ ID NO 461
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: misc_feature
<222> LOCATION: (10)..(10)
<223> OTHER INFORMATION: X is L- Diaminobutyric Acid (L-DAB)

<400> SEQUENCE: 461

Arg Arg His Ser Thr Pro His Pro Ala Xaa
1               5                   10

<210> SEQ ID NO 462
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 462

Arg Arg His Ser Thr Pro His Pro Asp His
1               5                   10

<210> SEQ ID NO 463
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated
<220> FEATURE:
<221> NAME/KEY: MISC_FEATURE
<222> LOCATION: (5)..(5)
<223> OTHER INFORMATION: D-Valine
<220> FEATURE:

```
<221> NAME/KEY: misc_feature
<222> LOCATION: (7)..(7)
<223> OTHER INFORMATION: X is L- Diaminobutyric Acid (L-DAB)

<400> SEQUENCE: 463

Arg Arg His Ser Val Pro Xaa Pro Asp His
1               5                   10

<210> SEQ ID NO 464
<211> LENGTH: 10
<212> TYPE: PRT
<213> ORGANISM: Artificial sequence
<220> FEATURE:
<223> OTHER INFORMATION: pCAP 250 peptide variant
<220> FEATURE:
<221> NAME/KEY: MISC_FEATURE
<222> LOCATION: (1)..(1)
<223> OTHER INFORMATION: N terminus myristlyated

<400> SEQUENCE: 464

Arg Arg His Ser Thr Pro His Ala Asp His
1               5                   10

<210> SEQ ID NO 465
<211> LENGTH: 9
<212> TYPE: PRT
<213> ORGANISM: Artificial sequence
<220> FEATURE:
<223> OTHER INFORMATION: pCAP 250 peptide variant
<220> FEATURE:
<221> NAME/KEY: misc_feature
<222> LOCATION: (7)..(7)
<223> OTHER INFORMATION: X is  Diaminobutyric Acid (DAB)

<400> SEQUENCE: 465

Arg Arg His Ser Thr Pro Xaa Pro Asp
1               5
```